US012643894B2

(12) United States Patent
Voisin-Chiret et al.

(10) Patent No.: US 12,643,894 B2
(45) Date of Patent: Jun. 2, 2026

(54) BCL-2 FAMILY PROTEINS MODULATING COMPOUNDS FOR CANCER TREATMENT

(71) Applicants: CENTRE REGIONAL DE LUTTE CONTRE LE CANCER FRANCOIS BACLESSE, Caen Cedex (FR); UNIVERSITE DE CAEN NORMANDIE, Caen (FR); INSTITUT NATIONAL DE LA SANTE ET DE LA RECHERCHE MEDICALE, Paris (FR)

(72) Inventors: Anne-Sophie Voisin-Chiret, Caen Cedex (FR); Charline Kieffer, Caen Cedex (FR); Nicolas Guedeney, Caen Cedex (FR); Camille Denis, Caen Cedex (FR); Martina De Pascale, Caen Cedex (FR); Laurent Poulain, Caen Cedex (FR); Louis Bastien Weiswald, Caen Cedex (FR); Hippolyte Paysant, Caen Cedex (FR)

(73) Assignees: CENTRE REGIONAL DE LUTTE CONTRE LE CANCER FRANCOIS BACLESSE, Caen Cedex (FR); UNIVERSITE DE CAEN NORMANDIE, Caen (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 866 days.

(21) Appl. No.: 17/909,916

(22) PCT Filed: Mar. 12, 2021

(86) PCT No.: PCT/EP2021/056415
§ 371 (c)(1),
(2) Date: Sep. 7, 2022

(87) PCT Pub. No.: WO2021/180966
PCT Pub. Date: Sep. 16, 2021

(65) Prior Publication Data

US 2024/0228477 A1 Jul. 11, 2024

(30) Foreign Application Priority Data

Mar. 13, 2020 (EP) .................................... 20305263

(51) Int. Cl.

| | |
|---|---|
| *C07D 419/02* | (2006.01) |
| *A61K 47/54* | (2017.01) |
| *C07D 401/14* | (2006.01) |
| *C07D 417/14* | (2006.01) |

(52) U.S. Cl.
CPC .......... *C07D 417/14* (2013.01); *A61K 47/545* (2017.08); *C07D 401/14* (2013.01)

(58) Field of Classification Search
CPC .................................................... C07D 419/02
See application file for complete search history.

(56) References Cited

FOREIGN PATENT DOCUMENTS

| | | | |
|---|---|---|---|
| WO | 2015132727 | A1 | 9/2015 |
| WO | 2019060742 | A1 | 3/2019 |
| WO | 2019140380 | A1 | 7/2019 |
| WO | 2020010227 | A1 | 1/2020 |

OTHER PUBLICATIONS

International Search Report and Written Opinion for PCT Application No. PCT/EP2021/056415, dated May 3, 2021, pp. 1-9.
Gloaguen et al., "First Evidence That Oligopyridines, a-Helix Foldamers, Inhibit Mcl-1 and Sensitize OVarian Carcinoma Cells to Bcl-xL-Targeting Strategies," Journal of Medicinal Chemistry, 2015, pp. 1664-1668, vol. 58, ACS Publications, France.

*Primary Examiner* — John S Kenyon
(74) *Attorney, Agent, or Firm* — Dickinson Wright PLLC

(57) ABSTRACT

The present disclosure relates to compounds, compositions and methods for treating cancers and disorders of cell proliferation and more particularly, methods of making and using compounds that modulate at least one of the proteins chosen from Bcl-2, Mcl-1, Bcl-$x_L$, Bcl-w, Bfl-1 and Bcl-B, in particular Bcl-2 protein, or Bcl-$x_L$ and/or Mcl-1 proteins. The compounds may be contained in pharmaceutical compositions and used as therapeutic agents.

18 Claims, 1 Drawing Sheet

BCL-2 FAMILY PROTEINS MODULATING COMPOUNDS FOR CANCER TREATMENT

CROSS-REFERENCE TO RELATED APPLICATION(S)

Figure 1:
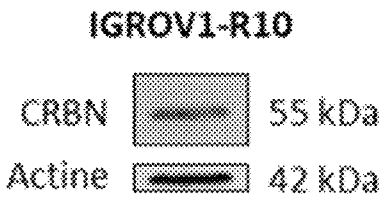

This present application is a national stage application of International Patent Application No. PCT/EP2021/056415, filed Mar. 12, 2021, which claims priority to European Patent Application No. 20305263.4, filed Mar. 13, 2020, the disclosures of which are hereby incorporated by reference in their entireties.

The present invention relates to compounds, compositions and methods for treating cancers and disorders of cell proliferation and more particularly, methods of making and using compounds that modulate at least one of the proteins chosen from Bcl-2, Mcl-1, Bcl-$x_L$, Bcl-w, Bfl-1 and Bcl-B, in particular Bcl-2 protein, or Bcl-$x_L$ and/or Mcl-1 proteins; said compounds may be contained in pharmaceutical compositions and used as therapeutic agents.

Cancer is a leading cause of death worldwide. Apoptosis, also known as programmed cell death, is a natural process used by multicellular organisms to eliminate aging or damaged cells also involved in various physiological processes such as morphogenesis and tissue homeostasis. Apoptosis is a complex, highly regulated process involving many proteins. Some of these proteins promote cell death ("pro-apoptotic" proteins) and some prevent it ("anti-apoptotic" proteins). Cancer cells tend to over-express anti-apoptotic genes. The overexpression of anti-apoptotic genes is associated with tumor formation, metastatic growth and resistance to chemotherapy and there is a continuing need for therapeutic strategies that selectively kill cancer cells.

More specifically, apoptosis control defect is frequently involved in chemoresistance in cancer cells, in both hematological malignancies and solid tumors, and the deregulation of Bcl-2 family members expression constitutes one of the most frequent and important event. These proteins share Bcl-2 homology domains (named BH domains). Anti-apoptotic proteins (Bcl-2, Bcl-$x_L$ . . . ) contain the BH1 to BH4 domains, whereas pro-apoptotic proteins contain either the BH1 to BH3 domains (multidomain members such as Bax and Bak) or only the BH3 domain (BH3-only group such as Bim, Puma, Bid, Bad, Noxa and Hrk). Under cellular stress, BH3-only proteins initiate apoptosis by either blocking the activity of anti-apoptotic members or directly activating multidomain pro-apoptotic members, which is mediated via interaction of the BH3 domain of one protein with the hydrophobic pocket of another.

Constant efforts are made to impede the activity of anti-apoptotic members such as Bcl-2 or Bcl-$x_L$, among which the development of potent BH3-mimetic molecules represent a promising way. These molecules bind to the BH3-binding groove in anti-apoptotic proteins of the Bcl-2 family and promote cell death through the release of pro-apoptotic Bcl-2 family members.

In ovarian carcinoma, inventors previously demonstrated that Bcl-$x_L$ and Mcl-1 cooperate to protect tumor cells against apoptosis, and that their concomitant inhibition leads to massive apoptosis even in absence of chemotherapy, whereas the down-regulation of either Bcl-$x_L$ or Mcl-1 may in some cases remain ineffective. In this context, they also showed that Mcl-1 down regulation or inactivation was required to sensitize ovarian cancer cells to Bcl-$x_L$-targeting BH3-mimetic molecules such as ABT-737.

In hematological malignancies, including lymphomas, the interest of the targeting of Bcl-2 family anti-apoptotic proteins has been extensively documented. For instance, Bcl-2 has been successfully targeted in vitro as well as in vivo by the US FDA-approved BCL-2 inhibitor Venetoclax (or Venclaxta, developed by Abbvie) that has been found to be clinically active against various hematologic malignancies including multiple myeloma, acute myeloid leukemia, myelodysplastic syndrome, acute lymphoblastic leukemia, small lymphocytic lymphoma and others.

Other studies also showed that the inhibition of Mcl-1 improves the therapeutic efficiency of Bcl-2 or Bcl-$x_L$-targeting BH3-mimetics in hematological malignancies. In other lymphoid malignancies, such as the aggressive mantle cell lymphoma (MCL), cell survival might rely instead or also on BCL-2 relative Mcl-1.

Mcl-1 contains three BH domains (BH1-BH3) but lacks a clearly defined BH4 domain at the $NH_2$ terminus. Mcl-1 localizes to various intracellular membranes, especially, the outer mitochondrial membrane through a transmembrane domain at its COOH terminus. Like Bcl-2 and Bcl-$x_L$, Mcl-1 can interact with Bak to inhibit mitochondria-mediated apoptosis. Unlike Bcl-2 and Bcl-$x_L$, Mcl-1 expression is quickly induced upon exposure to cytokines or growth factors. Increased Mcl-1 expression promotes cell viability in a wide range of tumor cell types, including leukemias, hepatocellular carcinomas, melanoma, prostate and breast cancer cells. Moreover, Mcl-1 plays a role in cell immortalization and tumorigenesis in many kinds of cancers through amplification of somatic copy number. Cancer cells harboring Mcl-1 amplification are frequently dependent upon Mcl-1 for survival.

Mcl-1 is overexpressed in various tumor cells, including ovarian carcinoma, hematological malignancies, breast cancers, colon cancers and lung cancers, and its expression has also been associated to chemoresistance. Importantly, Mcl-1 locus is one of the most frequently amplified in human cancers, further pointing to its centrality in carcinogenesis and increasing its importance as a high priority therapeutic target.

However, the development of several molecules inhibiting the Mcl-1 pathway has been recently abandoned for reasons of cardiac toxicity.

Among the other promising therapeutic targets, the anti-apoptotic Bcl-$x_L$ protein constitute a target of choice. This is particularly true in the management of certain solid tumors, which overexpress this protein (including ovarian tumors), and whose expression is strongly correlated with drug resistance. Although the pharmacological benefit of targeting this protein is not questioned at present, the development of molecules inhibiting this protein is currently hampered by the emergence of thrombocytopenia in patients.

Accordingly, it is an object of the present invention to provide alternative compounds useful for modulating Mcl-1 activity and/or Bcl-$x_L$, in particular degrading Mcl-1 and/or Bcl-$x_L$ protein, while having no or low toxicity towards heart and platelets.

Another object of the present invention is to provide alternative compounds to treat cancer, notably hematologic malignancies, such as lymphomas, and/or solid tumors, such as ovarian cancers, while having no or low toxicity towards heart and platelets.

The present invention is thus directed, in one aspect, to a compound of following formula (I)

(I)

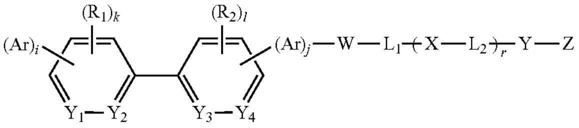

Wherein:

$Y_1$, $Y_2$, $Y_3$ and $Y_4$ are each independently C or N, $Y_1$ and $Y_2$ being such as one is N and the other is C, $Y_3$ and $Y_4$ being such as one is N and the other is C;

$Ar_1$, $Ar_2$ are each independently selected from ($C_6$-$C_{10}$)aryl, (5 to 7 membered) heteroaryl, —O—($C_6$-$C_{10}$)aryl, —O-(5 to 7 membered)heteroaryl, —S—($C_6$-$C_{10}$)aryl, —S-(5 to 7 membered)heteroaryl, —($C_1$-$C_6$)alkyl-($C_6$-$C_{10}$)aryl, —($C_1$-$C_6$)alkyl-(5 to 7 membered) heteroaryl and halogens, in particular Cl, said aryl and heteroaryl groups being optionally substituted by one to three $R_3$ groups, i and j are independently 0 or 1, and $R_1$, $R_2$, are at each occurrence, independently selected from ($C_1$-$C_6$)alkyl, ($C_6$-$C_{10}$)aryl, —($C_1$-$C_6$)alkyl-($C_6$-$C_{10}$)aryl, —($C_2$-$C_6$)alkenyl-($C_6$-$C_{10}$)aryl, -carbonyl-($C_6$-$C_{10}$)aryl-, -carbonyl-($C_1$-$C_6$)alkyl-($C_6$-$C_{10}$)aryl, C(═O)H, COOH, OH, said alkyl groups being optionally substituted by OH, said aryl groups being optionally substituted by one to three $R_4$ groups;

k and 1 are independently 0 or 1;

at least one of $(R_1)_k$ and $(R_2)_l$ being such as:

$R_1$ is selected from ($C_6$-$C_{10}$)aryl, —($C_1$-$C_6$)alkyl-($C_6$-$C_{10}$)aryl, —($C_2$-$C_6$)alkenyl-($C_6$-$C_{10}$)aryl, -carbonyl-($C_6$-$C_{10}$)aryl-, -carbonyl-($C_1$-$C_6$)alkyl-($C_6$-$C_{10}$)aryl, and k is 1; or $R_2$ is selected from ($C_6$-$C_{10}$)aryl, —($C_1$-$C_6$)alkyl-($C_6$-$C_{10}$)aryl, —($C_2$-$C_6$)alkenyl-($C_6$-$C_{10}$)aryl, -carbonyl-($C_6$-$C_{10}$)aryl-, -carbonyl-($C_1$-$C_6$)alkyl-($C_6$-$C_{10}$)aryl, and 1 is 1;

$R_3$ is, at each occurrence, independently selected from ($C_1$-$C_6$)alkyl, ($C_1$-$C_6$)alkoxy, OH, C(═O)H, $(CH_2)_m CONR_aR_b$, $C(=O)R_c$, $(CH_2)_nCO_2H$, $(CH_2)_nCO_2R_c$, $(CH_2)_pCN$, $(CH_2)_gC(=N(OH))NH_2$, $—SO_2NR_aR_b$, I, Cl, Br, F, ($C_6$-$C_{10}$)aryl, a (5 to 7 membered)heteroaryl, —($C_1$-$C_6$)alkyl-($C_6$-$C_{10}$)aryl, —($C_2$-$C_6$)alkenyl-($C_6$-$C_{10}$)aryl, said alkyl groups being optionally substituted by a OH, ($C_1$-$C_6$)alkoxy and/or —O—($C_6$-$C_{10}$)aryl group; $R_4$ is, at each occurrence, independently selected from ($C_1$-$C_6$)alkyl, $(CH_2)_nCO_2H$, $(CH_2)_n CO_2R_c$, I, Cl, Br, F, or there are two $R_4$ groups that form with the aryl to which they are bound a naphthyl;

$R_a$ and $R_b$ are independently chosen from H and ($C_1$-$C_6$) alkyl;

$R_c$ is chosen from H and ($C_1$-$C_6$)alkyl;

m is 0, 1, 2, 3;

n is 0, 1, 2, 3;

p is 0, 1, 2, 3;

q is 0, 1, 2, 3;

r is 0 or 1;

W and Y are each independently selected from a single bond, —CH═CH—, —C≡C—, —NH—, $—NR_5—$, —O—, —S—, —C(═O)NH—, —NHC(═O)—, —C(═O)O—, —OC(═O)—;

$R_5$ is, at each occurrence, independently selected from ($C_1$-$C_6$)alkyl, $L_1$ and $L_2$ are each independently selected from ($C_1$-$C_{18}$) alkyl, ($C_2$-$C_{18}$)alkenyl, and ($C_2$-$C_{18}$)alkynyl groups, said groups being optionally interrupted by one or more groups selected from —O—, —S—, $—NR_6—$;

$R_6$ is, at each occurrence, independently selected from H and ($C_1$-$C_6$)alkyl, X is selected from (5 to 7 membered) heteroaryl, in particular a triazole, —NH—, $—NR_7—$, —O—, —S—, —C(═O)NH—, —NHC(═O)—, —C(═O)O—, —OC(═O)—;

$R_7$ is selected from ($C_1$-$C_6$)alkyl,

Z is a E3 ubiquitin ligase ligand;

and the pharmaceutically acceptable salts thereof.

According to an embodiment, $Y_1$ and $Y_3$ are N, and $Y_2$ and $Y_4$ are C.

According to an embodiment, $Y_1$ and $Y_3$ are C, and $Y_2$ and $Y_4$ are N.

According to an embodiment, $Y_1$ and $Y_4$ are N, and $Y_2$ and $Y3_4$ are C.

According to an embodiment, when j is 0, then $Y_4$ is N.

According to an embodiment, the compound of formula (I) as defined above is of following formula (II):

(II)

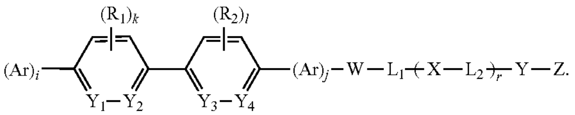

According to an embodiment, the compound as defined above is of following formula (IIIa) or (IIIb):

(IIIa)

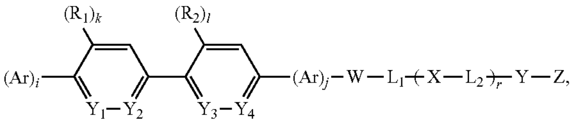

(IIIb)

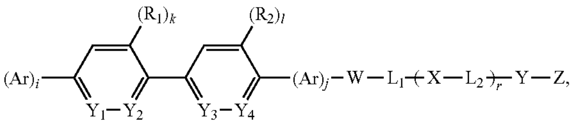

said compound being in particular of following formula (IIIa1) or (IIIa2), (IIIb1) or (IIIb2):

(IIIa1)

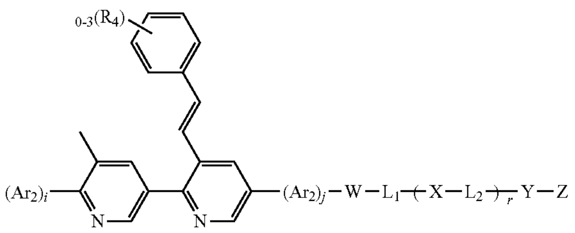

-continued (IIIa2)

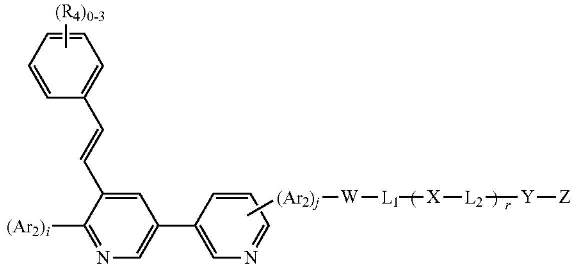

(IIIb1)

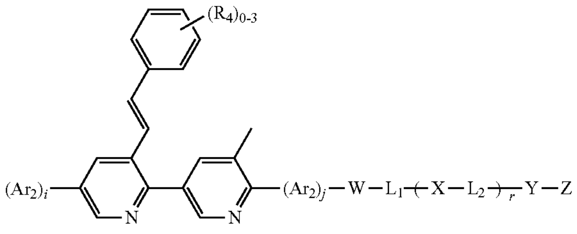

(IIIb2)

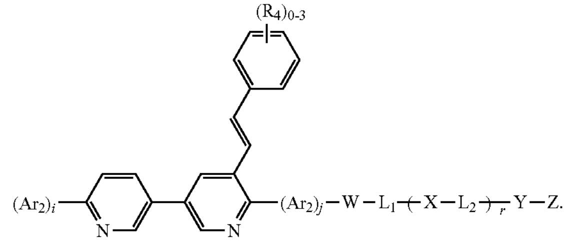

In a particular aspect, there are included compounds as defined above wherein at least one of $Ar_1$, $Ar_2$ is a (5 to 7 membered) heteroaryl, —O—($C_6$-$C_{10}$)aryl, —O-(5 to 7 membered)heteroaryl, —S—($C_6$-$C_{10}$)aryl, —S-(5 to 7 membered)heteroaryl, —($C_1$-$C_6$)alkyl-($C_6$-$C_{10}$)aryl, or —($C_1$-$C_6$)alkyl-(5 to 7 membered) heteroaryl, in particular a 5 to 7 membered heteroaryl containing a nitrogen atom, preferably pyridyl, notably 3-pyridyl.

In a particular aspect, there are included compounds as defined above wherein at least one of $Ar_1$, $Ar_2$ is a ($C_6$-$C_{10}$) aryl, in particular a phenyl.

According to an embodiment, $Ar_1$ and/or $Ar_2$ are selected from phenyl, pyridyl, pyrimidyl, imidazolyl, pyrazolyl, thiophenyl, triazolyl, in particular from phenyl, 3-pyridyl, 5-pyrimidyl, 2-imidazolyl, 3-pyrazolyl, 2-thiophenyl, 5-triazolyl.

According to an embodiment, $Ar_1$ is selected from pyridyl, in particular from 3-pyridyl, j being notably 0.

According to an embodiment, $Ar_1$ is 3-pyridyl or phenyl.

According to an embodiment, $Ar_2$ is 3-pyridyl or phenyl.

According to an embodiment, W is selected from —CH═CH— and —C≡C—, W being in particular —C≡C—, j being notably 0. According to an embodiment, $R_1$ and $R_2$ are independently selected from $C_1$-$C_6$ alkyl, in particular methyl, ($C_6$-$C_{10}$)aryl, in particular phenyl or naphthyl, —($C_1$-$C_6$)alkyl-($C_6$-$C_{10}$)aryl, in particular —($C_1$-$C_6$) alkyl-phenyl, more particularly phenetyl, and —($C_1$-$C_6$) alkyl-naphthyl, more particularly ethyl-naphthyl, and —($C_2$-$C_6$)alkenyl-($C_6$-$C_{10}$)aryl, in particular —($C_2$-$C_6$)alkenyl-phenyl, more particularly styryl, and —($C_2$-$C_6$)alkenyl-naphthyl, more particularly -vinyl-naphthyl.

According to a particular embodiment, $R_1$ is selected from $C_1$-$C_6$ alkyl and $R_2$ is selected from ($C_6$-$C_{10}$)aryl, —($C_1$-$C_6$)alkyl-($C_6$-$C_{10}$)aryl, and —($C_2$-$C_6$)alkenyl-($C_6$-$C_{10}$)aryl.

According to another particular embodiment, $R_2$ is selected from $C_1$-$C_6$ alkyl and $R_1$ is selected from ($C_6$-$C_{10}$) aryl, —($C_1$-$C_6$)alkyl-($C_6$-$C_{10}$)aryl, and —($C_2$-$C_6$)alkenyl-($C_6$-$C_{10}$)aryl.

According to an embodiment, $R_1$ and $R_2$ are independently selected from $C_1$-$C_6$ alkyl and ($C_6$-$C_{10}$)aryl($C_2$-$C_6$) alkenyl, preferably from methyl, styryl and 2-(naphthalen-2-yl)vinyl.

According to a particular embodiment, $R_1$ is selected from $C_1$-$C_6$ alkyl, in particular methyl and $R_2$ is selected from —($C_1$-$C_6$)alkyl-($C_6$-$C_{10}$)aryl, in particular styryl or 2-(naphthalen-2-yl)vinyl.

According to another particular embodiment, $R_2$ is selected from $C_1$-$C_6$ alkyl and $R_1$ is selected from ($C_6$-$C_{10}$) aryl, —($C_1$-$C_6$)alkyl-($C_6$-$C_{10}$)aryl, and —($C_2$-$C_6$)alkenyl-($C_6$-$C_{10}$)aryl.

According to an embodiment, $R_1$ is 5-methyl.

According to an embodiment, $R_2$ is 5-styryl or 2-(naphthalen-2-yl)vinyl.

According to another embodiment, $R_2$ is 5-methyl.

According to another embodiment, $R_1$ is 5-styryl or 2-(naphthalen-2-yl)vinyl.

In other aspects, there are included compounds of formula (I) wherein the pharmaceutically acceptable salts are hydrochloride, hydrobromide, hydroiodide, sulfate, nitrate, phosphate, acetate, citrate, propionate, fumarate, maleate, tartrate, glutamate, salicylate, oxalate, methanesulfonate, paratoluenesulfonate, succinate, or benzoate salts.

In other aspects, there are included compounds of formula (I) wherein the pharmaceutically acceptable salts are calcium, magnesium, lithium, potassium or sodium salts.

It is recognized that compounds of the present invention may exist in various stereoisomeric forms. As such, the compounds of the present invention include diastereomers, enantiomers and atropisomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

According to an embodiment, the compound as defined above is of following formula (IVa) or (IVb):

(IVa)

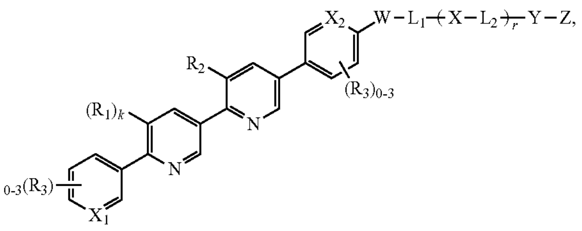

(IVb)

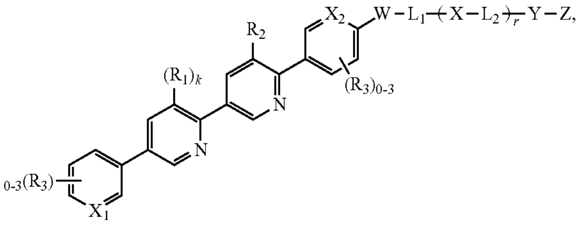

in particular of following formula (IVa1), (IVa2), (IVb1) or (IVb2):

(IVa1)

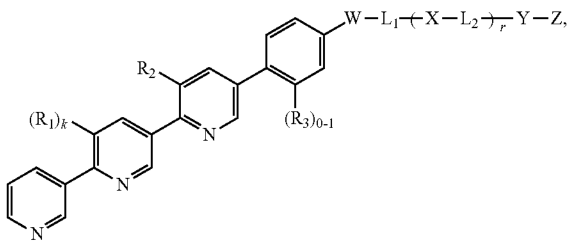

(IVa2)

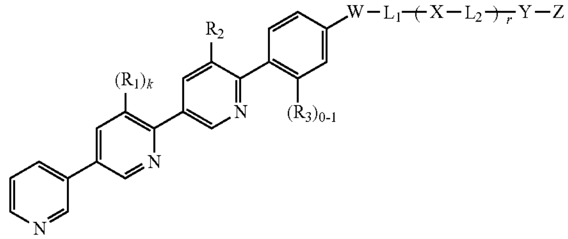

(IVb1)

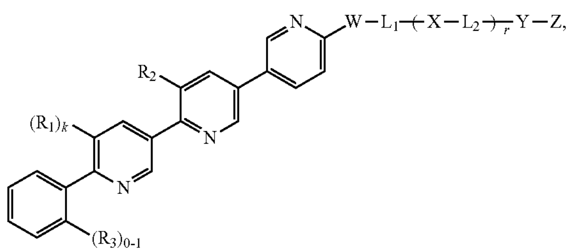

-continued (IVb2)

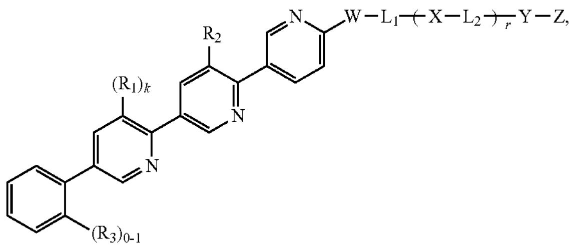

or of formula:

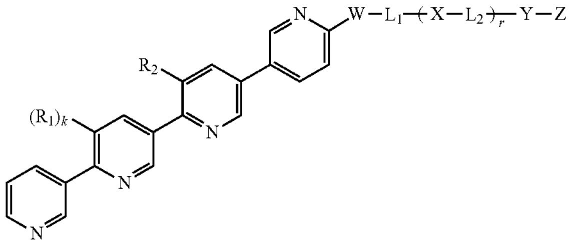

wherein:

$X_1$, $X_2$, are at each occurrence, independently selected from C or N;

$R_1$, $R_2$, $R_3$ are independently, at each occurrence, as defined above.

According to an embodiment, the compound as defined above is of one of the following formulae:

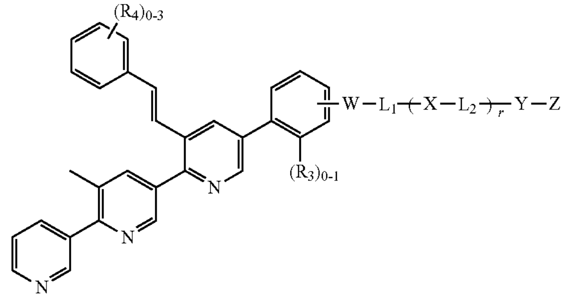

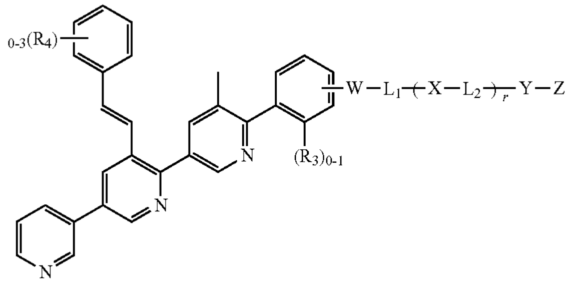

-continued
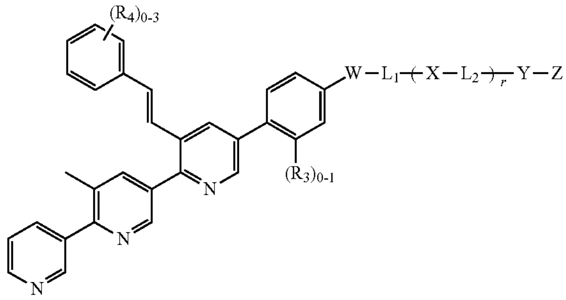
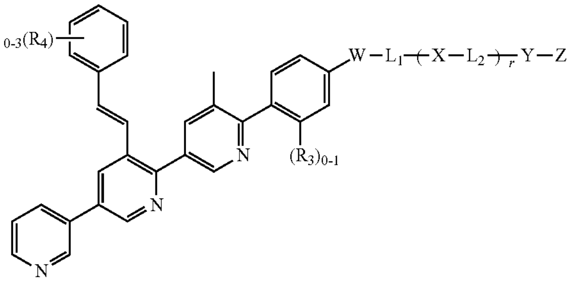
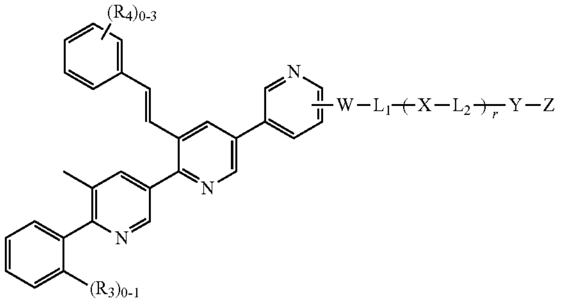
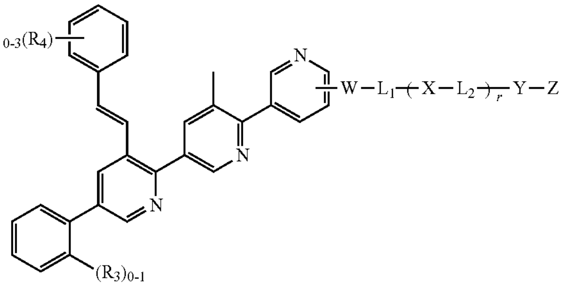
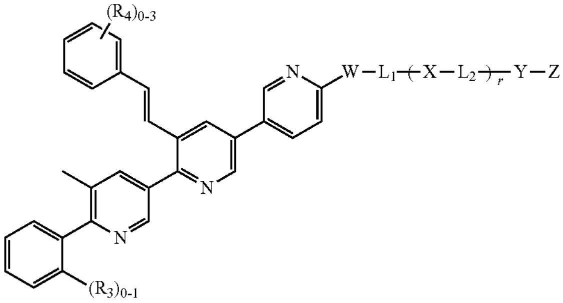
-continued
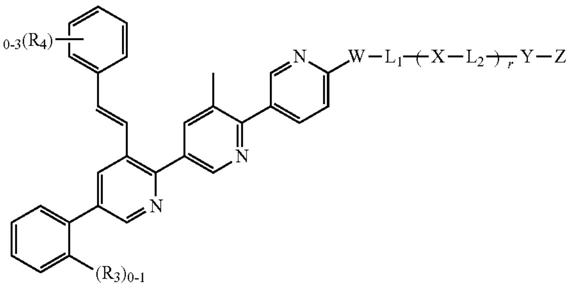
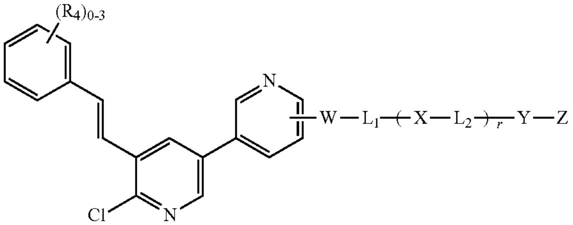
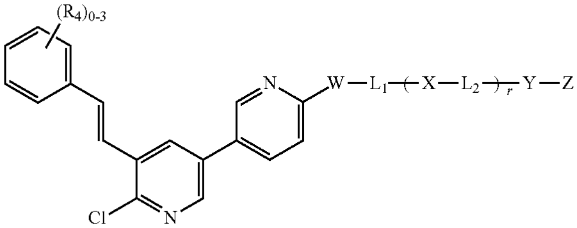
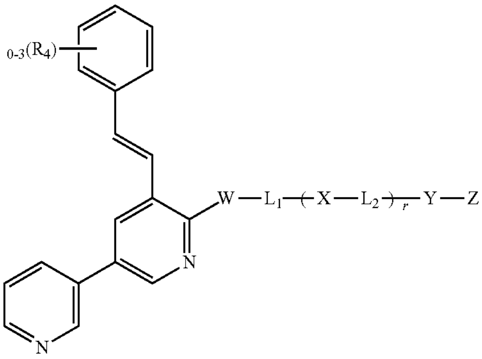
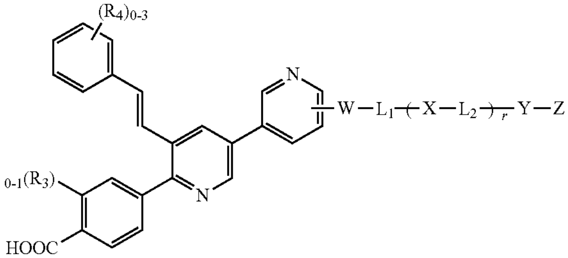
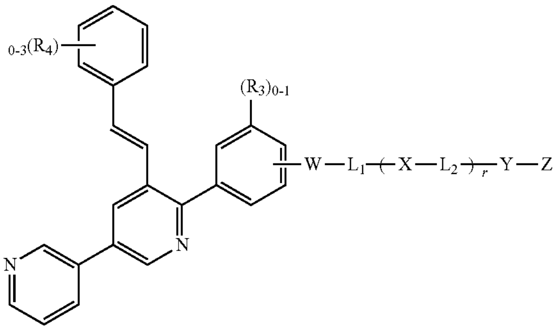

-continued

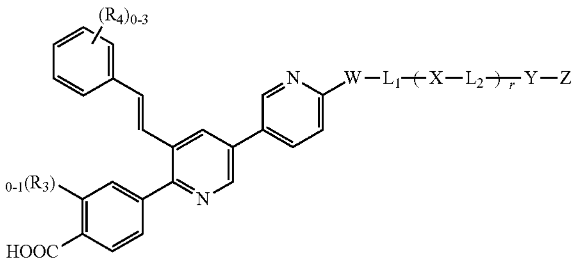

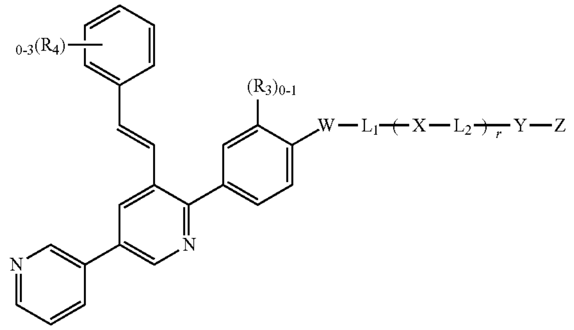

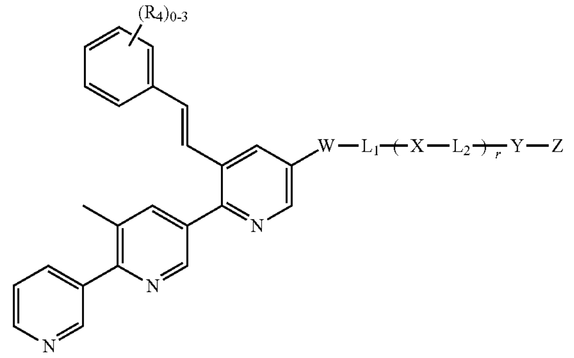

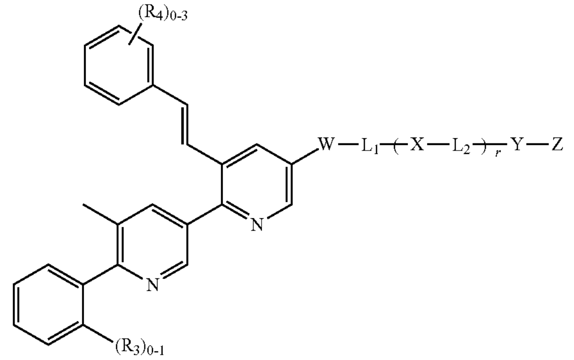

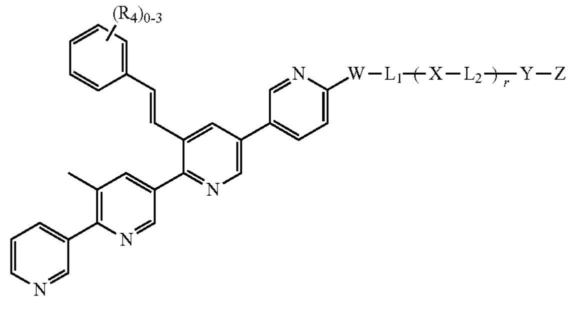

or a stereoisomeric form, a mixture of stereoisomeric forms and a pharmaceutically acceptable salt form thereof, in particular a sodium or fumarate salt, wherein:

$R_3$ and $R_4$ are independently, at each occurrence, as defined above.

According to an embodiment, W is —NH—, $L_1$ is $(C_1$-$C_{18})$alkyl, r is 1, X is a (5 to 7 membered) heteroaryl, in particular a triazole, $L_2$ is a $(C_1$-$C_{18})$alkyl interrupted by one or more —O— atoms, in particular of formula $—CH_2—(O—CH_2—CH_2)_{1-6}—$ and Y is a single bond, —NH— or —C(═O)NH—.

According to another embodiment, W is —NH—, $L_1$ is a $(C_1$-$C_{18})$alkyl interrupted by one or more —O— atoms, in particular of formula $—CH_2—CH_2—(O—CH_2—CH_2)_{1-6}—$, r is 0 and Y is a single bond or —C(═O)NH—.

According to another embodiment, W is —C≡C—, $L_1$ is a $(C_1$-$C_{18})$alkyl interrupted by one or more —O— atoms, in particular of formula $—CH_2—(O—CH_2—CH_2)_{1-6}—$, r is 0 and Y is a single bond or —C(═O)NH—.

According to an embodiment, Z is a VHL (von Hippel-Lindau), CRBN (cereblon), cIAP (Cellular Inhibitor of Apoptosis) or MDM2 (Mouse Double Minute 2) E3 ubiquitin ligase ligand, Z being in particular a VHL E3 ubiquitin ligase ligand.

According to a particular embodiment, Z is selected from:

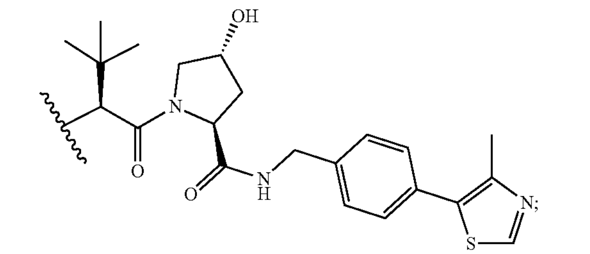

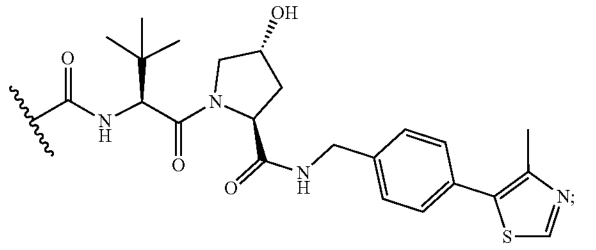

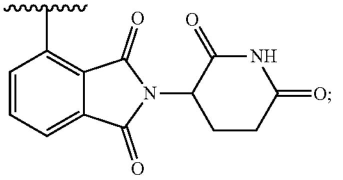

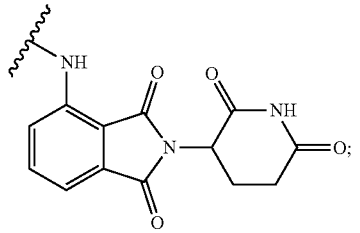

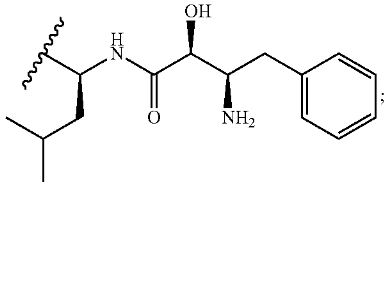

-continued
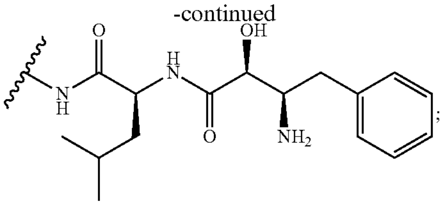
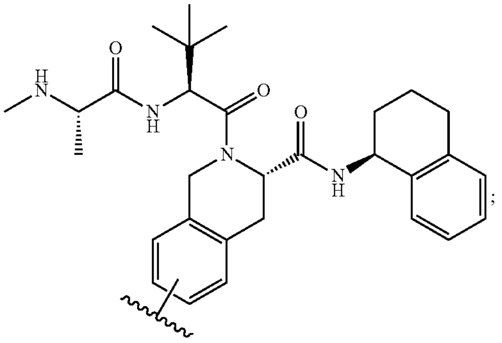
-continued
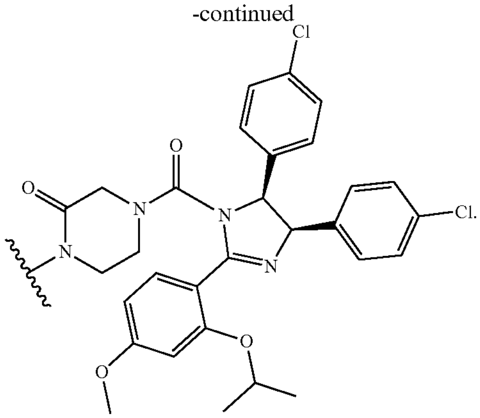
In still other aspects, there are included compounds of formula (I) which are selected from:
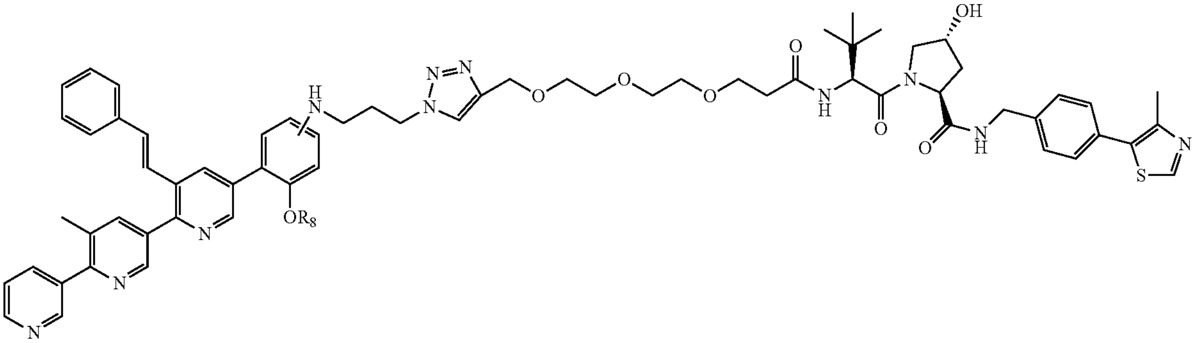
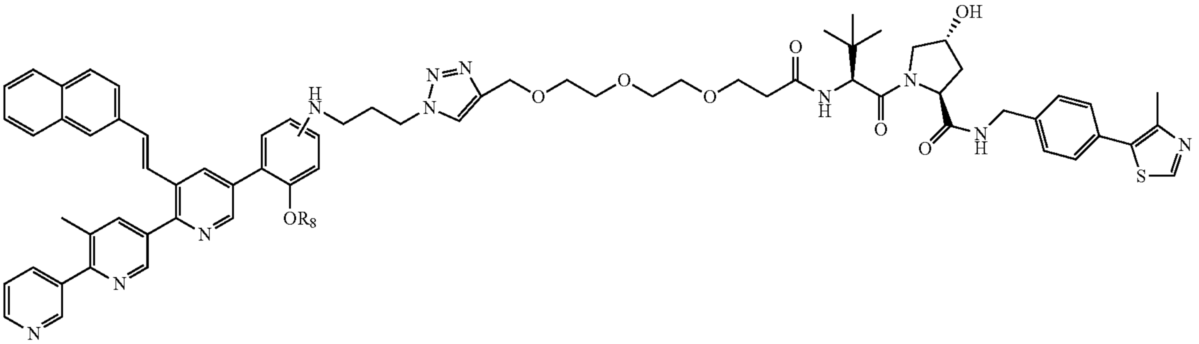
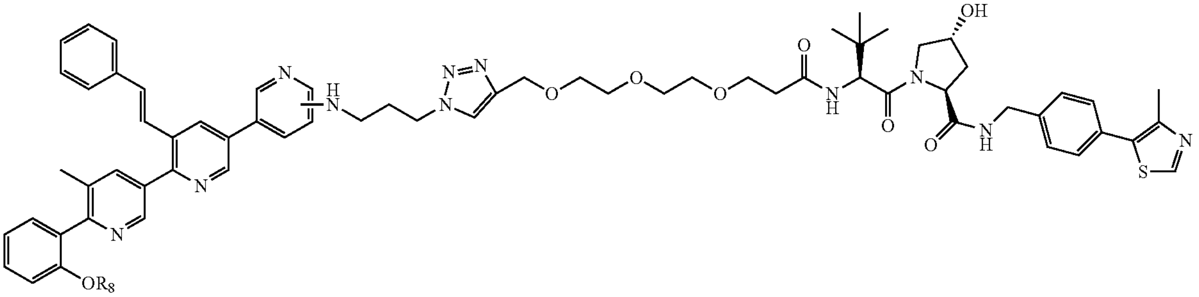

-continued
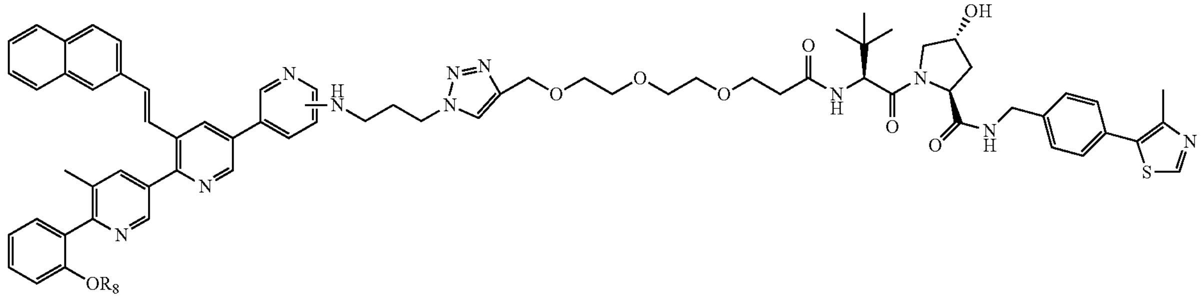
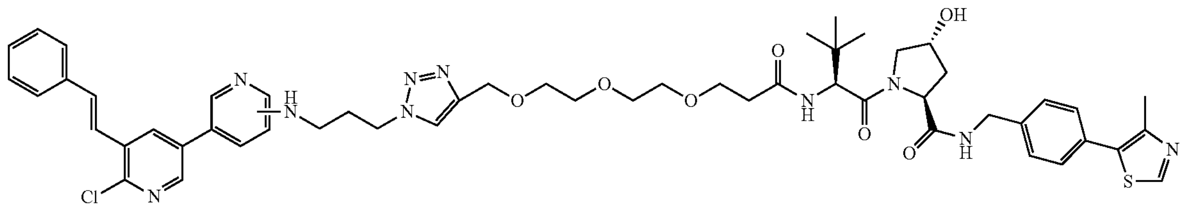
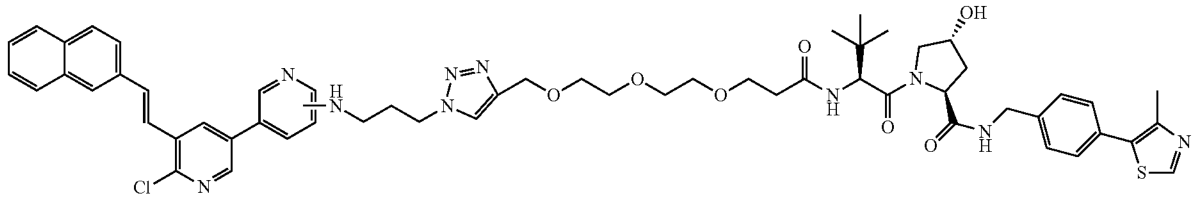
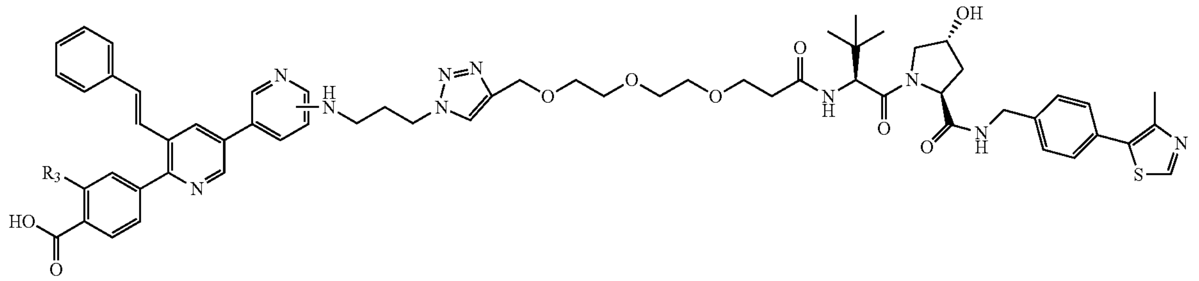
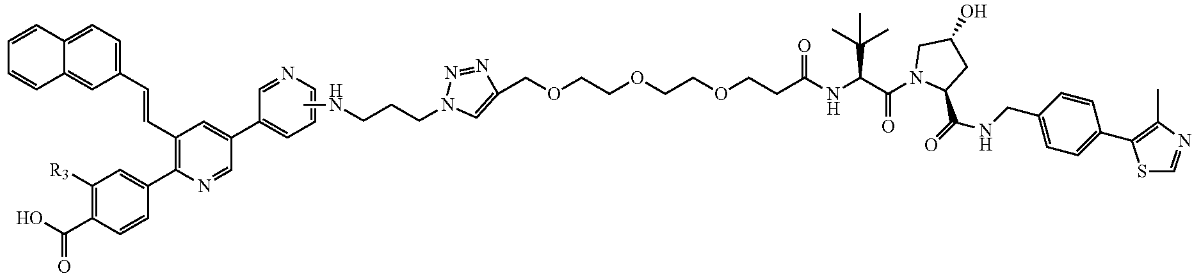
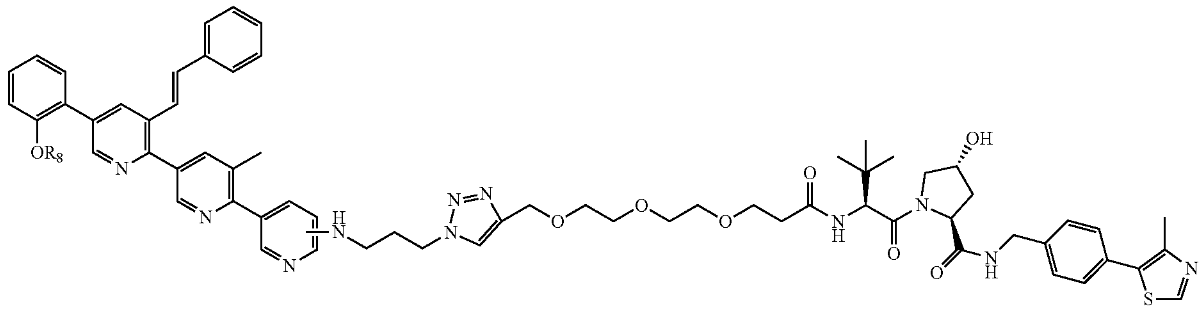

-continued
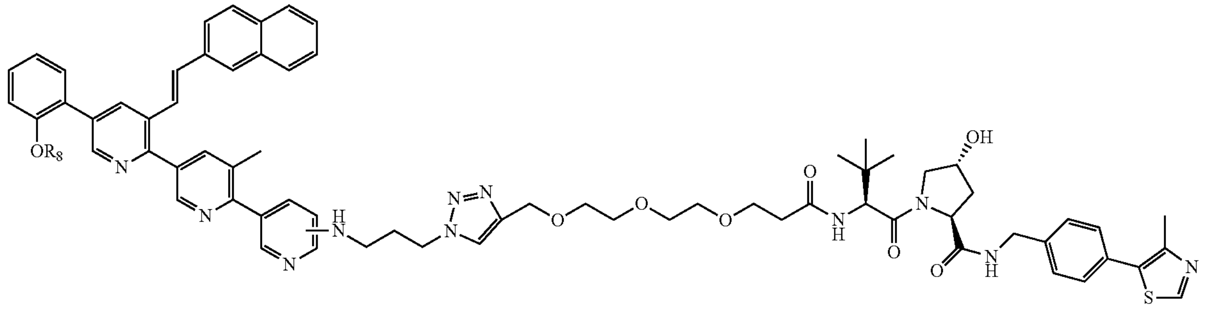
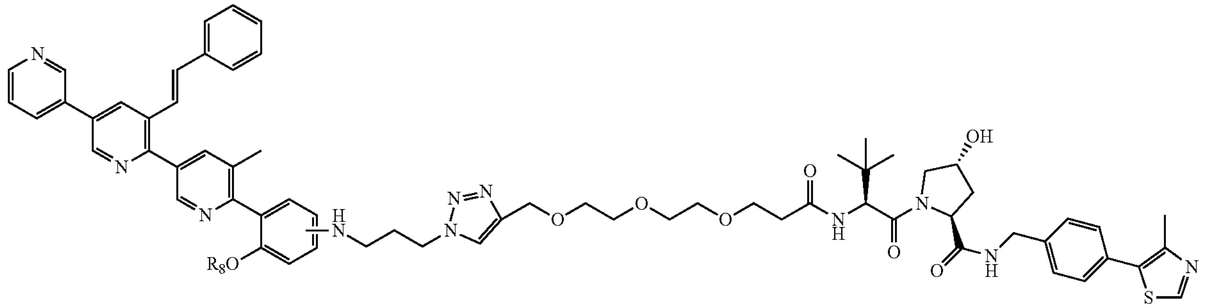
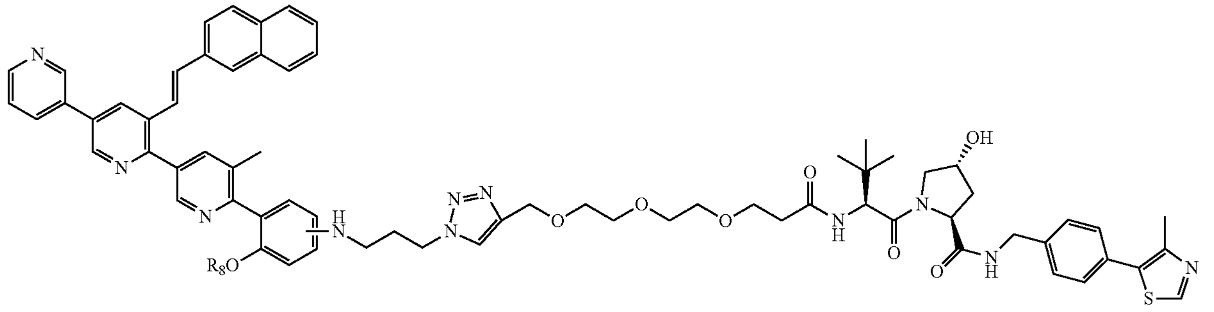
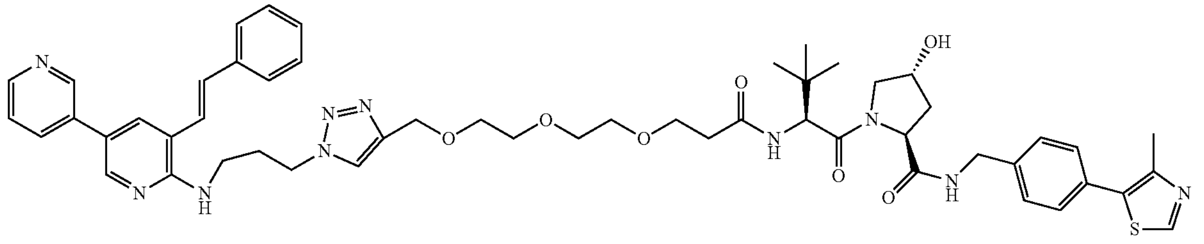
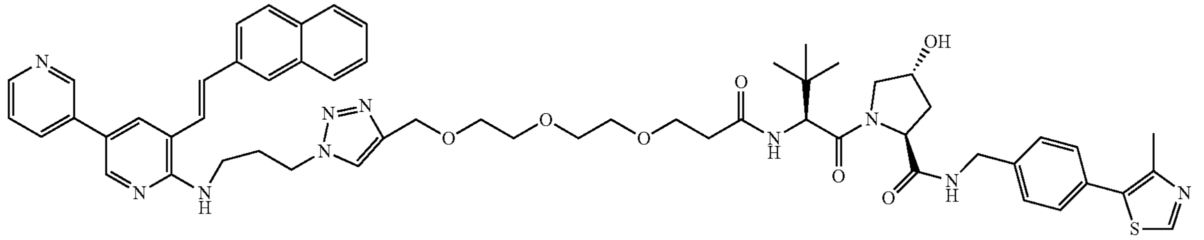
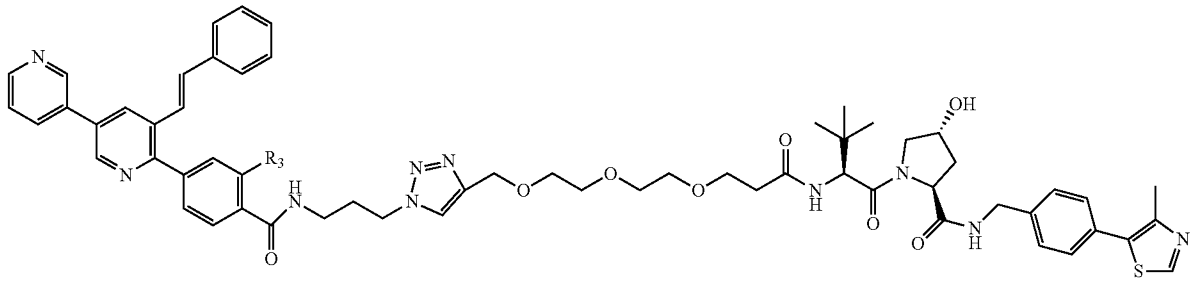

-continued
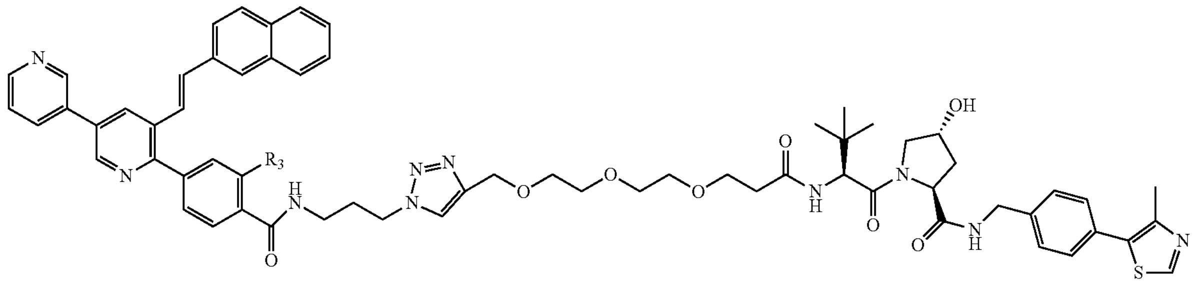
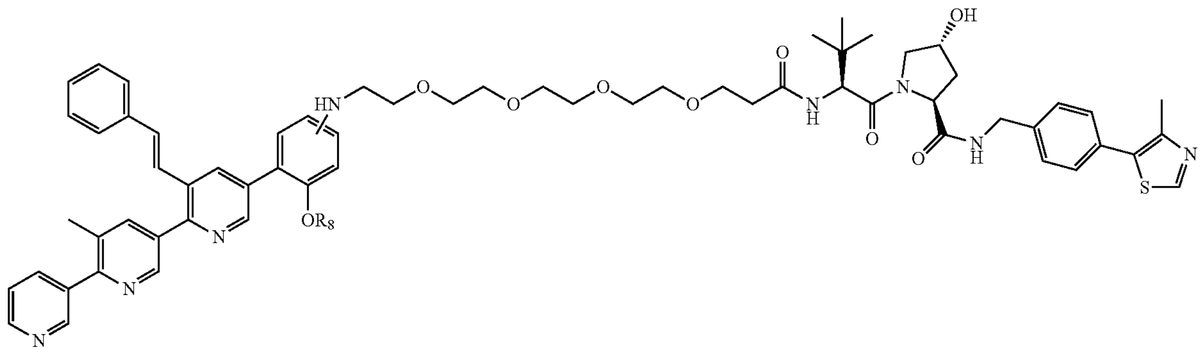
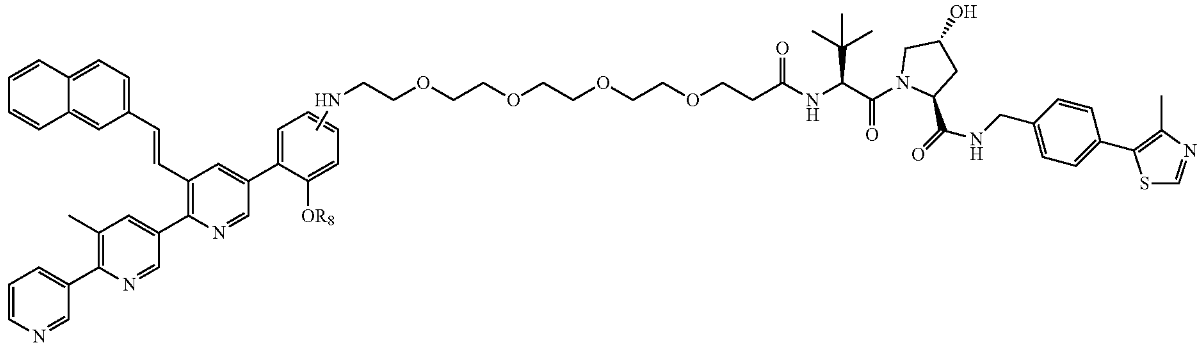
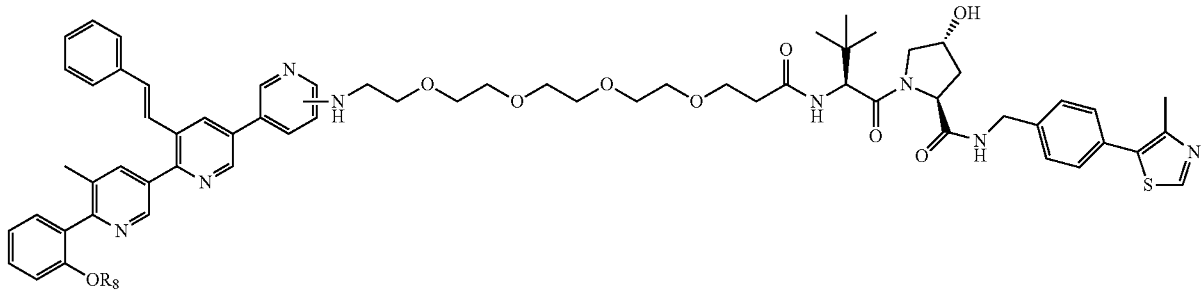
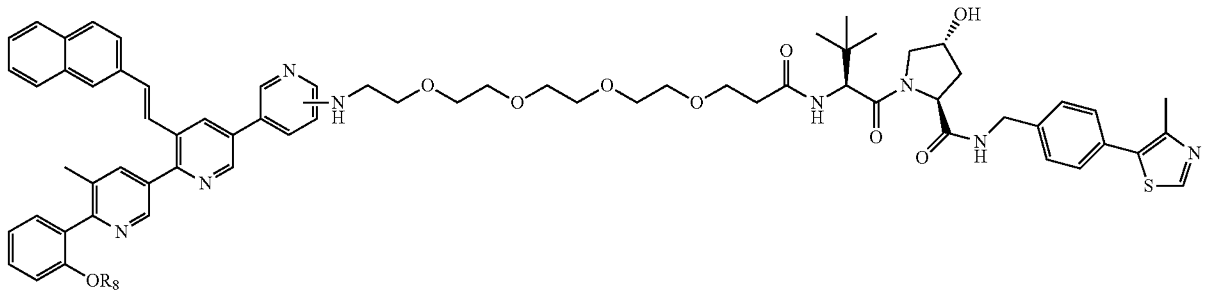

-continued
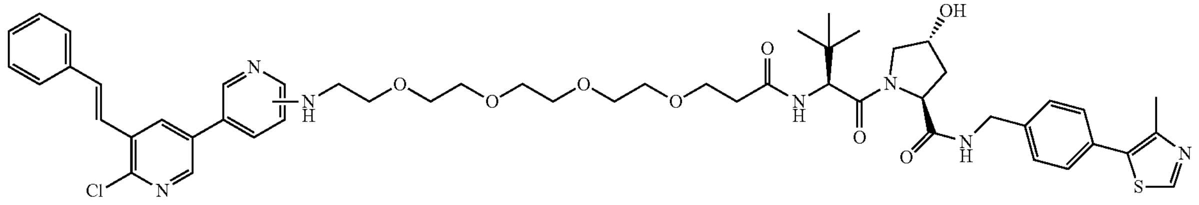
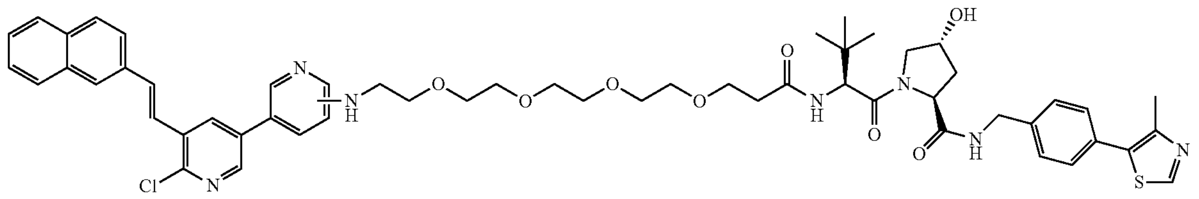
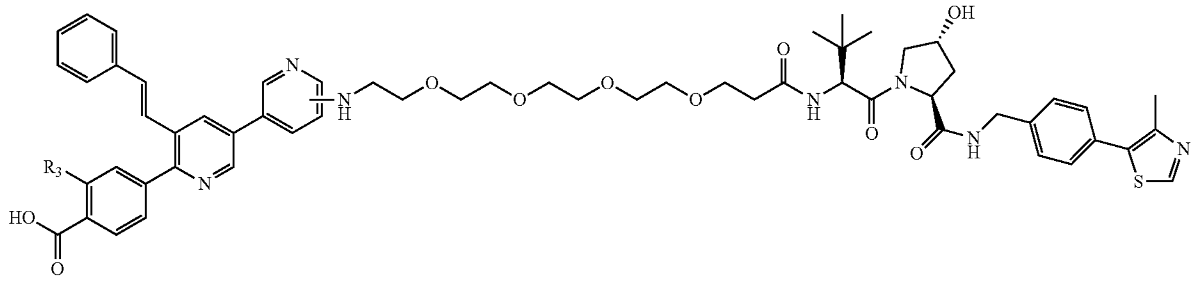
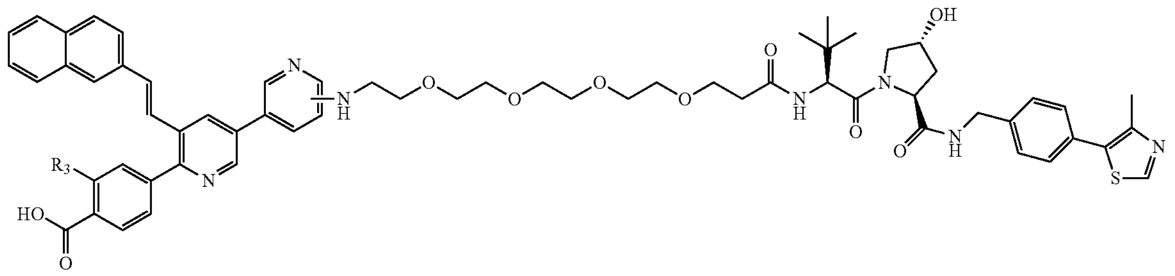
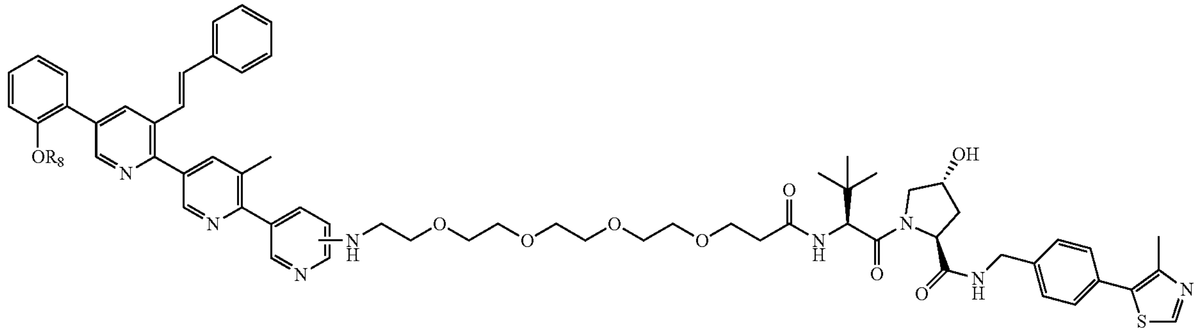
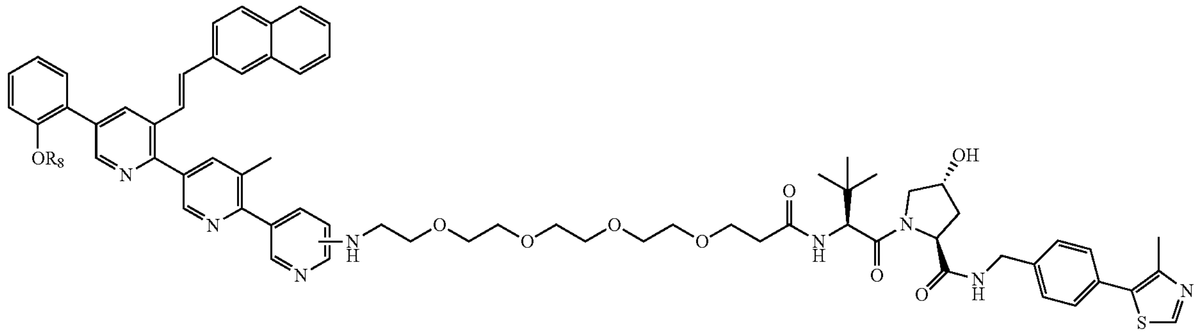

-continued
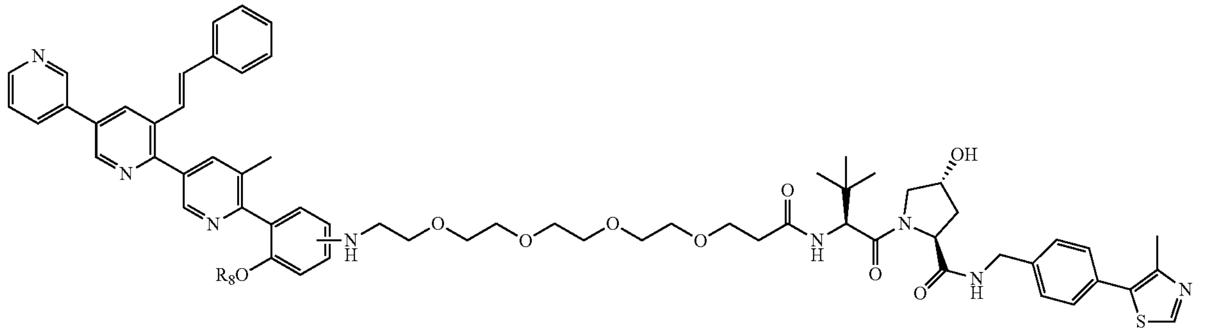
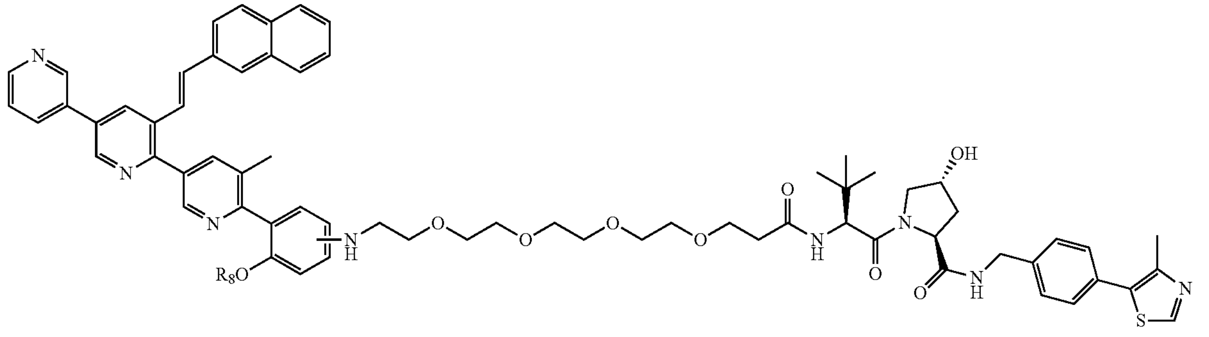
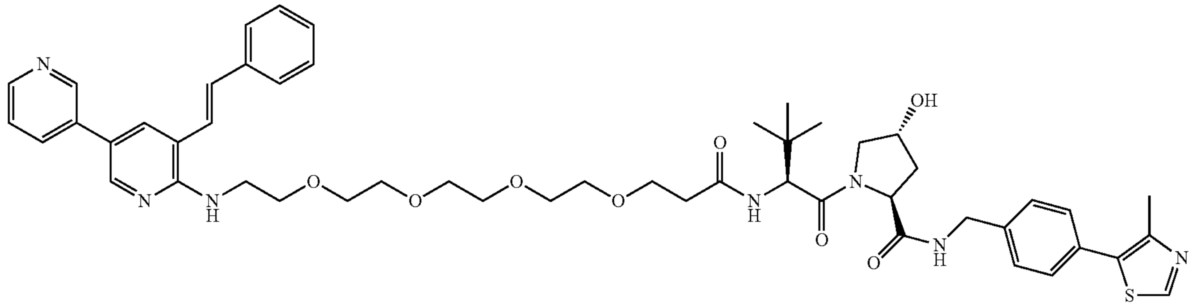
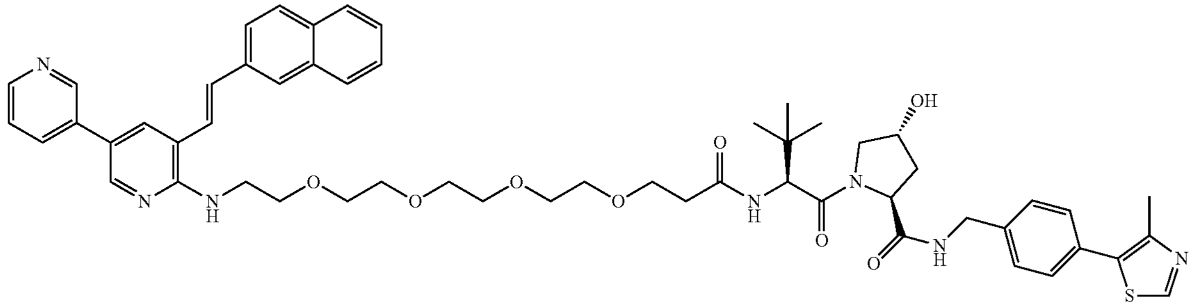
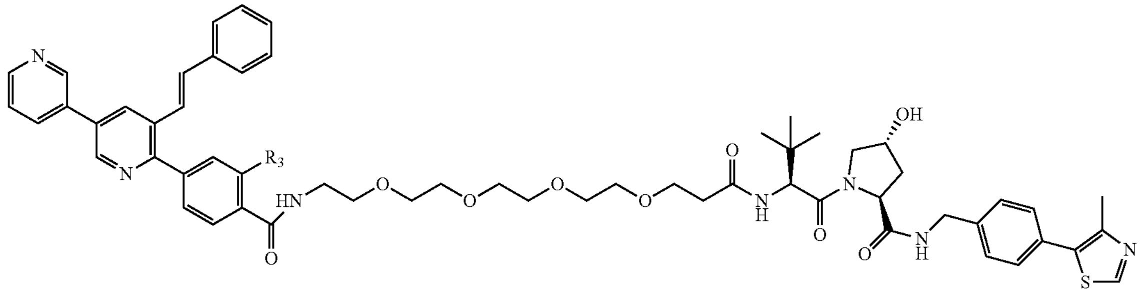

-continued
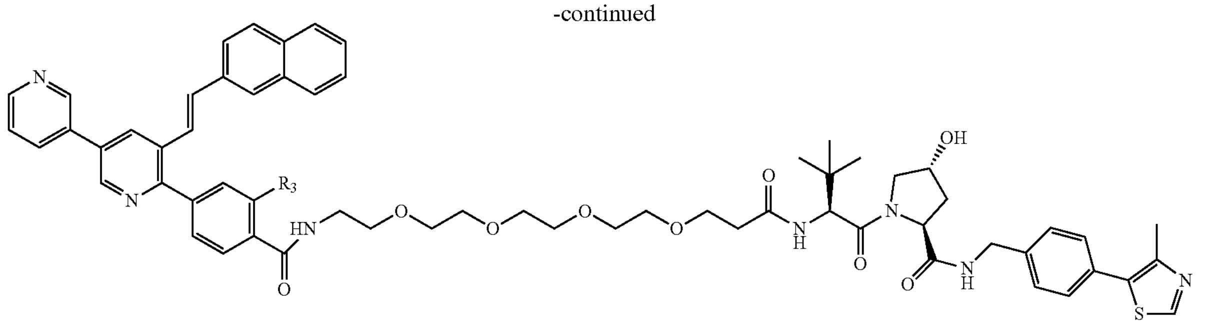
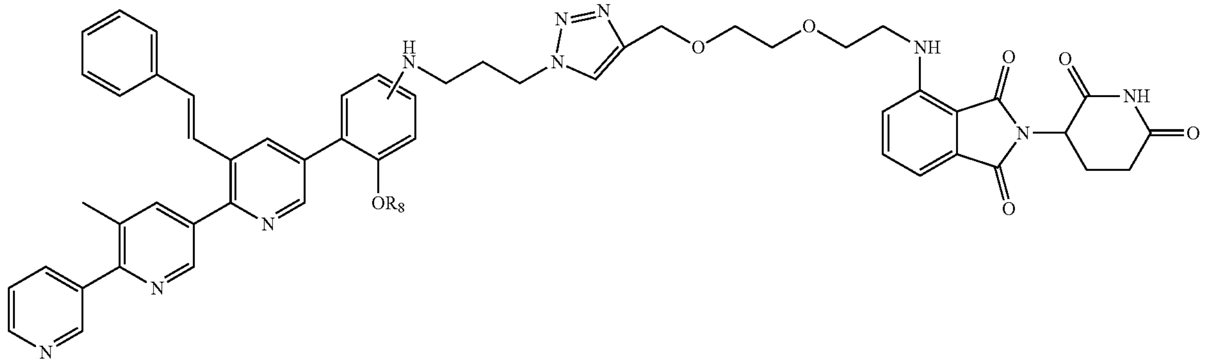
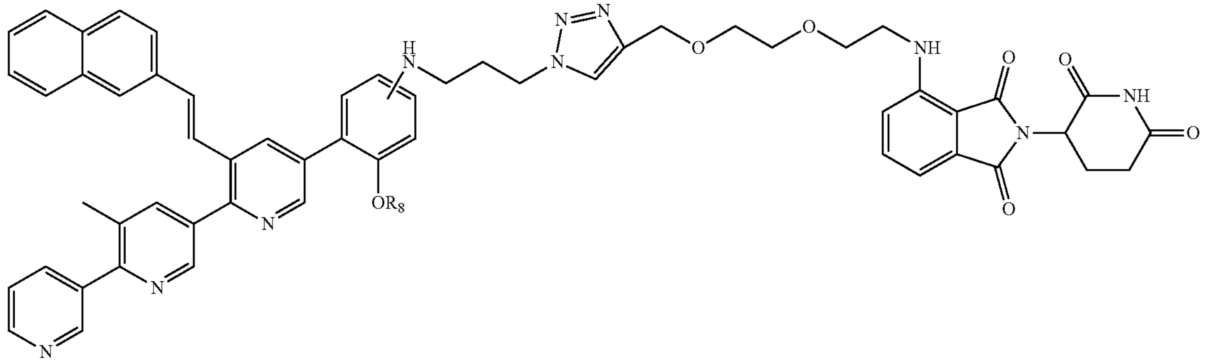
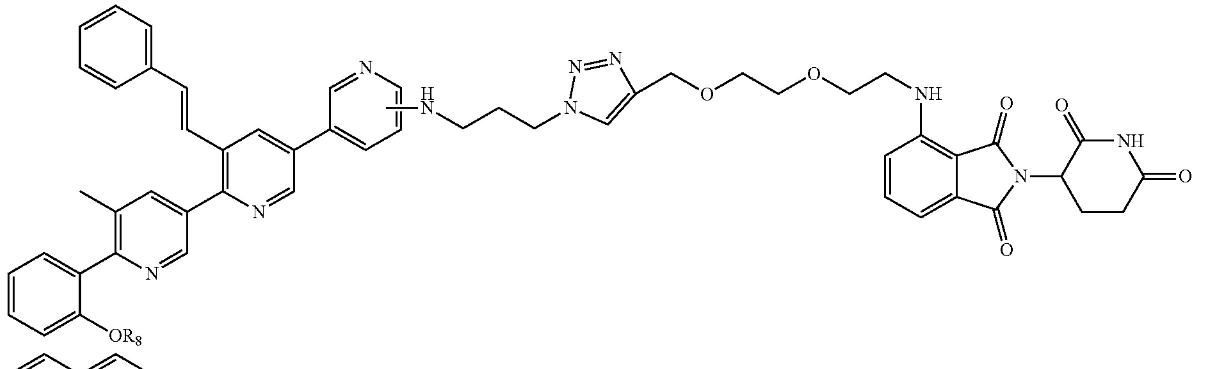
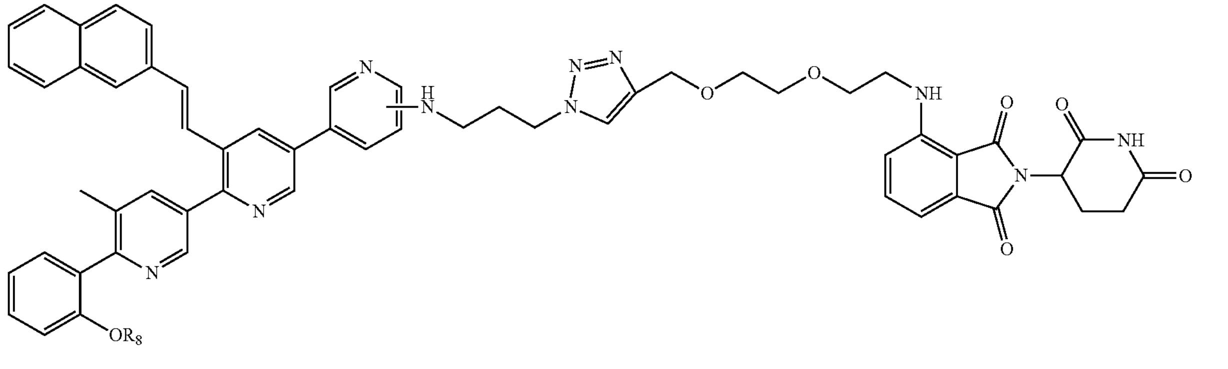

-continued
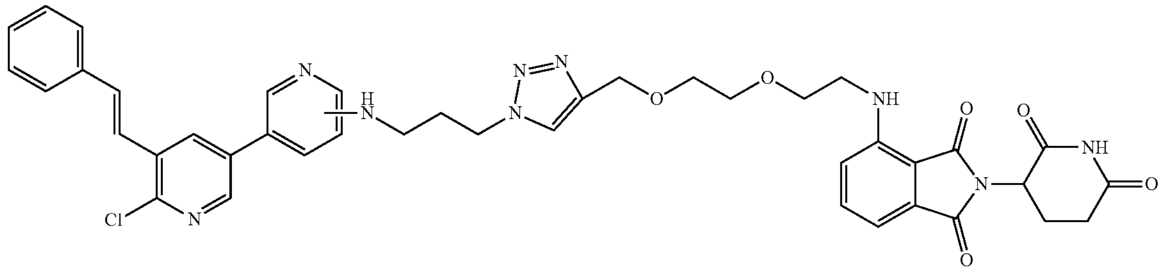
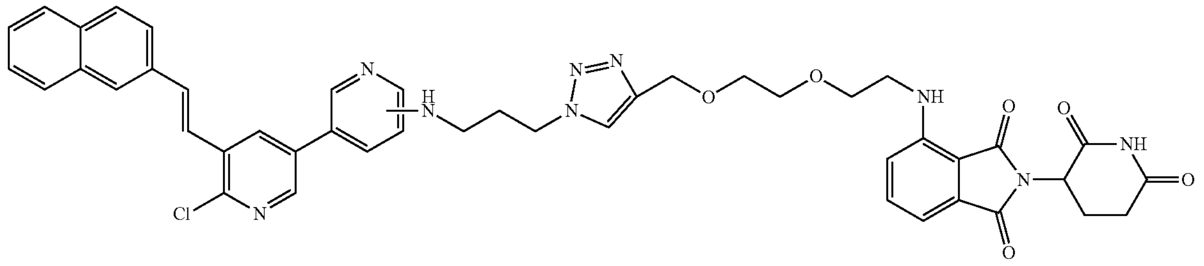
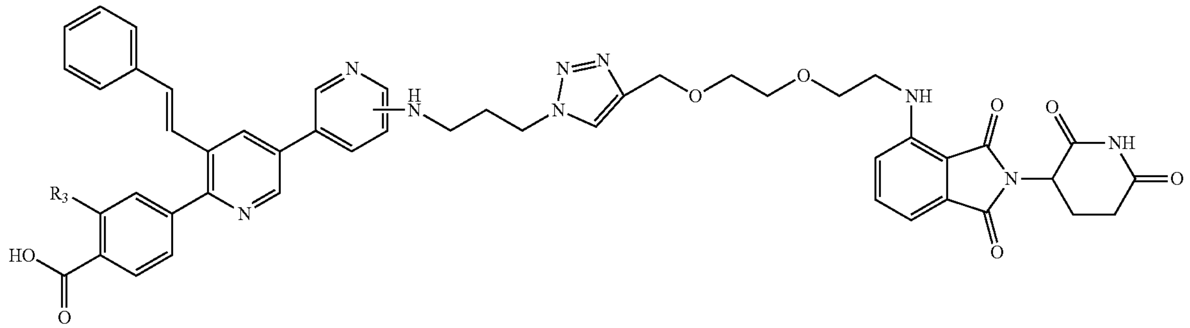
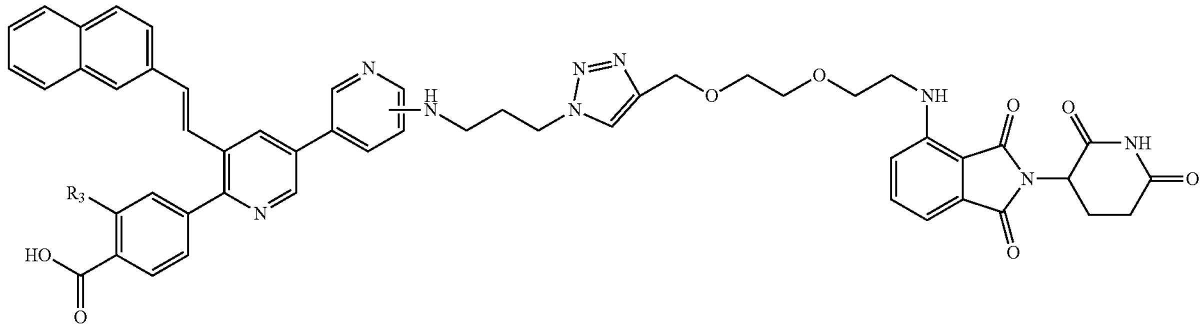
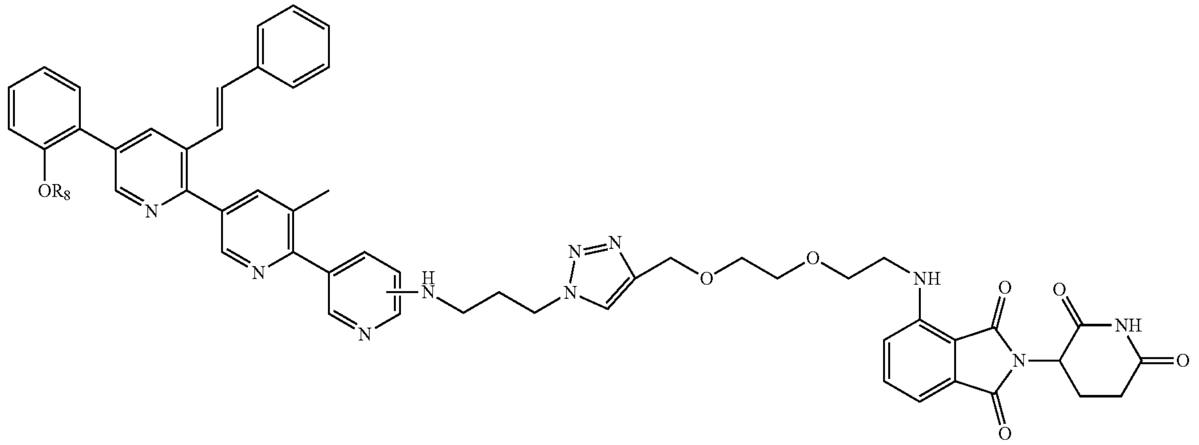

-continued
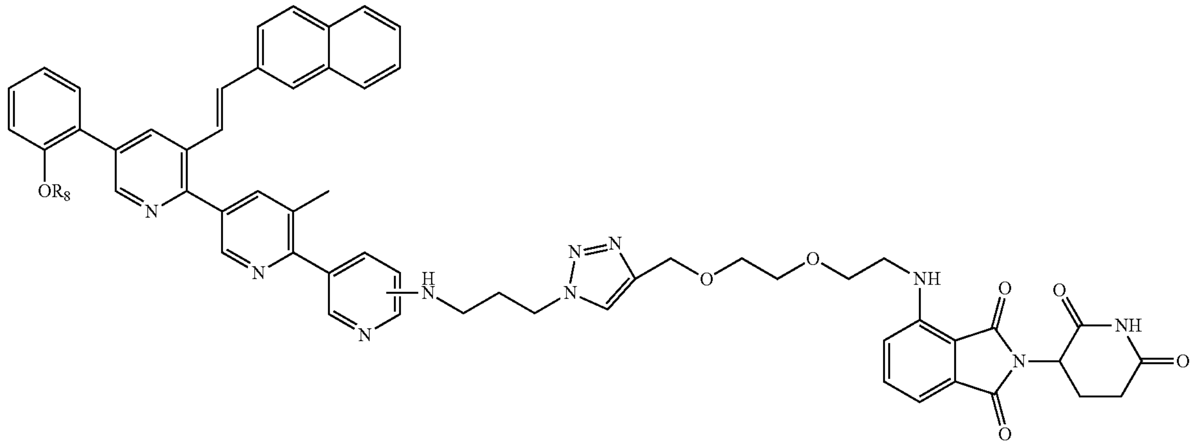
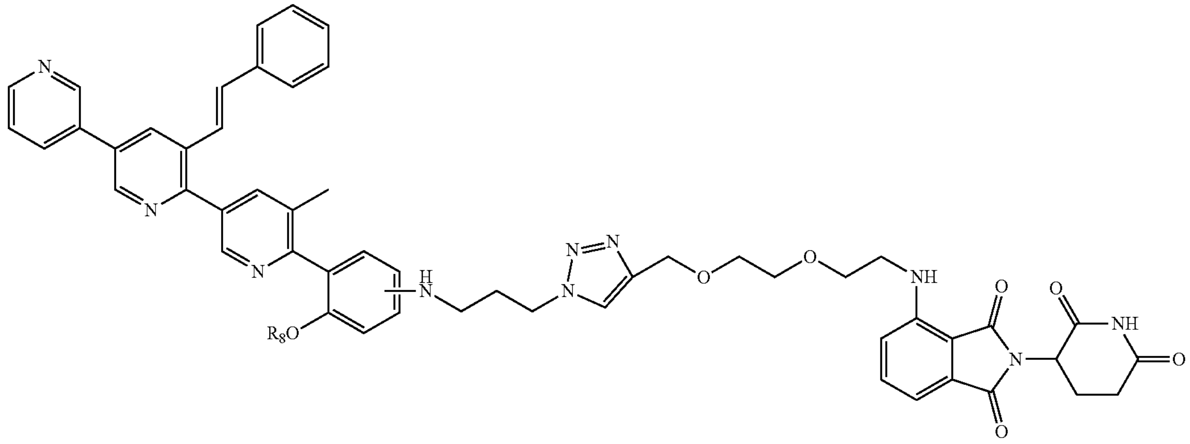
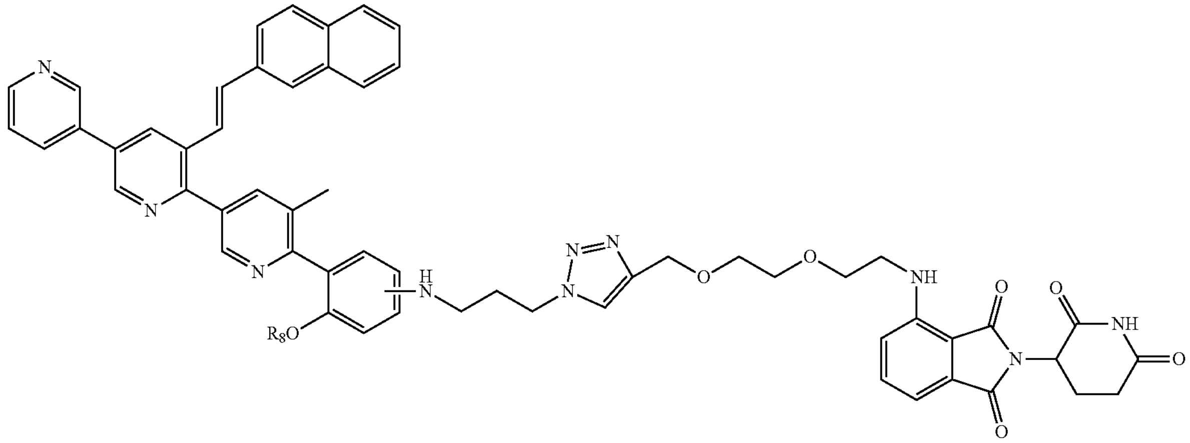
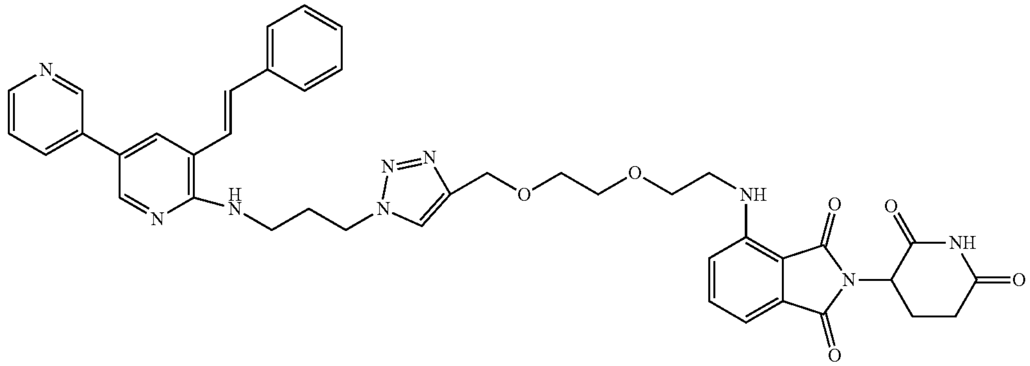

-continued
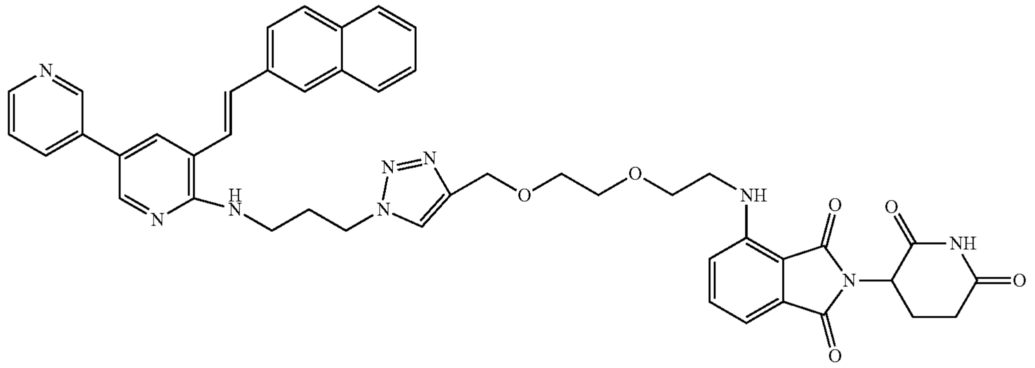
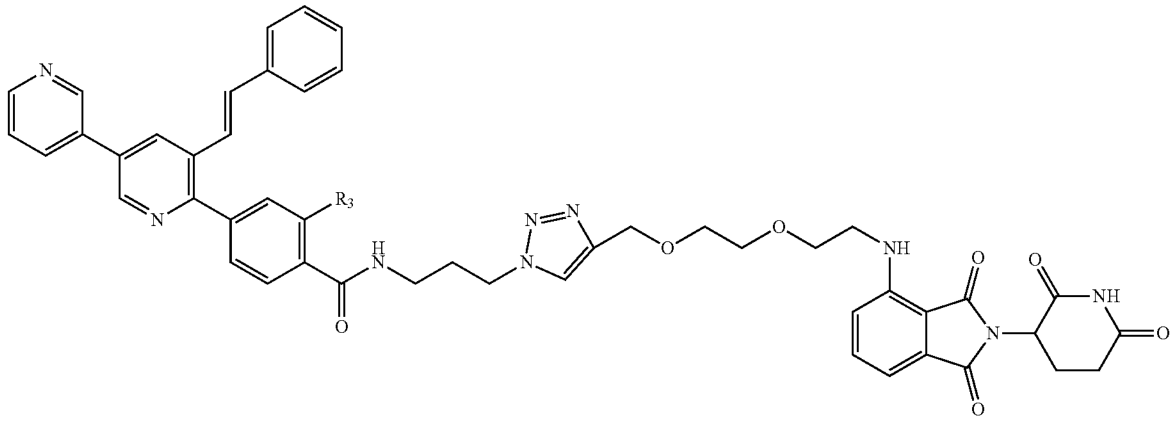
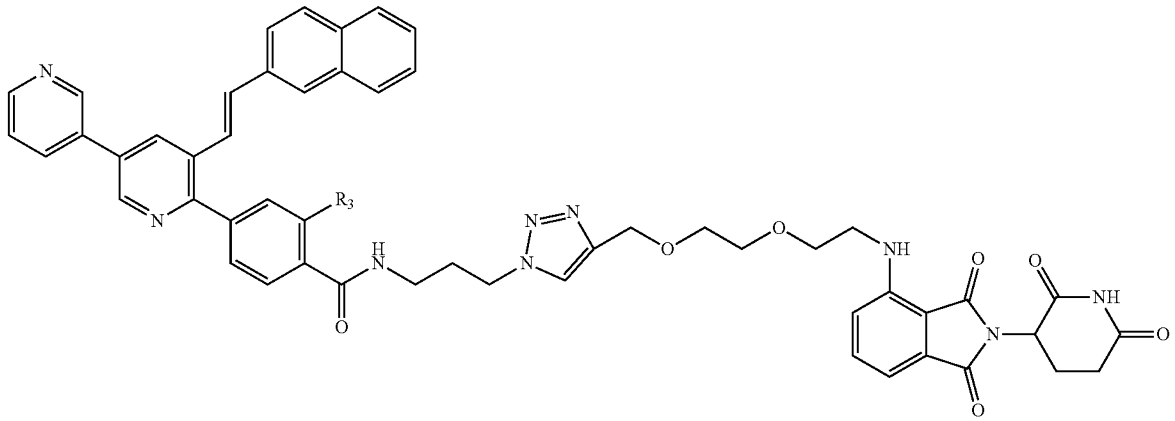
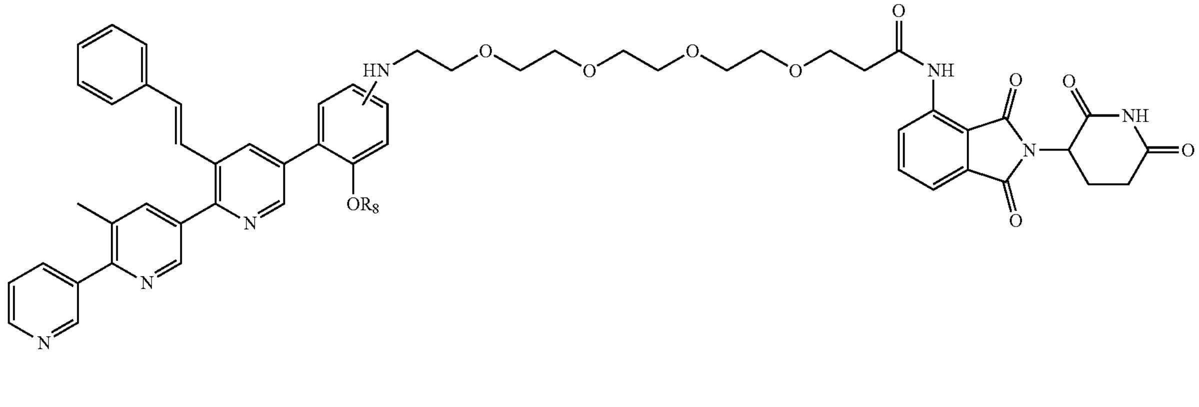

-continued
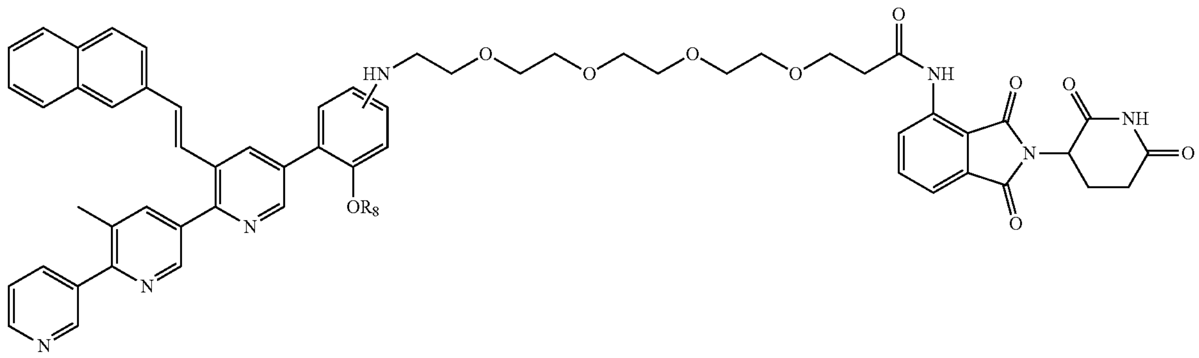
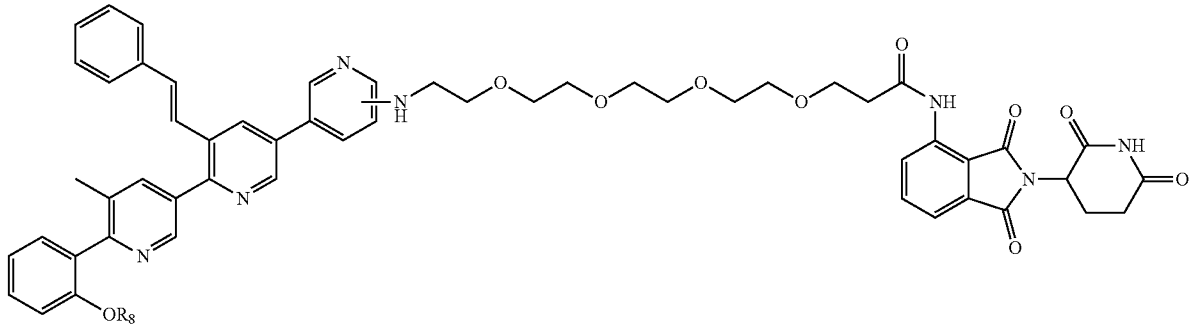
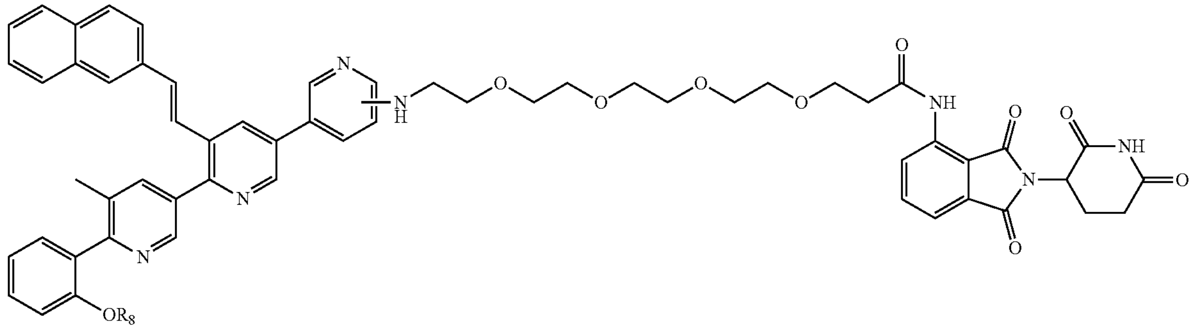
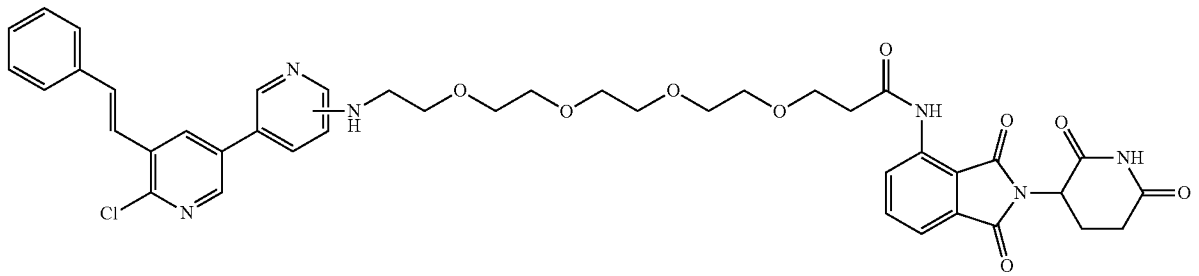
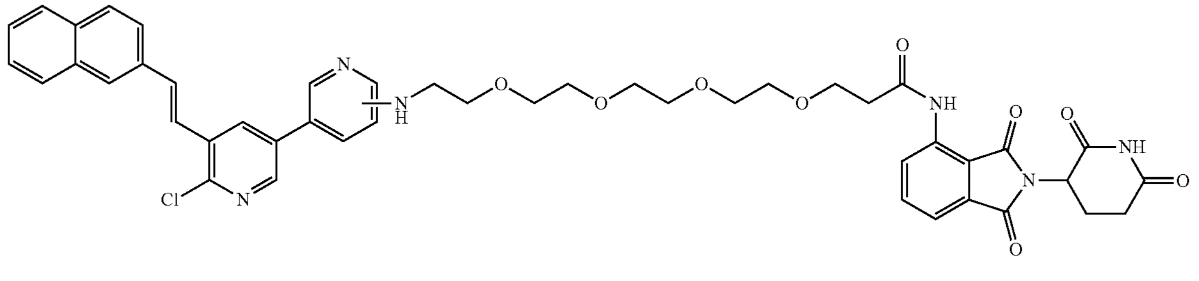

-continued
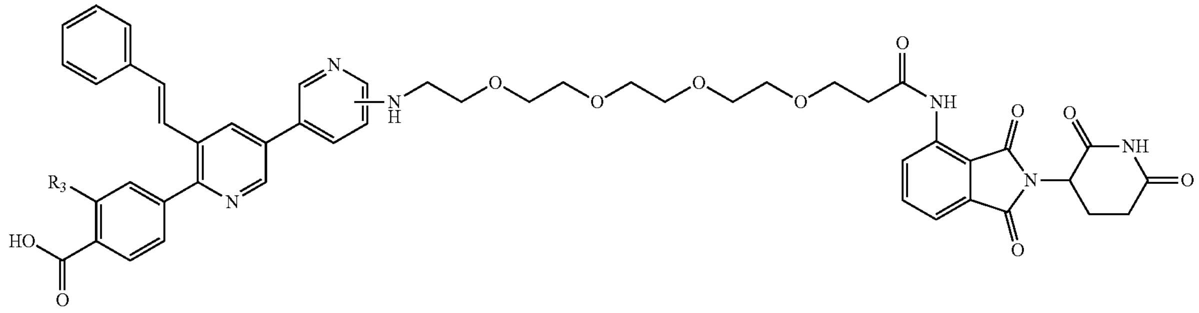
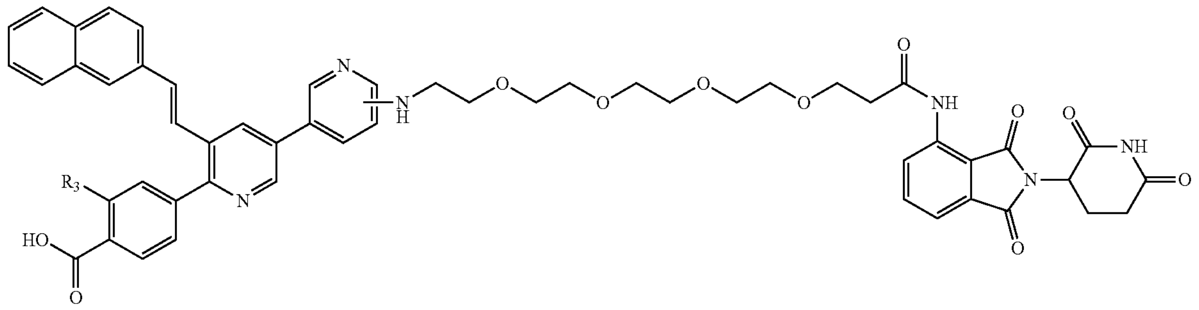
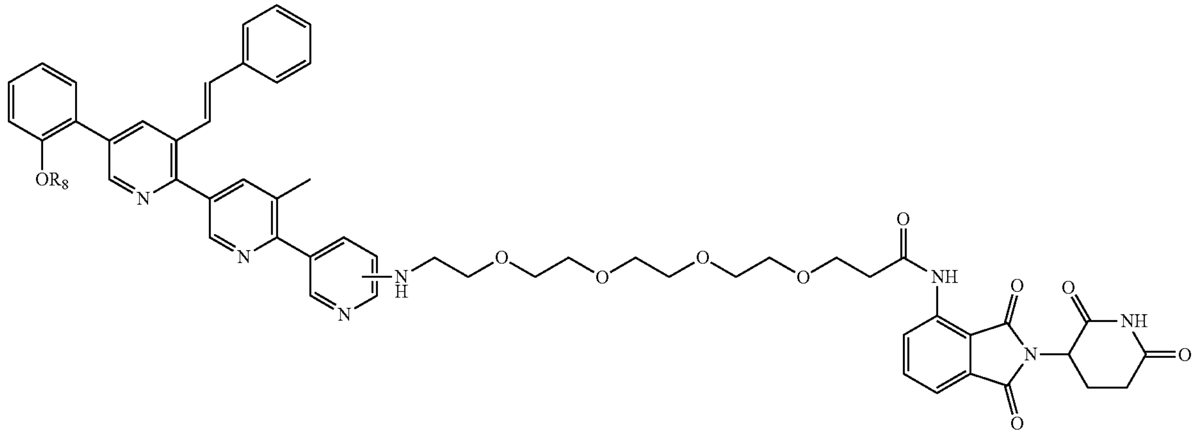
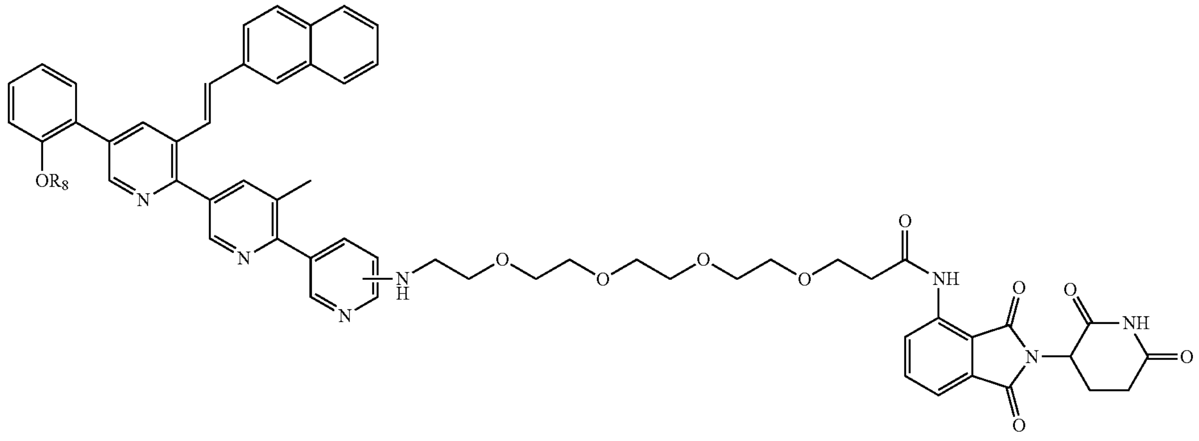

-continued
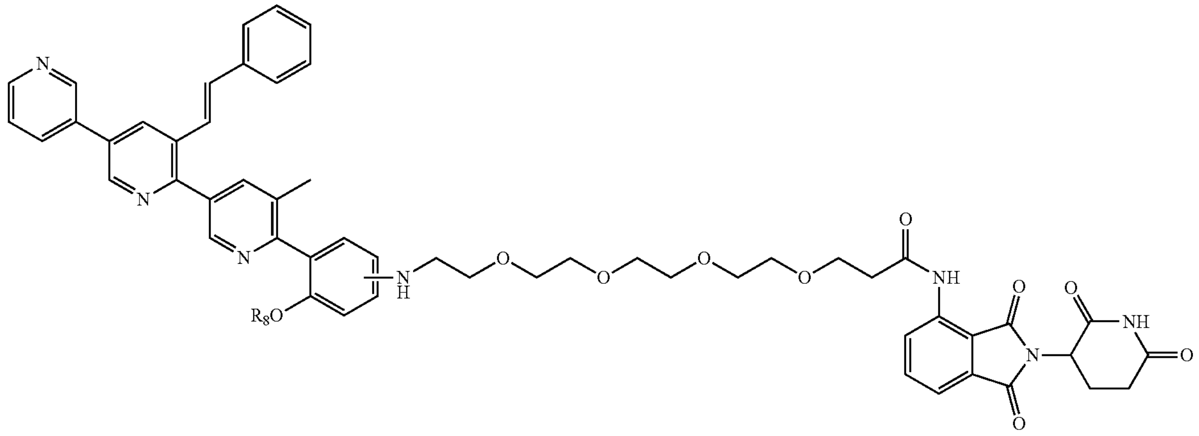
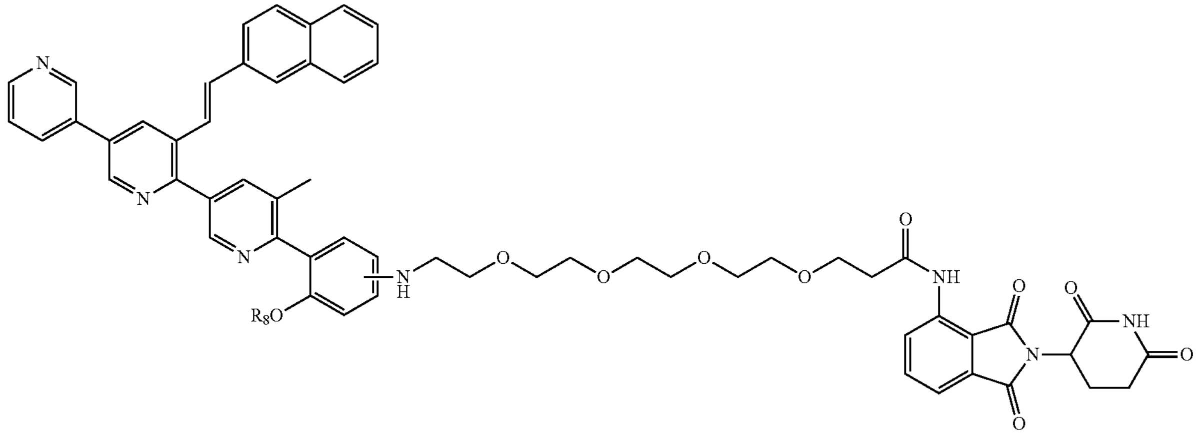
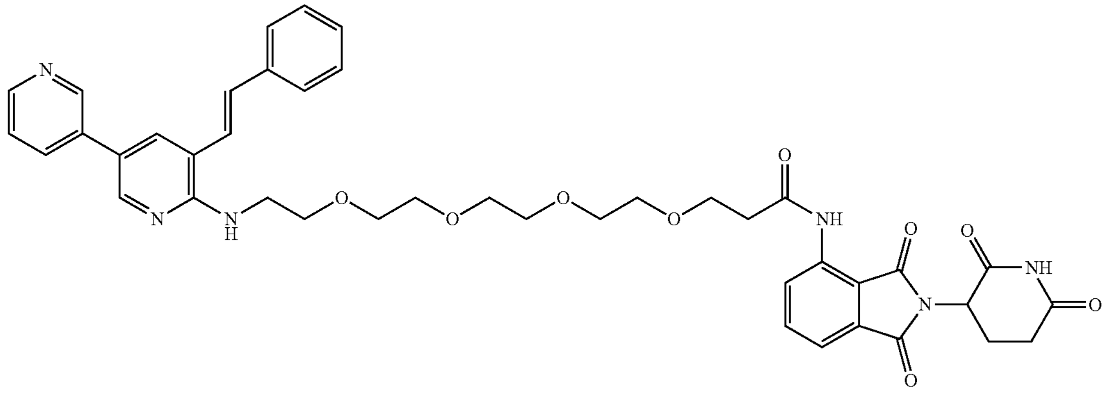
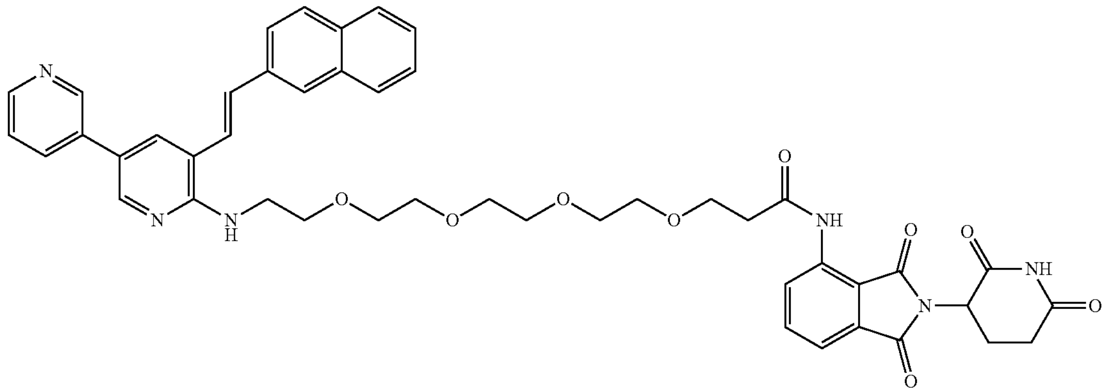

-continued
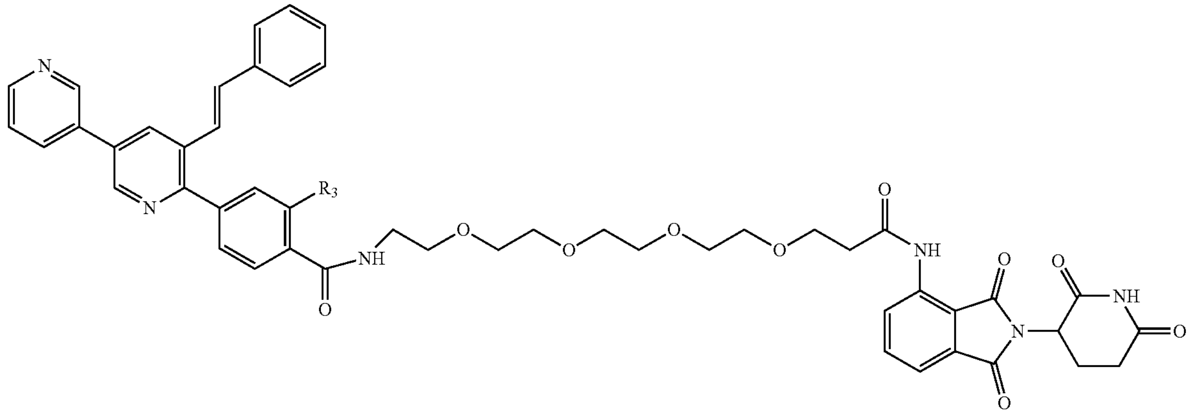
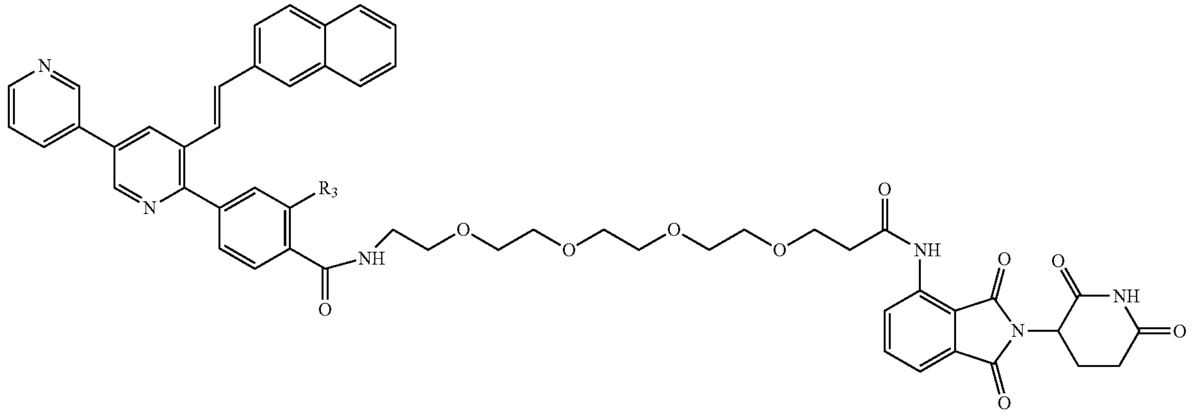
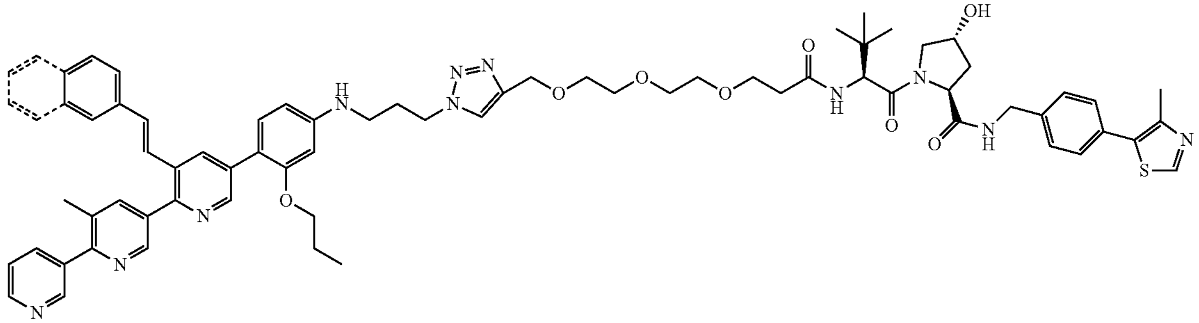
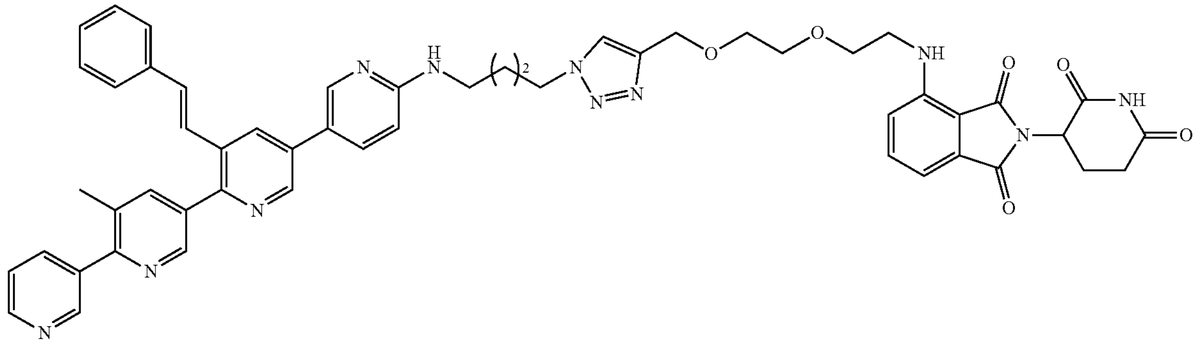

-continued

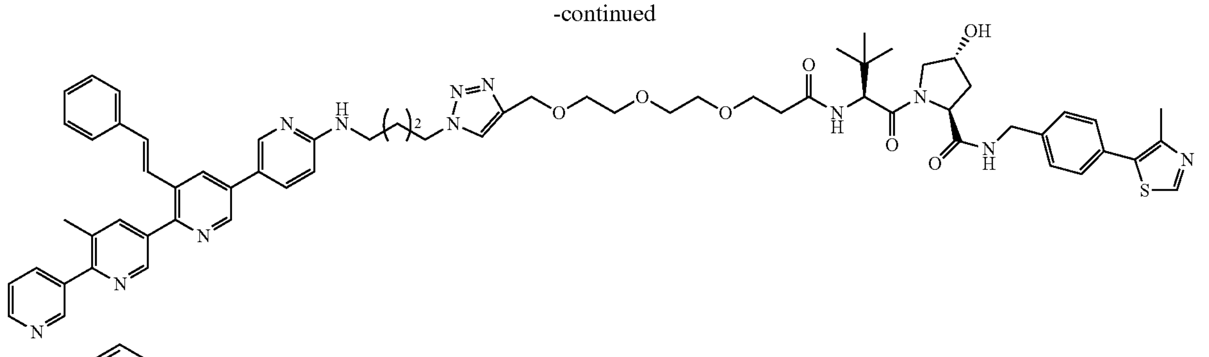

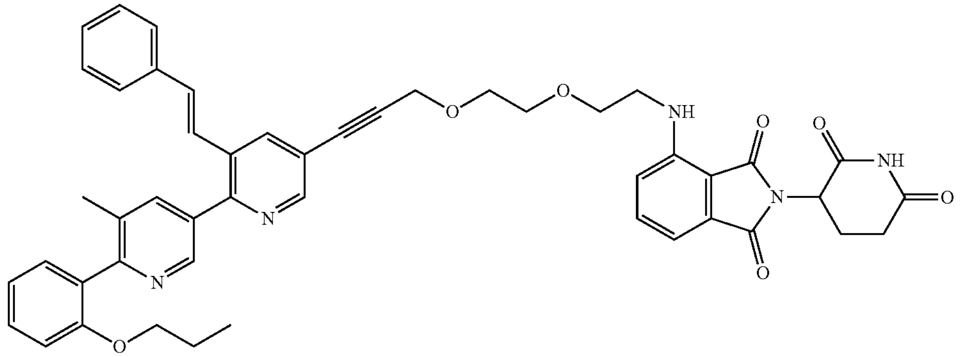

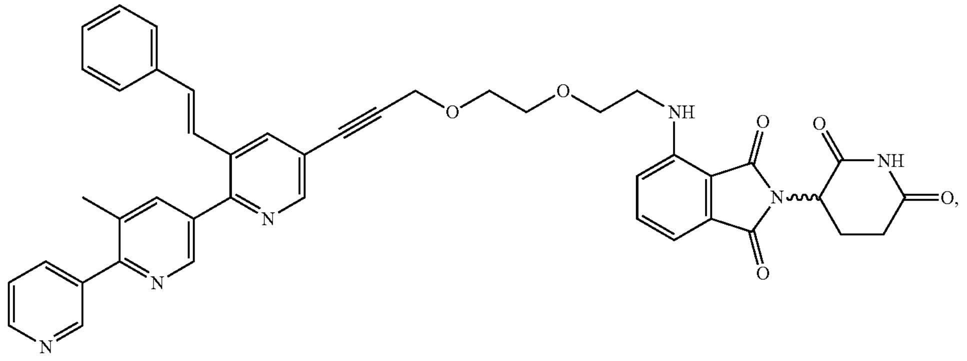

Wherein:

$R_3$ is H or as defined above, in particular Cl;

$R_8$ is ($C_1$-$C_6$)alkyl, in particular propyl.

Method of Preparation of Compounds of Formula (I)

The compounds of the present invention may be prepared in a number of methods well known to those skilled in the art, including, but not limited to those described below, or through modifications of these methods by applying standard techniques known to those skilled in the art of organic synthesis. The reagents and starting materials are commercially available, or readily synthesized by well-known techniques by one of ordinary skill in the arts. All substituents, unless otherwise indicated, are as previously defined. All processes disclosed in association with the present invention are contemplated to be practiced on any scale, including milligram, gram, multigram, or commercial industrial scale.

As will be readily understood, functional groups present on the compounds of Formula I may contain protecting groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention.

Other preferred protecting groups according to the invention may be found in Greene, T. W. and Wuts, P. G. M., "Protective Groups in Organic Synthesis" 2d. Ed., Wiley & Sons, 1991, or in P. J. Kocienski, "Protecting Groups", $3^{rd}$. Ed., Thieme, Stuttgart, NY, 2004.

The compound thus prepared may be recovered from the reaction mixture by conventional means. For example, the compounds may be distilled off from the solvent mixture after the extraction or, if necessary after distilling off from the solvent mixture, pouring the residue into water followed by extraction with a water-immiscible organic solvent and distilling off from the solvent mixture. Additionally, the product can, if desired, be further purified by various well known techniques, such as recrystallization, precipitation or the various chromatography techniques, notably column chromatography or preparative thin layer chromatography, in particular High Performance Liquid Chromatography (HPLC).

In another object, the present invention relates to a method for preparing a compound of formula (I) as defined herein, wherein r is 1, comprising the steps of:

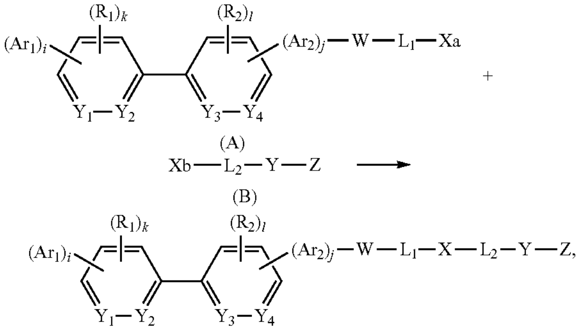

(A) (B) (I)

wherein Xa and Xb are chemical groups that form after chemical reaction the group X as defined above.

Xa and Xb are well known from the skilled person in the art and are for example —$N_3$ and -≡(alkynyl) respectively, forming a triazole by copper(I)-catalyzed azide-alkyne Huisgen cycloaddition.

Compound (B) is commercially available, as described below, or may be obtained as follows:

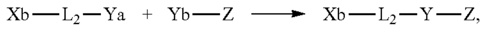

(B1) (B2) (B)

wherein Ya and Yb are chemical groups that form after chemical reaction the group Y as defined above.

Ya and Yb are well known from the skilled person in the art and are for example —COOH or an activated ester and —$NH_2$ respectively, forming —CONH— by peptidic coupling, or —$NH_2$ and —F (—F being in particular bound to an aromatic group), forming —NH— by nucleophilic aromatic substitution.

Compounds (B1) and (B2) are commercially available, as described below or obtained by procedures well known from those skilled in the art.

In an embodiment, compound (A) is obtained as follows:

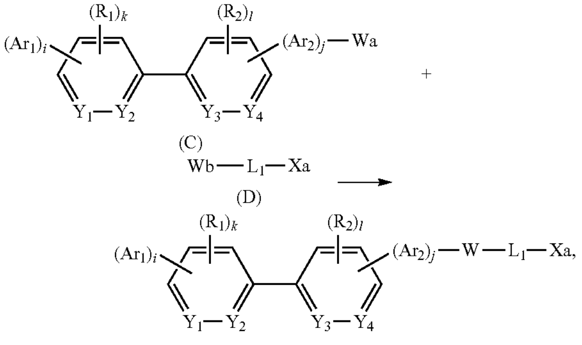

(C) (D) (A)

wherein Wa and Wb are chemical groups that form after chemical reaction the group W as defined above.

Wa and Wb are well known from the skilled person in the art and are for example —F or —Cl and —$NH_2$ respectively, forming —NH— by nucleophilic aromatic substitution, or —COOH or an activated ester and —$NH_2$ respectively, forming —CONH— by peptidic coupling.

D is commercially available or obtained by procedures well known from those skilled in the art.

In an embodiment, compound (C) is obtained as follows, $Ar_1$ being in particular selected from $(C_6-C_{10})$aryl and (5 to 7 membered) heteroaryl when j is 1, and i is 0 or 1:

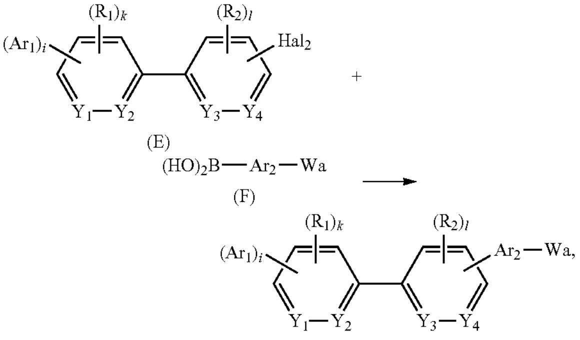

(E) (F) (C)

wherein $Hal_2$ is an halogen, in particular Br, or when j is 1, and i is 1:

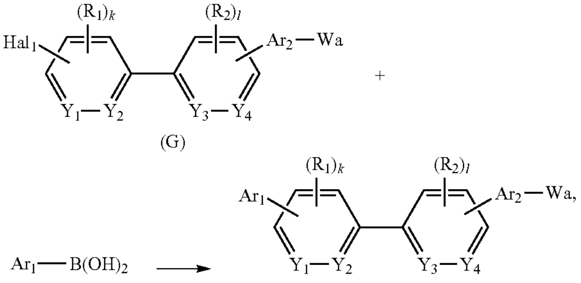

(G) (H) (C)

wherein $Hal_1$ is an halogen, in particular Br, or when j=0, and i is 1:

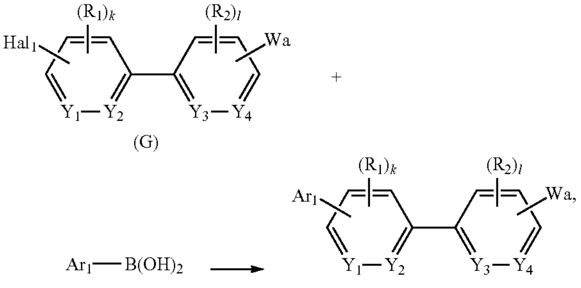

(G) (H) (C)

wherein $Hal_1$ is an halogen, in particular Br.

When j=0 and i=0, compound (C) is then obtainable by procedures well known from those skilled in the art, in particular those described in WO2015132727.

When $Ar_1$ is Hal, compound (C) may be obtained similarly to compound (G) as described below.

When $Ar_1$ is selected from —O—$(C_6-C_{10})$aryl, —O-(5 to 7 membered)heteroaryl, —S—$(C_6-C_{10})$aryl, —S-(5 to 7 membered)heteroaryl, —($C_1$-$C_6$)alkyl-($C_6$-$C_{10}$)aryl, —($C_1$-$C_6$)alkyl-(5 to 7 membered) heteroaryl, compound (C) may be obtained as follows:

- for $Ar_1$=—O—($C_6$-$C_{10}$)aryl, —O-(5 to 7 membered) heteroaryl, —S—($C_6$-$C_{10}$)aryl, or —S-(5 to 7 membered)heteroaryl, from compound (G), for example with $Hal_1$=Br, in contact with Ar—SH or Ar—OH compound, by nuclear aromatic substitution;
- for $Ar_1$=—($C_1$-$C_6$)alkyl-($C_6$-$C_{10}$)aryl, —($C_1$-$C_6$)alkyl-(5 to 7 membered) heteroaryl, from compound (G), for example with $Hal_1$=Br, in particular by Negishi coupling, in presence of an Ar-alkyl-MgBr compound.

In an embodiment, compound (E) is obtained as follows, when i is 1:

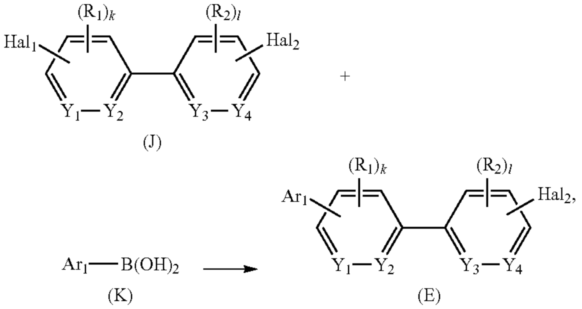

(J) (K) (E)

Wherein $Hal_1$ and $Hal_2$ are halogens, for example I and Br, respectively.

J is obtainable by procedures well known from those skilled in the art, in particular those described in WO2015132727.

When i is 0, (E) is obtainable by procedures well known from those skilled in the art, in particular those described in WO2015132727.

Alternatively, compound (E) may be obtained as follows:

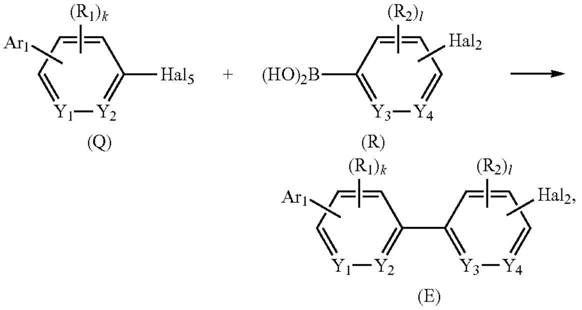

(Q) (R) (E)

wherein $Hal_5$ is an halogen, in particular I, $Hal_2$ being for example Br.

In an embodiment, compound (G) is obtained as follows:

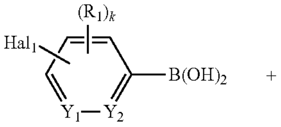

(L)

-continued

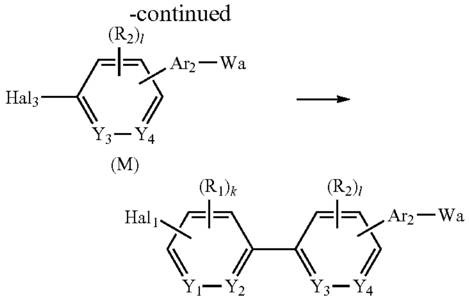

(M) (G)

wherein $Hal_3$ is an halogen, in particular I, $Hal_1$ being for example Br.

Alternatively, compound (G) may be obtained as follows:

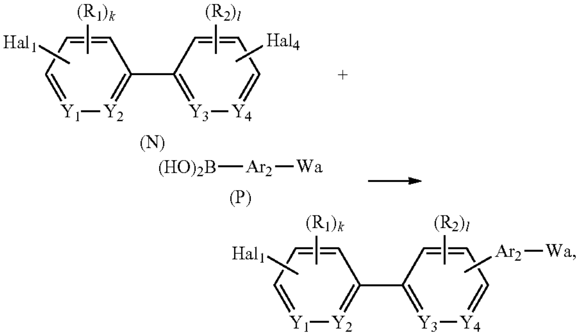

(N) (P) (G)

wherein $Hal_4$ is an halogen, in particular I, $Hal_1$ being for example Br.

- (L) is commercially available or obtained by procedures well known from those skilled in the art.
- (M) is obtainable by procedures well known from those skilled in the art, in particular those described in WO2015132727.
- (N) is obtainable by procedures well known from those skilled in the art, in particular those described in WO2015132727.

In another object, the present invention relates to a method for preparing a compound of formula (I) as defined herein, wherein r is 0, comprising the steps of:

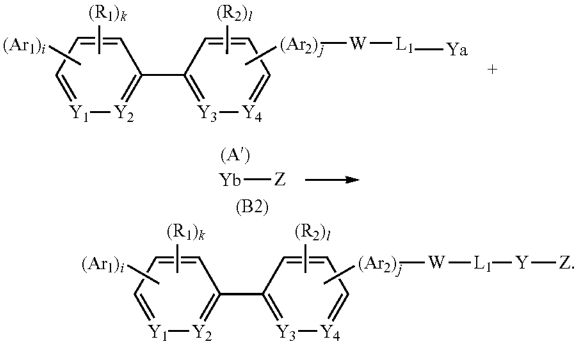

(A') (B2) (I)

Compound (B2) is as mentioned above.

Compound (A') is as defined above as compound (A). Ya and Yb are well known from the skilled person in the art and are for example —COOH or an activated ester and —$NH_2$ respectively, forming —CONH— by peptidic coupling, or —$NH_2$ and —F (—F being in particular bound to an aromatic group), forming —NH— by nucleophilic aromatic substitution.

All the substituents, for example the group $R_3$, may be modified before, between, or after the steps described above. For example, the group $R_3$=OH can be modified to $R_3$=O-propyl by $SN_2$ reaction.

When W is C≡C, the W-containing fragment can for example be introduced to the aromatic scaffold by a Sonogashira coupling as well known from the skilled in the art.

In another object, the present invention relates to a pharmaceutical composition comprising a compound of formula (I) as defined above, in admixture with at least one pharmaceutically acceptable excipient or carrier.

All the embodiments mentioned above for the compounds of formula (I) apply here, alone or in combinations.

In an embodiment, the pharmaceutical composition defined above further comprises an additional anti-cancer agent, in particular chosen from anti-EGFR, anti-Map kinases and anti-Akt compounds. Other exemplary additional anticancer agents include carboplatin, paclitaxel, doxorubicin, topotecan, and functional derivatives of the foregoing.

As will be apparent to one of ordinary skill in the art, the specific formulations of said pharmaceutical composition can be selected based on the type of cancer being treated. The compositions of the invention can be formulated for administration to a patient with materials that improve their stability and/or provide for a controlled or sustained release in vivo.

These pharmaceutical compositions can be prepared in a well known manner in the pharmaceutical art and, can be administered by a variety of routes, depending upon whether local or systemic treatment is desired and upon the area to be treated.

Administration may be topical (including skin, ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral.

In particular, compounds and compositions of the invention are administered by oral administration or by intravenous administration.

The compounds and pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular administration.

The pharmaceutical compositions can be formulated so as to provide controlled, quick, sustained or delayed release of the active ingredient after administration to the patient by employing procedures known in the art.

The pharmaceutical compositions can also be formulated by techniques well known from those skilled in the art, for example by nanovectorization, or by using a micronized form.

Pharmaceutical compositions usually comprise pharmaceutically acceptable, inorganic or organic carriers, preservatives, solubilizers, stabilizers, wetting agents, emulsifiers, sweeteners, colorants, flavorings, salts for varying the osmotic pressure, buffers, masking agents or antioxidants. They can also contain still other therapeutically valuable substances. These ingredients are selected on the basis of the mode and route of administration. Suitable pharmaceutical ingredients, as well as pharmaceutical necessities for use in pharmaceutical formulations, are described in Remington's Pharmaceutical Sciences (E. W. Martin).

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene block polymers, polyethylene glycol and wool fat. The therapeutic dosage of the compounds of the present invention can vary according to, for example, the particular use for which the treatment is made, the manner of administration of the compound, the health and condition of the patient, and the judgment of the attending clinician. The proportion or concentration of a compound of the invention in a pharmaceutical composition can vary depending upon a number of factors including dosage, chemical characteristics (e.g., hydrophobicity), and the route of administration.

In a further object, the present invention thus relates to a compound of formula (I) as defined above for use in the treatment of cancer, notably of hematologic malignancies, such as lymphoma, leukemia, multiple myeloma, and/or of solid tumors such as ovarian cancers, mesothelioma, melanoma, pancrea, lung, breast, kidney and liver cancers.

All the embodiments mentioned above for the compounds of formula (I) apply here, alone or in combinations.

In a particular embodiment, the present invention thus relates to a compound of formula (I) as defined above for use in the treatment of cancer by inducing apoptosis mediated by at least one of the proteins chosen from Bcl-2, Mcl-1, Bcl-$x_L$, Bcl-w, Bfl-1 and Bcl-B, in particular of Bcl-2 protein, or Bcl-$x_L$ and/or Mcl-1 proteins, more particularly of Bcl-2 protein, or Bcl-$x_L$ and Mcl-1 proteins.

Cancers amenable to the therapeutic methods of the invention can be cancers that are responsive to the modulation of at least one of the proteins chosen from Bcl-2, Mcl-1, Bcl-$x_L$, Bcl-w, Bfl-1 and Bcl-B, in particular of Bcl-2 protein, or Bcl-$x_L$ and/or Mcl-1 proteins; any form of cancer which is associated with misregulation of at least one of the proteins chosen from Bcl-2, Mcl-1, Bcl-$x_L$, Bcl-w, Bfl-1 and Bcl-B, in particular of Bcl-2 protein, or Bcl-$x_L$ and/or Mcl-1 proteins (e.g., overexpression or altered binding or activity) is thus within the scope of the invention.

Cancers or neoplastic disorders include, for example, without limitation, breast cancer, hematological cancers such as myeloma, leukemia and lymphoma (e.g., Burkitt lymphoma, non-Hodgkin lymphoma, Hodgkin lymphoma, and acute T cell leukemia), neurological tumors such as brain tumors, e.g., gliomas, including astrocytomas or glioblastomas, melanomas, lung cancer, head and neck cancer, thyroid cancer, gastrointestinal tumors such as stomach, colon or rectal cancer, liver cancer, pancreatic cancer, genitourinary tumors such ovarian cancer, vaginal cancer, vulval cancer, endometrial cancer, bladder cancer, kidney cancer, testicular cancer, prostate cancer, or penile cancer, bone tumors, vascular tumors, and skin cancers such as basal cell carcinoma, squamous cell carcinoma and melanoma.

In another aspect, there are included compounds of formula (I), for use as a ligand of at least one of the proteins chosen from Bcl-2, Mcl-1, Bcl-$x_L$, Bcl-w, Bfl-1 and Bcl-B, in particular of Bcl-2 protein, or Bcl-$x_L$ and/or Mcl-1 proteins, more particularly of Bcl-2 protein, or Bcl-$x_L$ and Mcl-1 proteins.

In another aspect, there are included compounds of formula (I), for use for inducing apoptosis mediated by at least one of the proteins chosen from Bcl-2, Mcl-1, Bcl-$x_L$, Bcl-w, Bfl-1 and Bcl-B, in particular of Bcl-2 protein, or Bcl-$x_L$ and/or Mcl-1 proteins, more particularly of Bcl-2 protein, or Bcl-$x_L$ and Mcl-1 proteins.

A patient is effectively treated whenever a clinically beneficial result ensues. This may mean, for example, a complete resolution of the symptoms of a disease, a decrease in the severity of the symptoms of the disease, or a slowing of the disease's progression.

An effective amount of any composition provided herein can be administered to an individual in need of treatment. The term "effective" as used herein refers to any amount that induces a desired response while not inducing significant toxicity in the patient. Such an amount can be determined by assessing a patient's response after administration of a known amount of a particular composition.

In another aspect, the inventions relate to a method of treating cancer comprising administering to a patient in need thereof an effective amount of pharmaceutical composition comprising a compound of formula (I) as defined above.

In another aspect, the inventions relate to a method of degrading at least one of the proteins chosen from Bcl-2, Mcl-1, Bcl-$x_L$, Bcl-w, Bfl-1 and Bcl-B, in particular of Bcl-2 protein, or Bcl-$x_L$ and/or Mcl-1 proteins, more particularly of Bcl-2 protein, or Bcl-$x_L$ and Mcl-1 proteins, comprising contacting said protein with a compound of formula (I) as defined above.

In another aspect, the inventions relate to a method of degrading at least one of the proteins chosen from Bcl-2, Mcl-1, Bcl-$x_L$, Bcl-w, Bfl-1 and Bcl-B, in particular Bcl-2 protein, or Bcl-$x_L$ and/or Mcl-1 proteins, more particularly Bcl-2 protein, or Bcl-$x_L$ and Mcl-1 proteins, in vivo comprising contacting the protein with a compound of formula (I) as defined above to degrade said protein by ubiquitination targeted by said compound of formula (I).

The present invention also relates to methods of killing cancer cells and methods of modulating levels of at least one of the proteins chosen from Bcl-2, Mcl-1, Bcl-$x_L$, Bcl-w, Bfl-1 and Bcl-B, in particular of Bcl-2 protein, or Bcl-$x_L$ and/or Mcl-1 proteins in a cell. The therapeutic methods described herein can be carried out in connection with other cytotoxic therapies (e.g., chemotherapy, hormone therapy, radiotherapy, antibody-based therapies or targeted therapies directed against cell signaling pathways).

In a preferred embodiment, the compound and the composition of the invention are useful for preventing or reducing metastasis or further dissemination in patient suffering from Bcl-2, Mcl-1, Bcl-$x_L$, Bcl-w, Bfl-1 and Bcl-B, in particular Bcl-2, or Bcl-$x_L$ and/or Mcl-1 expressing cancer; more specifically, they are useful for increasing the duration of survival of such a patient, increasing the progression free survival of such a patient, increasing the duration of response, resulting in a statistically significant and clinically meaningful improvement of the treated patient as measured by the duration of survival, progression free survival, response rate or duration of response. In a preferred embodiment, the medicament is useful for increasing the response rate in a group of patients.

Definitions

The following terms and expressions contained herein are defined as follows:

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, and alkoxycarbonyl, has the same meaning as alkyl defined above. Lower alkyl groups, which are preferred, are alkyl groups as defined above which contain 1 to 4 carbons. A designation such as "$C_1$-$C_6$ alkyl" refers to an alkyl radical containing from 1 to 6 carbon atoms.

As used herein, the term "alkenyl" refers to a straight chain, or branched hydrocarbon chains of 2 to 6 carbon atoms having at least one carbon-carbon double bond. A designation "$C_2$-$C_6$ alkenyl" refers to an alkenyl radical containing from 2 to 6 carbon atoms. Examples of alkenyl groups include ethenyl, propenyl, isopropenyl, 2,4-pentadienyl. "$C_2$-$C_4$ alkenyl" are particularly preferred.

As used herein, the term "alkoxy" means an alkyl-O— group wherein the alkyl group is as herein described. Exemplary alkoxy groups include methoxy, ethoxy, n-propoxy, i-propoxy, and n-butoxy.

As used herein, the term "aryl" refers to a substituted or unsubstituted, mono- or bicyclic hydrocarbon aromatic ring system having 6 to 10 ring carbon atoms. Examples include phenyl and naphthyl.

As used herein, the term "arylalkyl" refers to an alkyl group that is substituted with an aryl group. Examples of arylalkyl groups include, but are not limited to, benzyl, bromobenzyl, phenethyl, benzhydryl, diphenylmethyl, triphenylmethyl, diphenylethyl, naphthylmethyl.

As used herein, the term "arylalkenyl" refers to an alkenyl group that is substituted with an aryl group. Examples of arylalkenyl include, but are not limited to, styryl.

As used herein, the term "arylcarbonyl" refers to an aryl-C(═O)— group wherein the aryl group is as herein described.

As used herein, the term "arylalkylcarbonyl" refers to an arylalkyl-C(═O)— group wherein the arylalkyl group is as herein described.

As used herein, the term "heteroaryl" refers to an aromatic group containing 5 to 10 ring carbon atoms, preferably 5 to 7, in which one or more ring carbon atoms are replaced by at least one hetero atom such as —O—, —N—, or —S—. Examples of heteroaryl groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Included within the definition of "heteroaryl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene.

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorders. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

The meanings of all the other terms used in the description of the present invention are well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, fumaric, maleic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically acceptable salts, other salts are included in the invention. They may serve as intermediates in the purification of the compounds, in the preparation of other salts, or in the identification and characterization of the compounds or intermediates.

FIGURES

FIG. 1 presents the CRBN expression on IGROV1-R10 ovarian cancer cell line, according to example 4.

Figure 2:
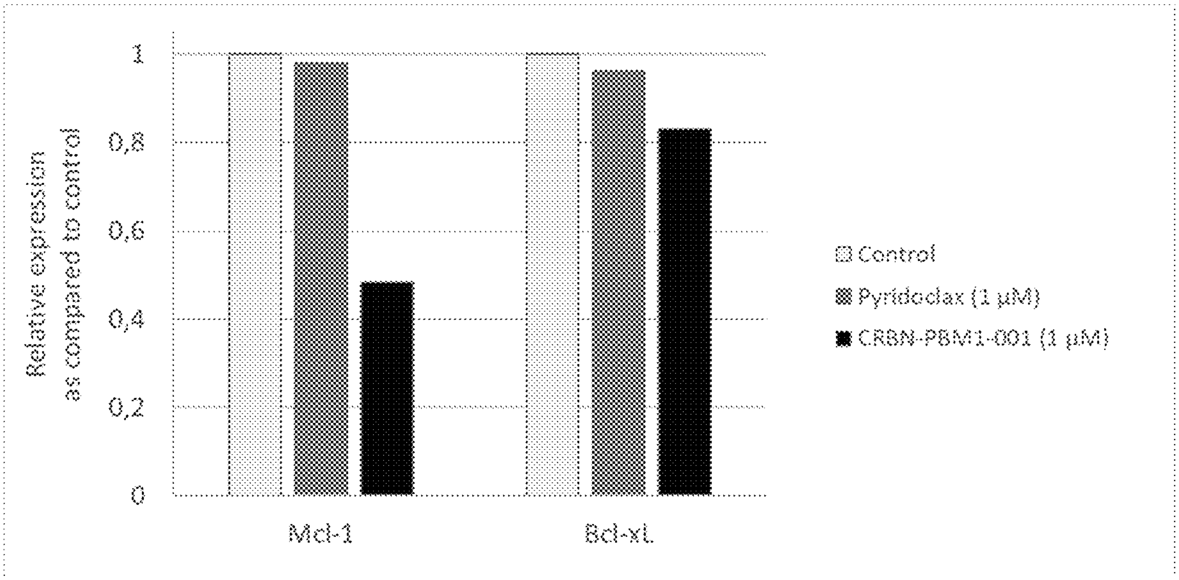

FIG. 2 illustrates the expression of Mcl-1 and Bcl-$x_L$ after a 24 h exposure of IGROV1-$R_{10}$ cells to 1 μM Pyridoclax or to 1 μM CRBN-PBM1-001 quantified by densitometry analysis of the western blot signals, according to example 4.

EXAMPLES

Example 1: Synthesis of Compounds of Formula (I)

Material and method are described below.

Material

Commercial reagents were used as received without additional purification. Melting points were determined on a Kofler heating bench. IR spectra were recorded on a Perkin Elmer BX FT-IR spectrophotometer. The band positions are given in reciprocal centimeters ($cm^{-1}$). $^1$H NMR (400 MHz) and $^{13}$C NMR (100 MHz) spectra were recorded on a JEOL Lambda 400 spectrometer. Chemical shifts are expressed in parts per million downfield from tetramethylsilane as an internal standard and coupling constants in Hertz. Chemical shift are reported in part per million (ppm) relative to the solvent resonance. Chromatography was carried out on a column using flash silica gel 60 Merck (0.063-0.200 mm) as the stationary phase. The eluting solvent indicated for each purification was determined by thin layer chromatography (TLC) performed on 0.2 mm precoated plates of silica gel 60F-264 (Merck) and spots were visualized using an ultraviolet-light lamp. Elemental analyses for new compounds were performed and the data for C, H, and N were within ±0.4 of the theoretical values for all final compounds.

Methods

Compounds of the invention were synthesized as follows. Reactions were performed in the order indicated in brackets, according to the general procedures mentioned below:

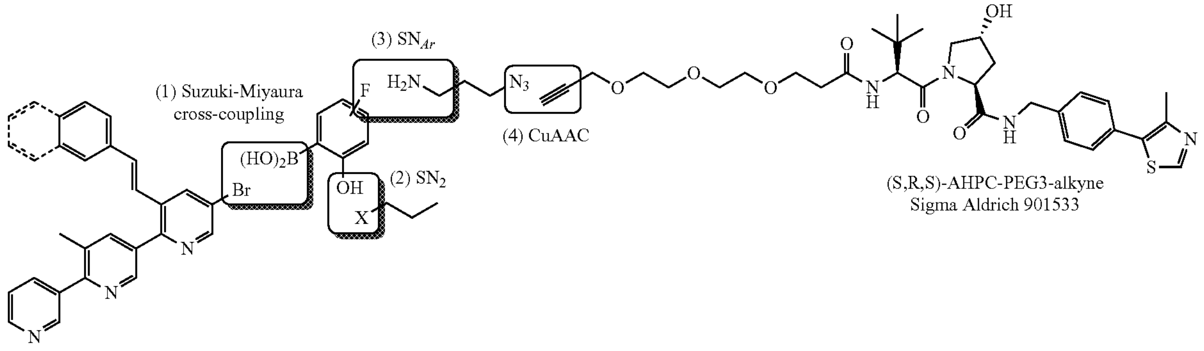
(S,R,S)-AHPC-PEG3-alkyne
Sigma Aldrich 901533
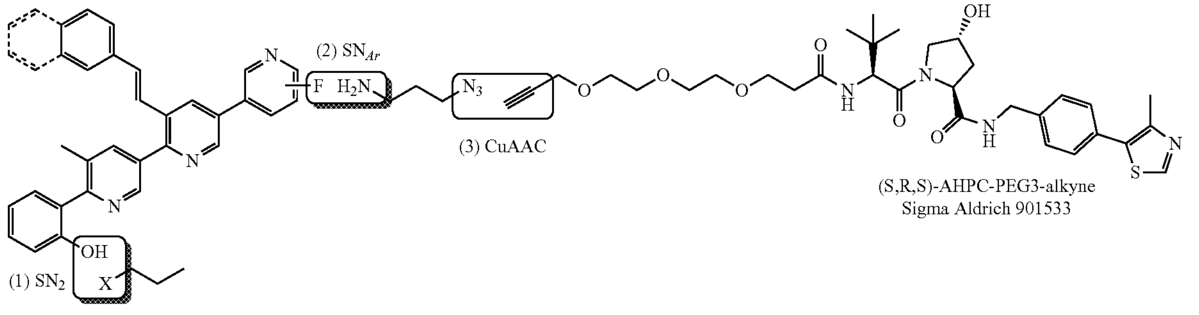
(S,R,S)-AHPC-PEG3-alkyne
Sigma Aldrich 901533
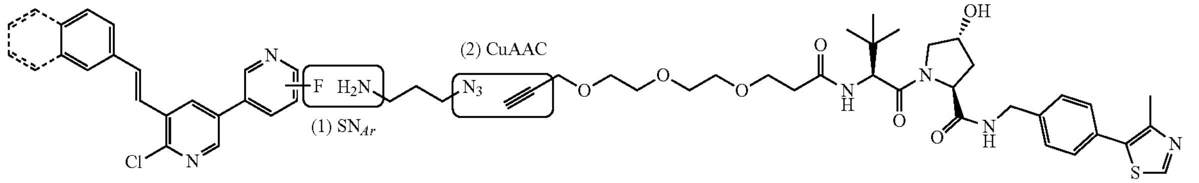
(S,R,S)-AHPC-PEG3-alkyne
Sigma Aldrich 901533
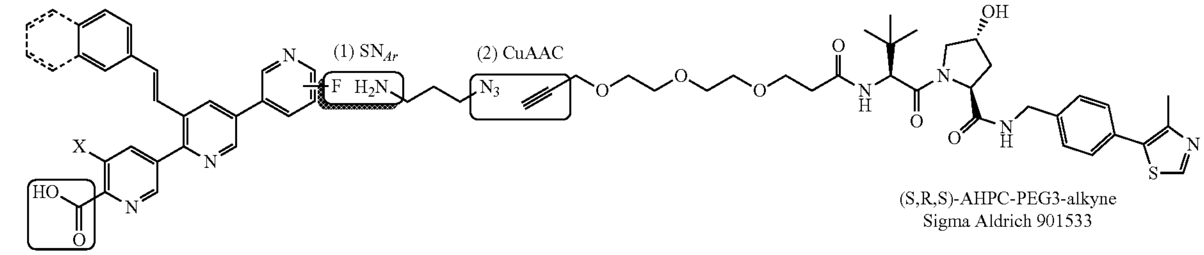
(S,R,S)-AHPC-PEG3-alkyne
Sigma Aldrich 901533
(3) Nitrile hydrolysis & protection/deprotection strategies
X = Cl or H
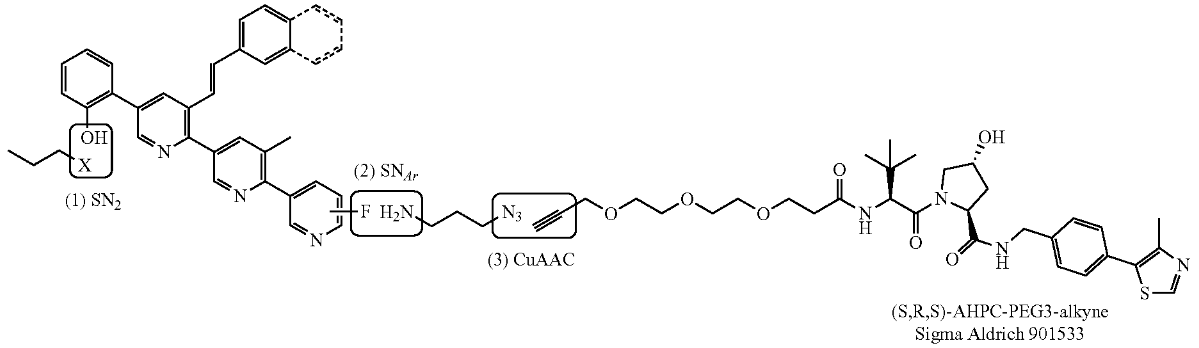
(S,R,S)-AHPC-PEG3-alkyne
Sigma Aldrich 901533

-continued
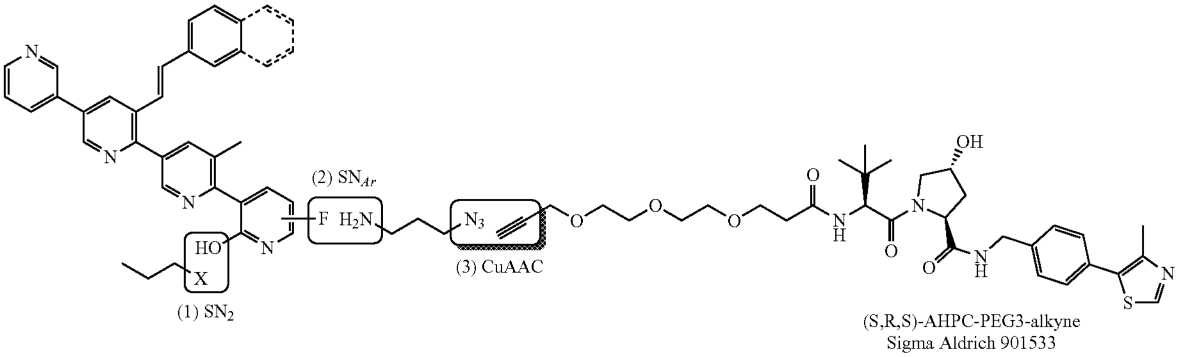
(S,R,S)-AHPC-PEG3-alkyne
Sigma Aldrich 901533
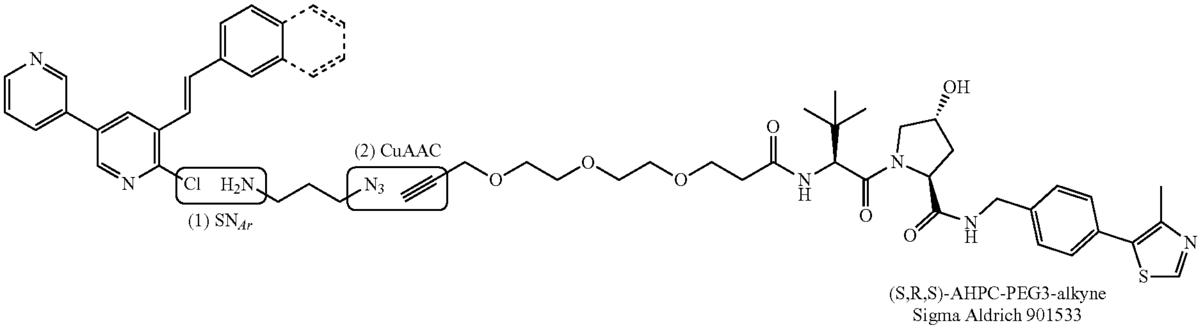
(S,R,S)-AHPC-PEG3-alkyne
Sigma Aldrich 901533
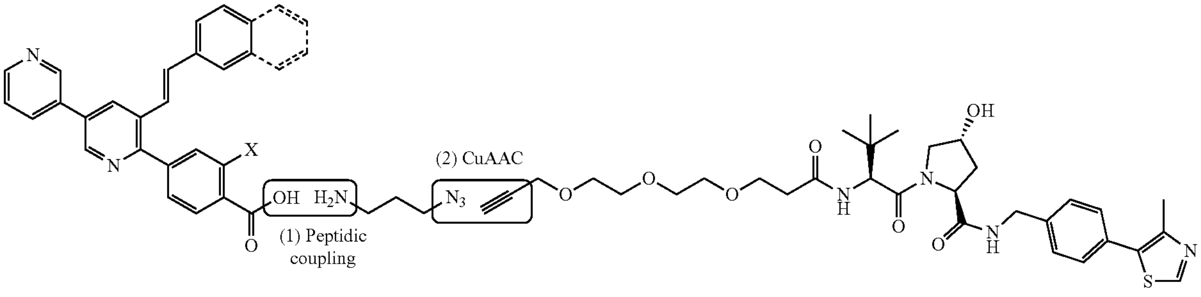
(S,R,S)-AHPC-PEG3-alkyne
Sigma Aldrich 901533
X = Cl or H
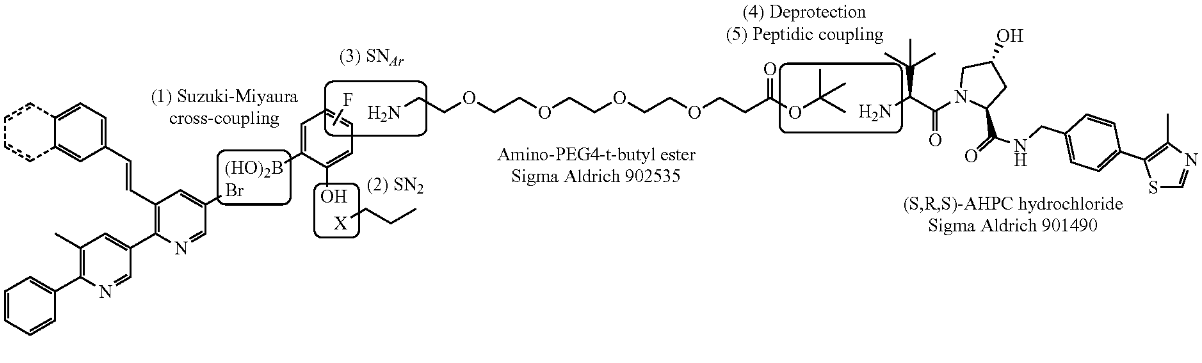
Amino-PEG4-t-butyl ester
Sigma Aldrich 902535
(S,R,S)-AHPC hydrochloride
Sigma Aldrich 901490

-continued
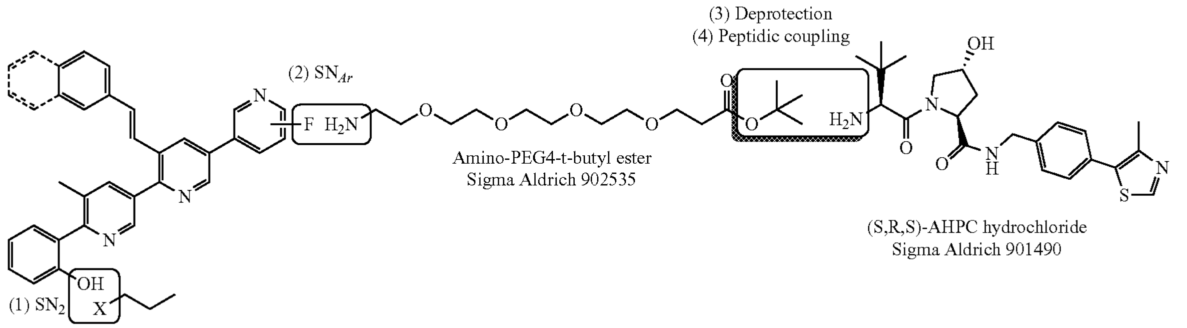
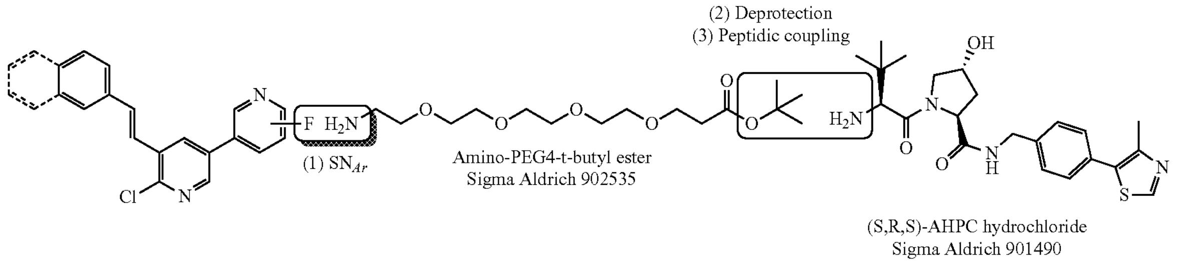
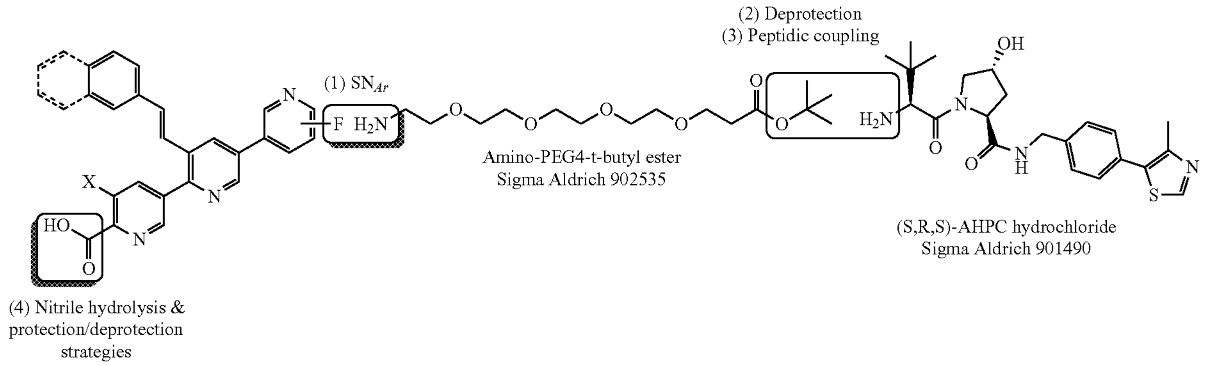
X = Cl or H
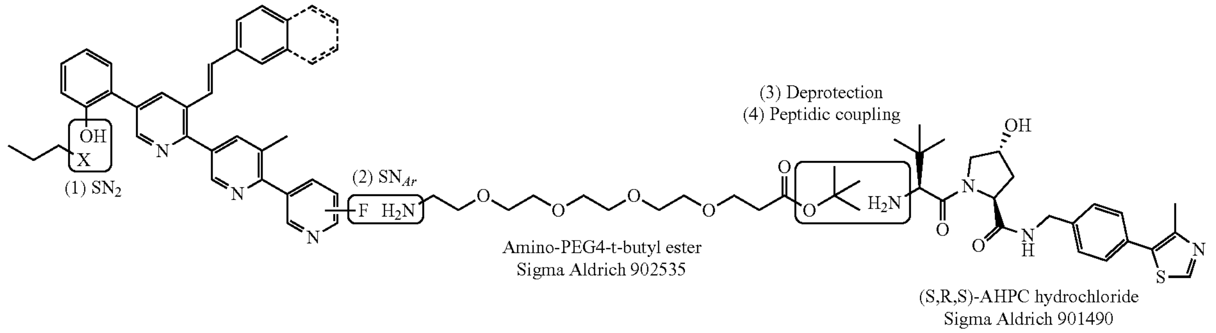
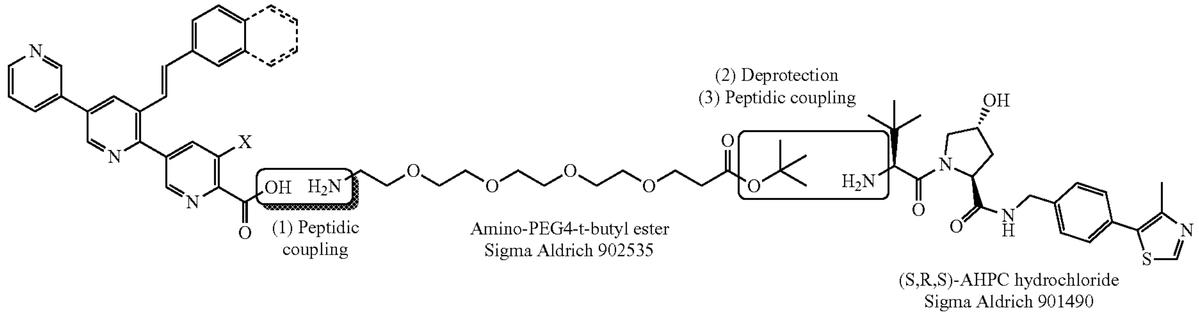
X = Cl or H -continued
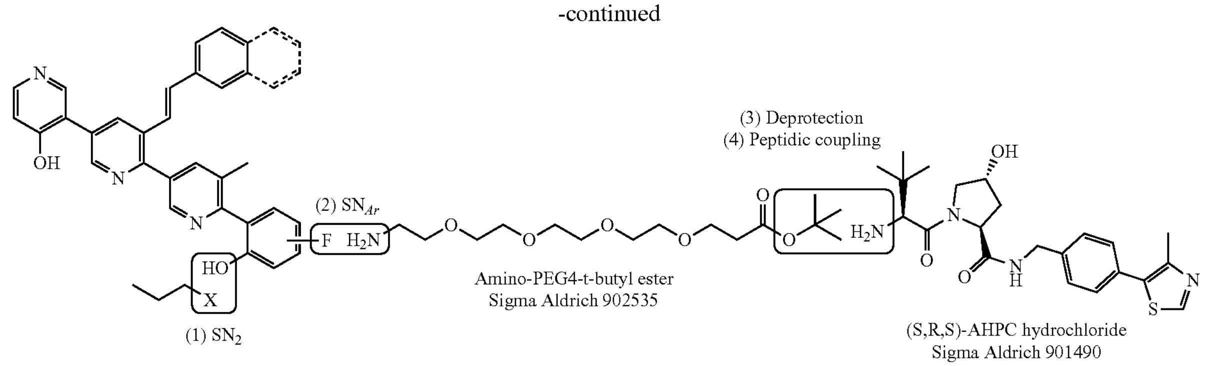
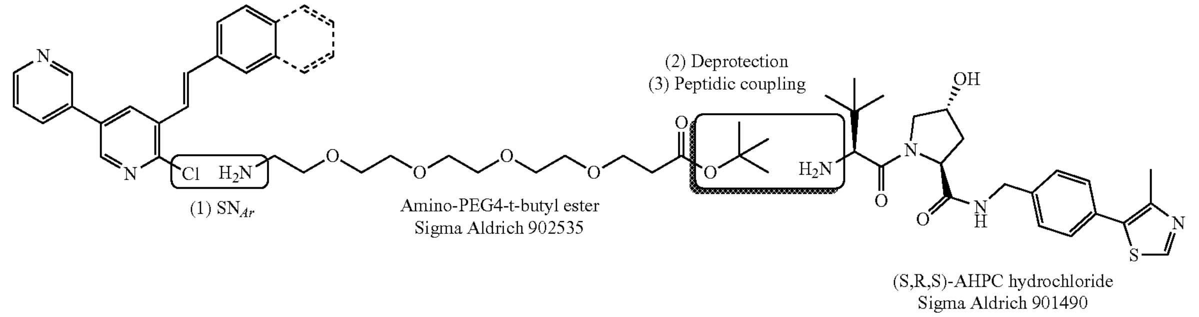
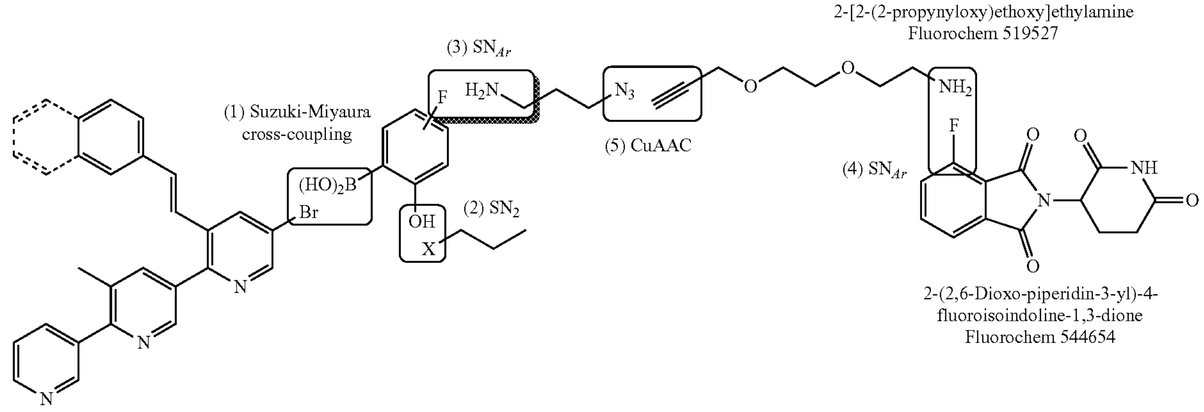
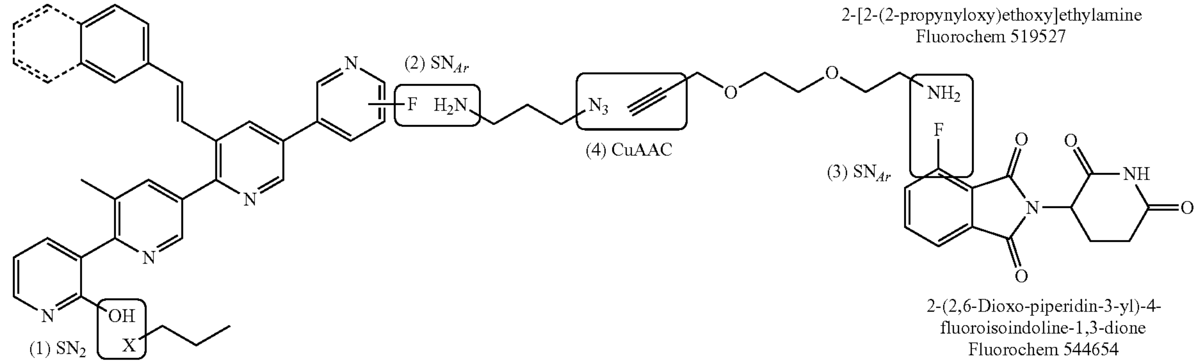

-continued

2-[2-(2-propynyloxy)ethoxy]ethylamine
Fluorochem 519527

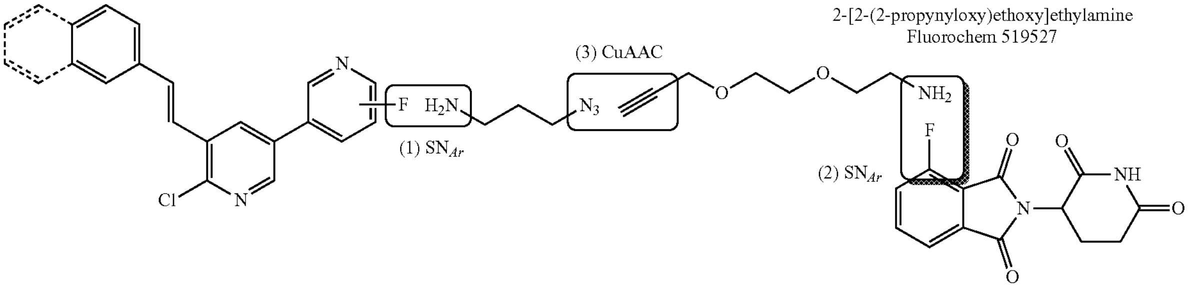

2-(2,6-Dioxo-piperidin-3-yl)-4-fluoroisoindoline-1,3-dione
Fluorochem 544654

2-[2-(2-propynyloxy)ethoxy]ethylamine
Fluorochem 519527

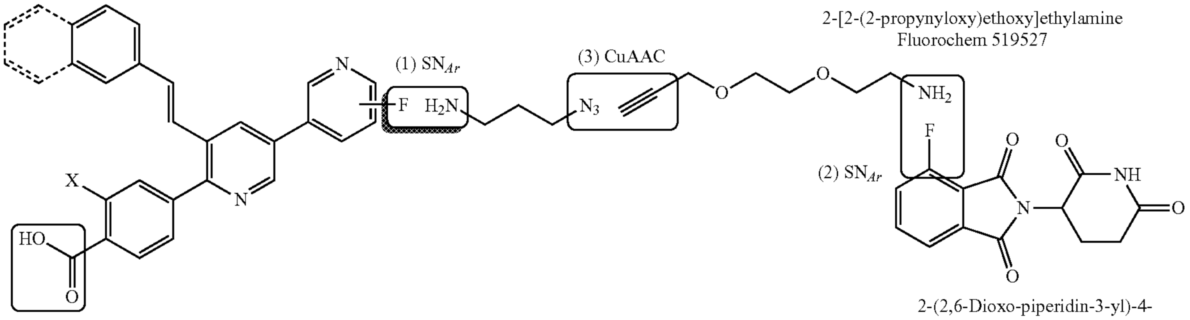

(4) Nitrile hydrolysis & protection/deprotection strategies 2-(2,6-Dioxo-piperidin-3-yl)-4-fluoroisoindoline-1,3-dione
Fluorochem 544654

X = Cl or H

2-[2-(2-propynyloxy)ethoxy]ethylamine
Fluorochem 519527

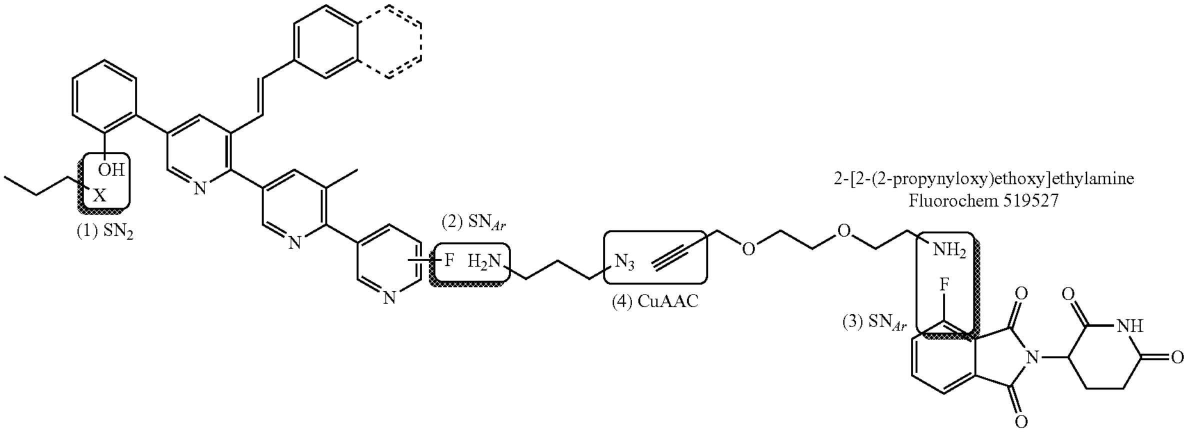

2-(2,6-Dioxo-piperidin-3-yl)-4-fluoroisoindoline-1,3-dione
Fluorochem 544654

-continued
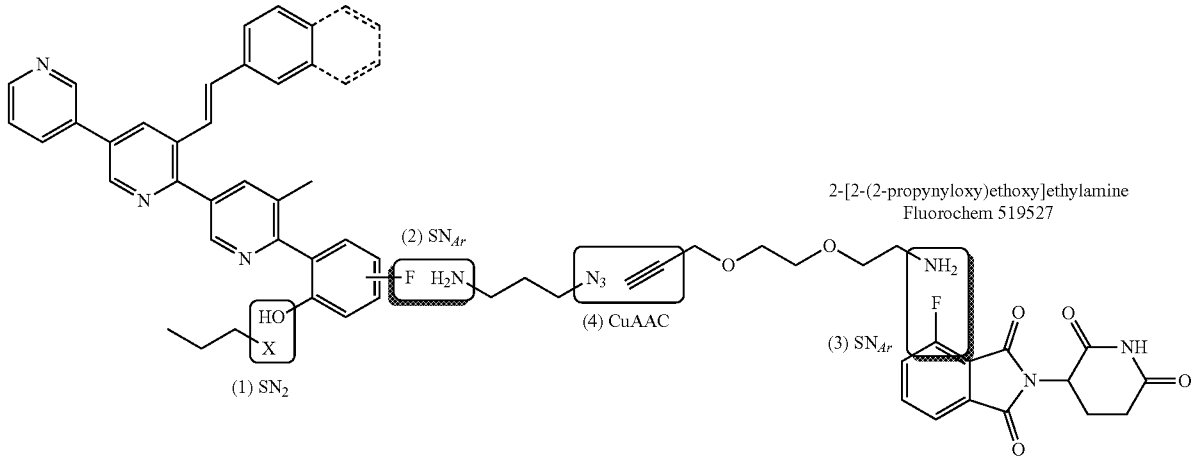
2-[2-(2-propynyloxy)ethoxy]ethylamine
Fluorochem 519527
2-(2,6-Dioxo-piperidin-3-yl)-4-fluoroisoindoline-1,3-dione
Fluorochem 544654
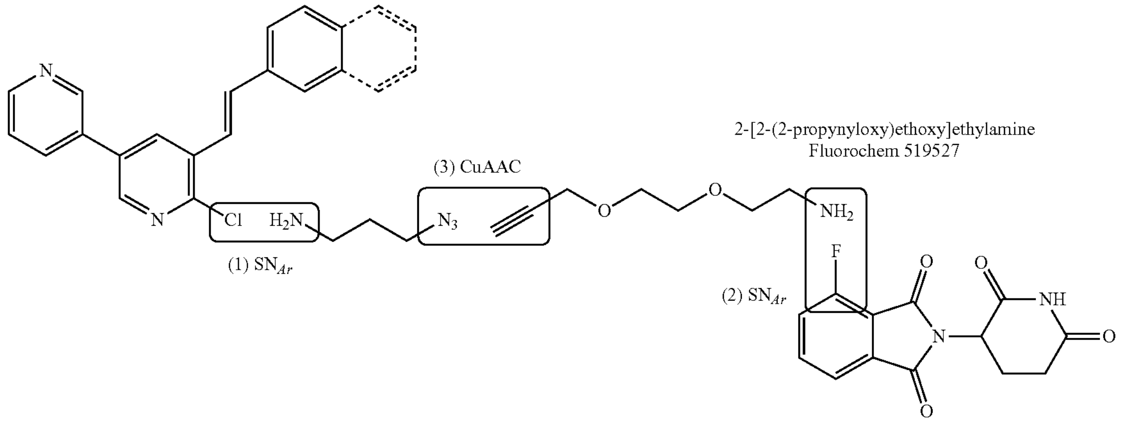
2-[2-(2-propynyloxy)ethoxy]ethylamine
Fluorochem 519527
2-(2,6-Dioxo-piperidin-3-yl)-4-fluoroisoindoline-1,3-dione
Fluorochem 544654
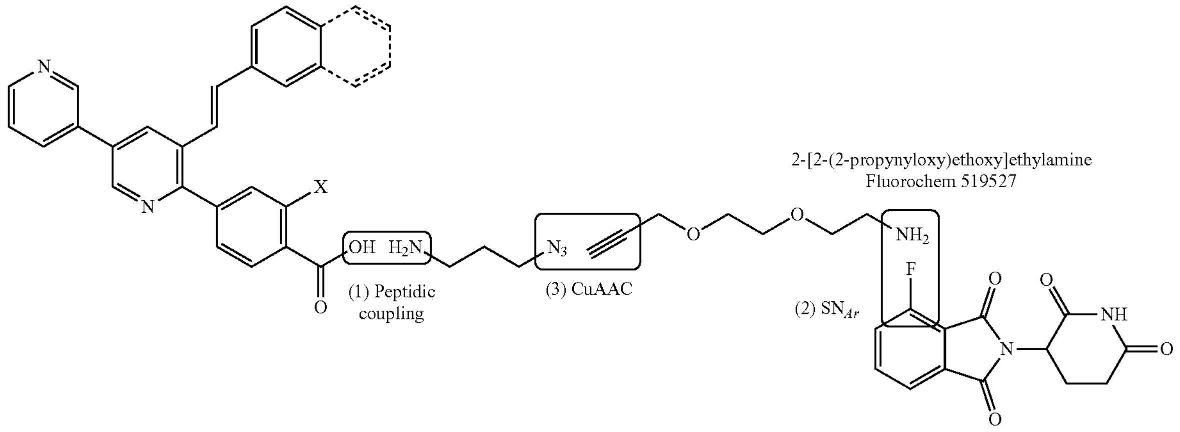
2-[2-(2-propynyloxy)ethoxy]ethylamine
Fluorochem 519527
2-(2,6-Dioxo-piperidin-3-yl)-4-fluoroisoindoline-1,3-dione
Fluorochem 544654
X = Cl or H -continued
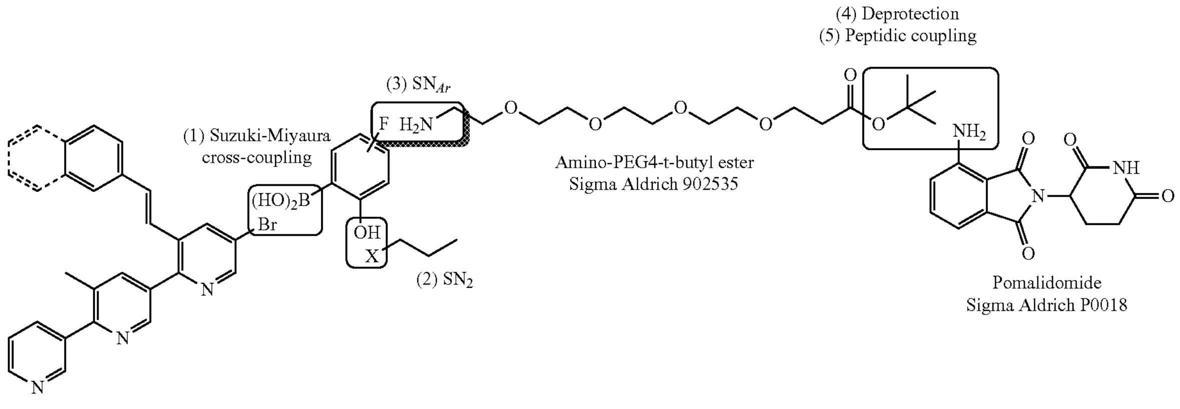
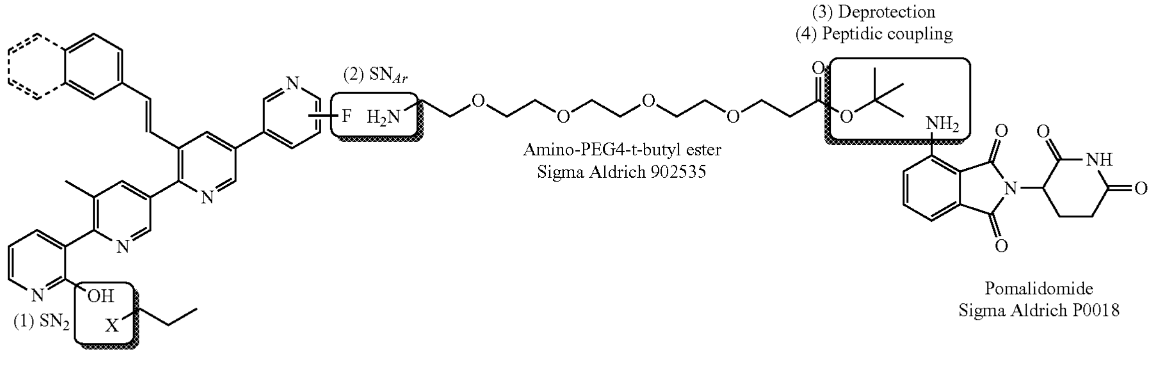
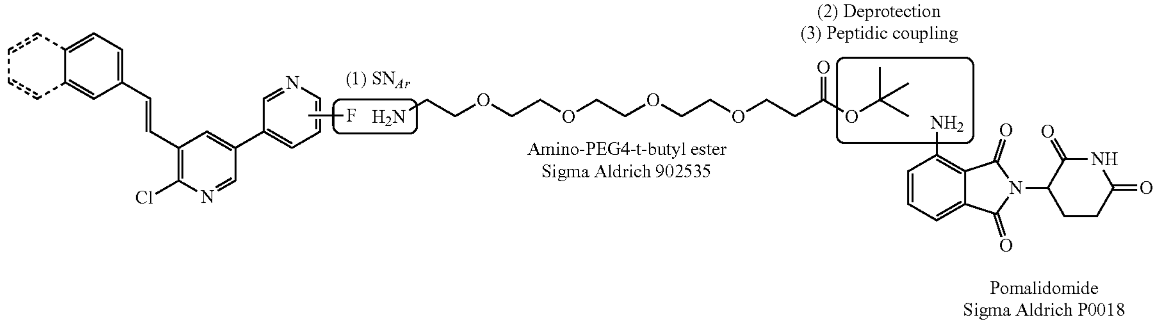
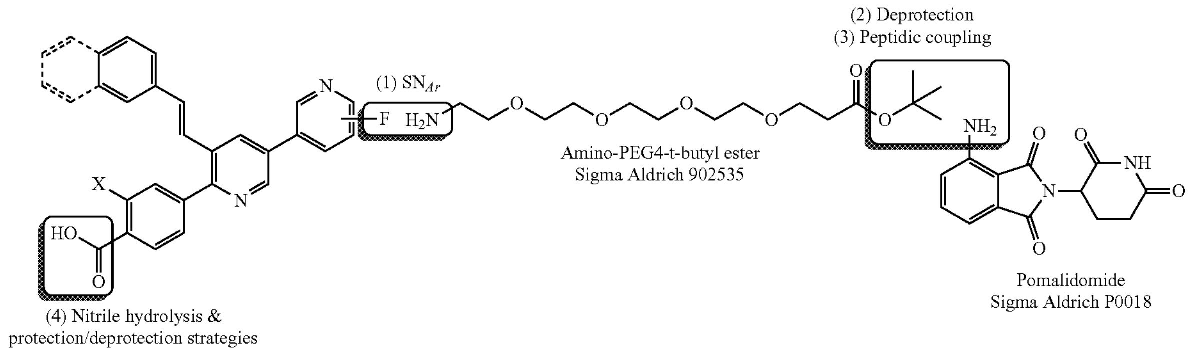
X = Cl or H -continued
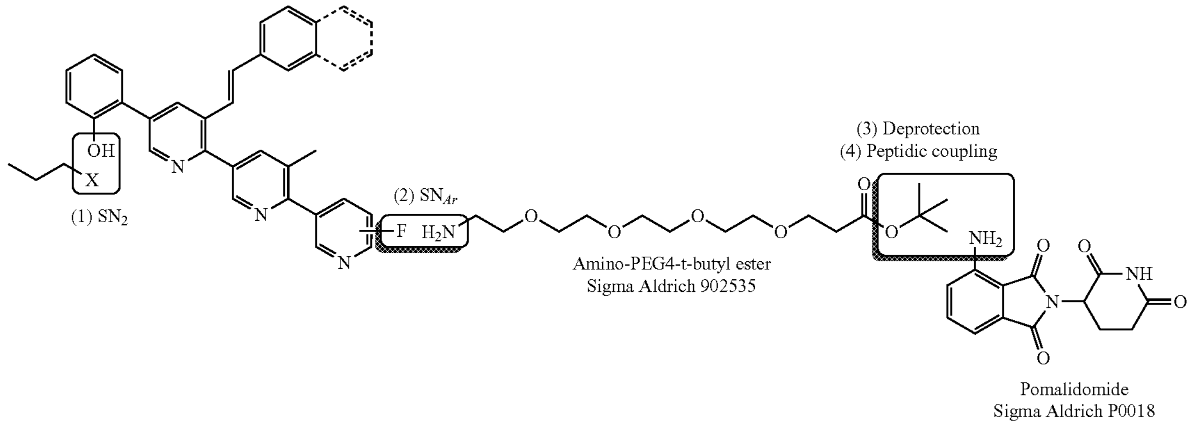
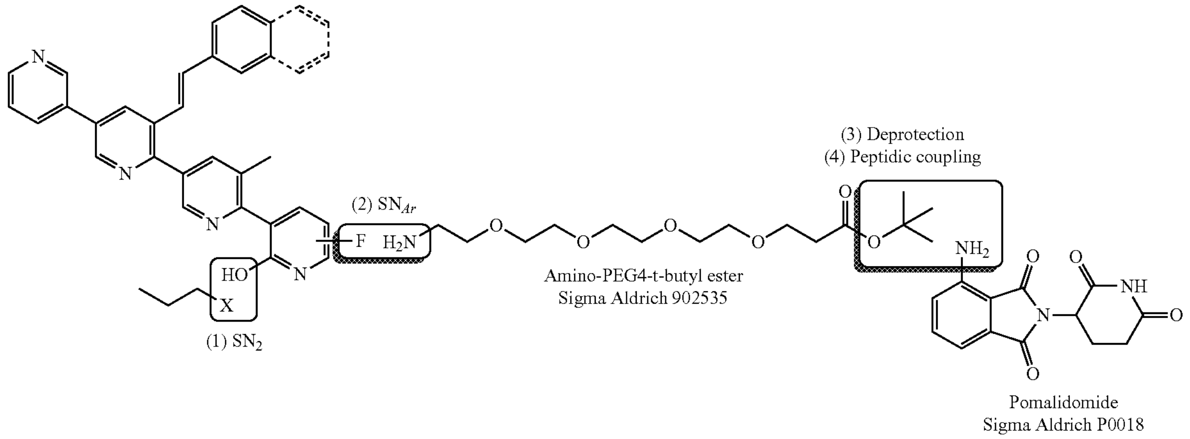
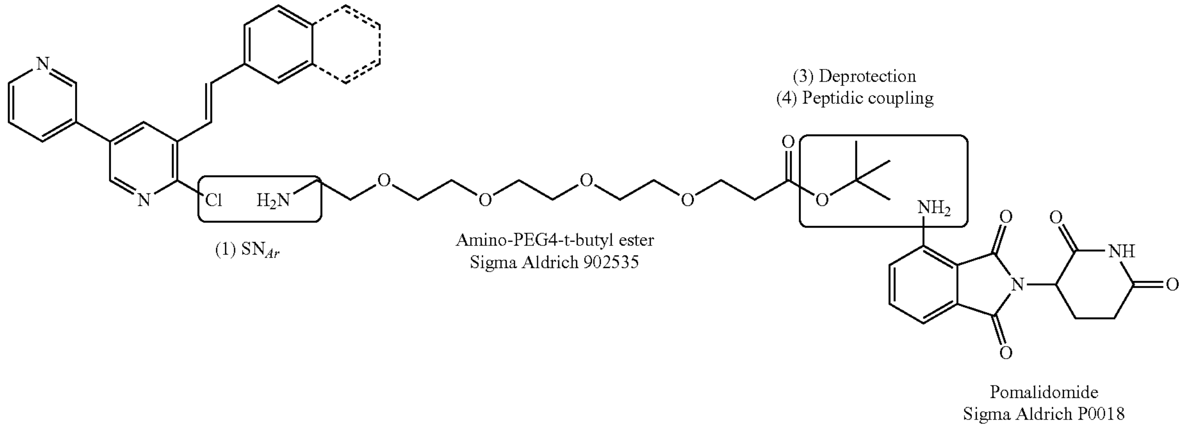

-continued

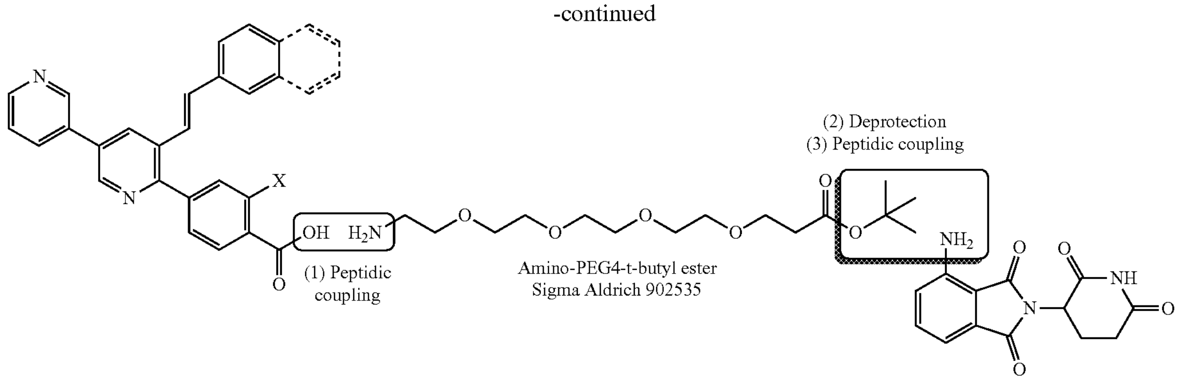

Pomalidomide
Sigma Aldrich P0018

X = Cl or H

General procedure for Suzuki-Miyaura cross-coupling reaction: To a reaction vessel containing a solution of the appropriate bromo- or iodopyridine derivative in 1,4-dioxane (0.2 M) under inert atmosphere, the boronic acid reactant (1.1 equiv), tetrakis(triphénylphosphine)palladium(0) (5 mol %) and saturated $K_3PO_4$ aqueous solution (2.5 equiv) were added. The mixture was refluxed until completion of the reaction (monitored by TLC). The mixture was cooled to room temperature, quenched with water and extracted in ethyl acetate. The organic layers were collected, washed with brine, dried over anhydrous magnesium sulfate, filtered and concentrated under reduced pressure to give the crude residue which was purified by column chromatography.

General procedure for Nucleophilic Aromatic Substitution $SN_{Ar}$:

The amine was dissolved in dry DMSO and DIPEA (N,N-diisopropylethylamine) (2 to 4 equiv). Fluoro- or chloro(pyridyl) or (benzyl) compound (1.0 equiv) was added, and the mixture was stirred at 90° C. until completion of the reaction (monitored by TLC). After cooling to rt, the mixture was poured onto half-saturated brine and it was extracted with EtOAc. The combined organic layers were further washed with saturated $NH_4Cl$ solution, 5% LiCl solution, and brine. The organic layers were dried over $Na_2SO_4$, filtered and concentrated in vacuo.

General procedure for Nucleophilic Substitution $SN_2$: To a reaction vessel containing phenol compound (1.0 equiv) in DMF, iodoalkane (2.0 equiv) and $K_2CO_3$ (4.0 equiv) were added at 0° C. The reaction mixture was stirred at rt until completion of the reaction (monitored by TLC). The mixture was extracted with ethyl acetate. The combined organic layers were washed with brine, dried over anhydrous magnesium sulfate, filtered and concentrated under reduced pressure to give the crude residue which was purified by column chromatography.

General Procedure for Copper(I)-Catalyzed Azide-Alkyne Cycloaddition CuACC:

To a mixture of azide compound (1.0 equiv) and alkyne compound (1.33 equiv) in $^t$BuOH-THF (1:1, v/v) under inert atmosphere was added $CuSO_4 \cdot 5H_2O$ (2.2 equiv) and sodium L-ascorbate (2.2 equiv) in water. The mixture was stirred at 55° C. until completion of the reaction (monitored by TLC) and cooled to room temperature. Then it was poured into water and extracted with DCM. The organic phase was washed with brine, dried over $Na_2SO_4$, filtered and evaporated to dryness. The crude product was purified by silica gel flash column chromatography using DCM and MeOH as eluents.

General Procedure for Nitrile Hydrolysis:

Benzonitrile compound (1.0 equiv) was stirred in a mixture of NaOH (2N) and MeOH at 100° C. until completion of the reaction (monitored by TLC). The reaction mixture was cooled at rt. The reaction mixture was acidified by AcOH until the apparition of a precipitate. The precipitate was filtered.

General Procedure for Peptidic Coupling Reaction:

The carboxylic acid compound (1.0 equiv.) was dissolved in dry DMF and DIPEA (3.0 equiv) and HATU (1.1 equiv) were added under inert atmosphere. After stirring for 5 min, the amine derivative (1.1 equiv.), dissolved in dry DMF was added. The combined mixture was stirred at rt until completion of the reaction (monitored by TLC). Half-saturated brine was added and it was extracted with EtOAc. The combined organic layers were further washed with saturated $NH_4Cl$ solution, 5% LiCl solution, and brine. The organic layers were dried over $Na_2SO_4$, filtered and concentrated in vacuo.

General Procedure for Boc-Deprotection and HATU Coupling:

The Boc-protected linker conjugate (1.0 equiv) was dissolved in dry $CH_2Cl_2$ and it was treated with trifluoroacetic acid. The mixture was stirred until completion of the reaction at rt. The solvent was removed and it was co-evaporated with dry $CH_2Cl_2$. The oily residue was further dried in high vacuum. The deprotected acid derivative (1.0 equiv) was dissolved in dry DMF and DIPEA (3.0 equiv) and HATU (1.1 equiv) were added. After stirring for 5 min, the amine derivative (1.1 equiv) dissolved in dry DMF, was added. The combined mixture was stirred at rt until completion of the reaction (monitored by TLC). Half-saturated brine was added and it was extracted with EtOAc. The combined organic layers were further washed with saturated $NH_4Cl$ solution, 5% LiCl solution, and brine. The organic layers were dried over $Na_2SO_4$, filtered and concentrated in vacuo.

Starting compounds mentioned above have been obtained as follows:

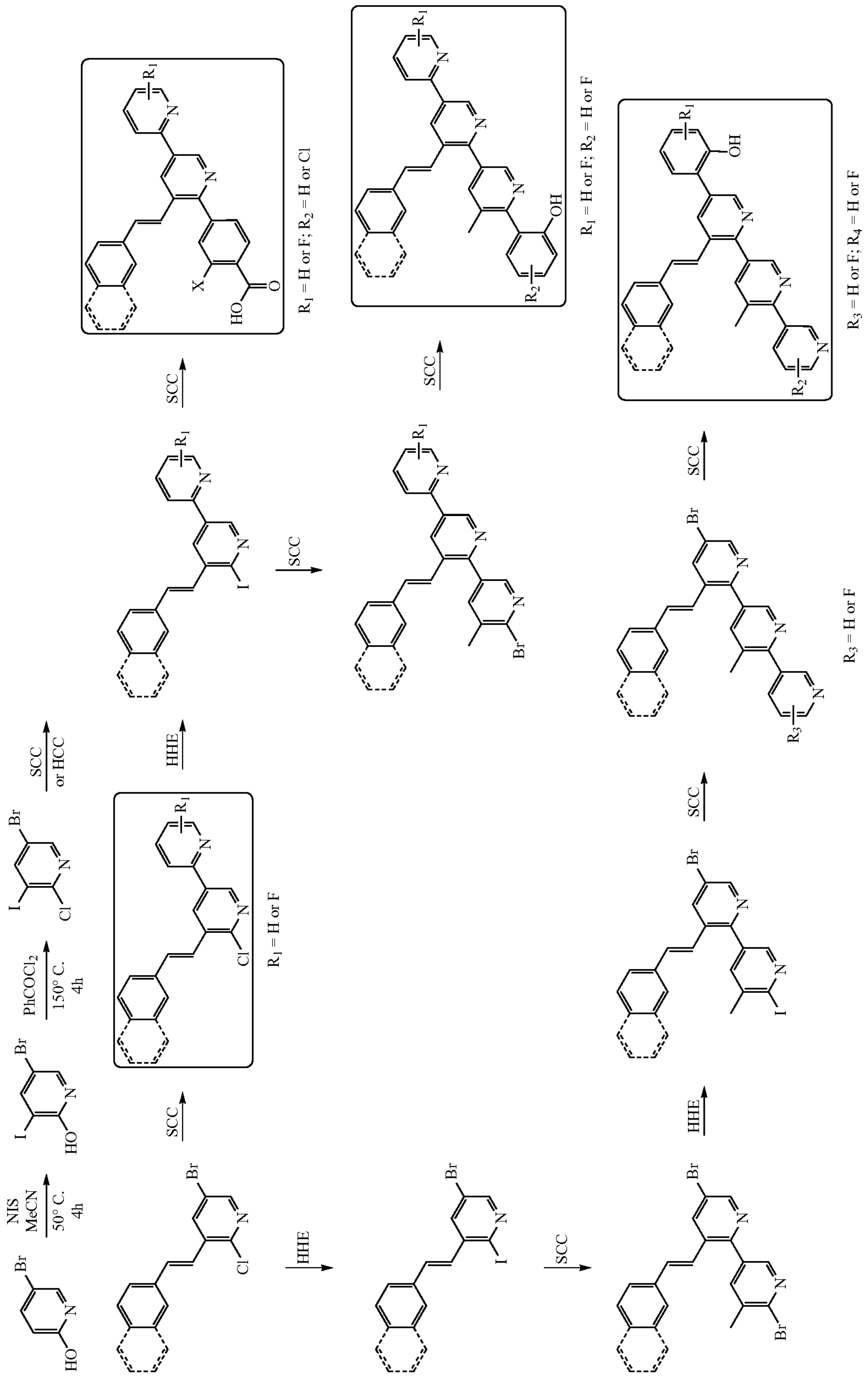
NIS
MeCN
50° C.
4h
PhCOCl2
150° C.
4h
SCC
or HCC
SCC
HHE
SCC
SCC
R1 = H or F
R1 = H or F; R2 = H or Cl
R1 = H or F; R2 = H or F
HHE
SCC
SCC
HHE
SCC
R3 = H or F
SCC
R3 = H or F; R4 = H or F -continued Key:
Suzuki-Miyaura cross-coupling reaction (SCC)
Heck cross-coupling reaction (HCC)
Halogen-halogen exchange (HHE)

analogously to what has been described in WO2015132727.

When $Ar_1$ is selected from —O—($C_6$-$C_{10}$)aryl, —O-(5 to 7 membered)heteroaryl, —S—($C_6$-$C_{10}$)aryl, —S-(5 to 7 membered)heteroaryl, —($C_1$-$C_6$)alkyl-($C_6$-$C_{10}$)aryl, —($C_1$-$C_6$)alkyl-(5 to 7 membered) heteroaryl, the Ar group may be introduced analogously as indicated below:

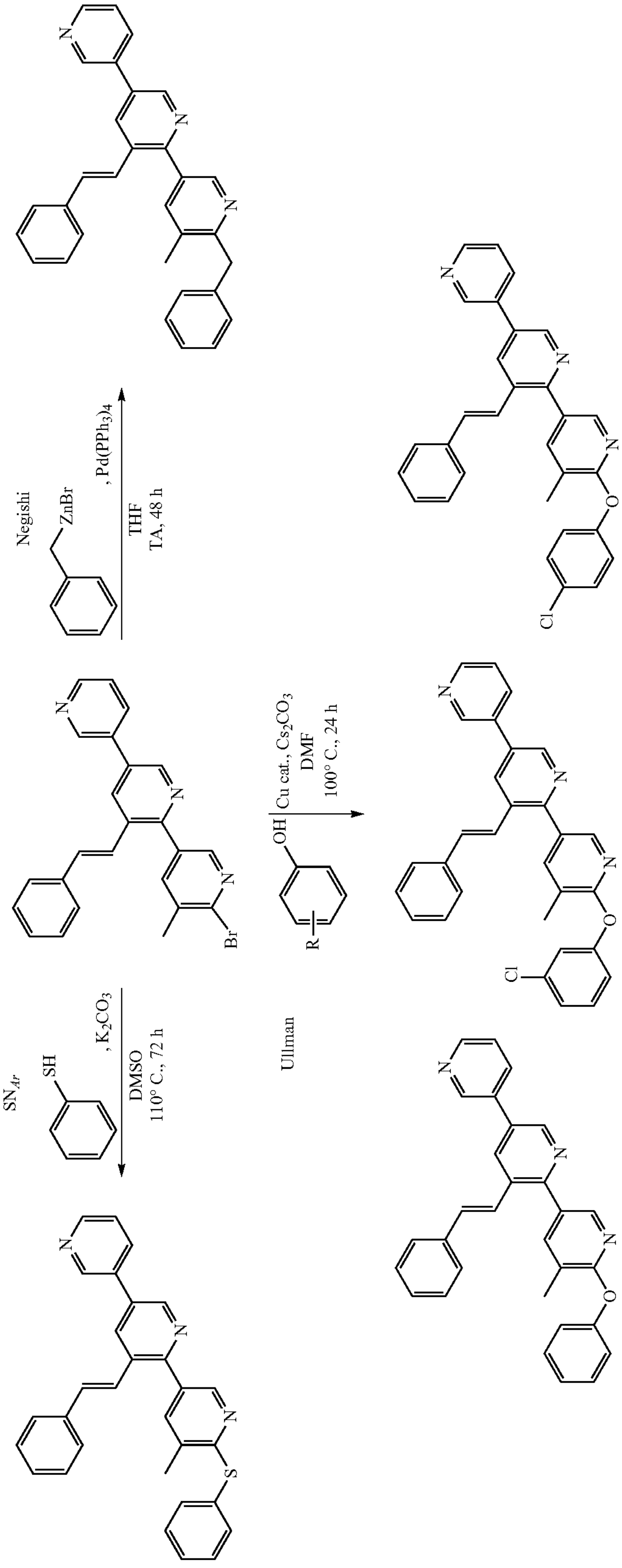
Key: Nucleophilic Aromatic Substitution ($SN_{Ar}$)
Ullman-type coupling reaction (Ullman)
Palladocatalyzed Negishi cross coupling reaction (Negishi)

General procedure for Nucleophilic Aromatic Substitution $SN_{Ar}$: To a reaction vessel containing (E)-6-bromo-5-methyl-3'-styryl-3,2':5',3"-terpyridine (1.0 equiv) in DMSO, benzenethiol (1.0 equiv) and $K_2CO_3$ (2.0 equiv) were added. The reaction mixture was stirred at 110° C. for 48 h, obtaining only 50% conversion of starting material. Benzenethiol (1.0 equiv) and $K_2CO_3$ (2.0 equiv) were recharged in the reaction mixture and reaction was completed after 24 h. The mixture was cooled to room temperature, quenched with water and extracted with DCM. The combined organic layers were washed with brine, dried over anhydrous magnesium sulfate, filtered and concentrated under reduced pressure to give the crude residue which was purified by column chromatography (DCM/MeOH 95/5 to 9/1).

General procedure for Ullman-type coupling reaction: To a reaction vessel containing (E)-6-bromo-5-methyl-3'-styryl-3,2':5',3"-terpyridine (1.0 equiv) in DMF, phenol (1.0 equiv), copper(0) powder (10%) and $Cs_2CO_3$ (3.0 equiv) were added. The reaction mixture was stirred at 100° C. for 24 h. The mixture was cooled to room temperature, quenched with NaOH 1 M solution and extracted with DCM. The combined organic layers were washed with brine, dried over anhydrous magnesium sulfate, filtered and concentrated under reduced pressure to give the crude residue which was purified by column chromatography (DCM/MeOH 98/2).

General procedure for palladocatalyzed Negishi cross coupling reaction: To a reaction vessel containing (E)-6-bromo-5-methyl-3'-styryl-3,2':5',3"-terpyridine (1.0 equiv) in dry THF under nitrogen atmosphere, benzylzinc(II) bromide 0.5 M (1.0 equiv) and tetrakis(triphenylphosphine) palladium(0) (10%) were added. The reaction mixture was stirred at rt for 48 h. The mixture was concentrated under reduced pressure to give the crude residue which was purified by column chromatography (DCM/MeOH 99/1 to 9/1).

Example 2: Biological Activity of Compounds of Formula (I)

Morphological Observation of the Cell Nuclei

After treatment, both detached and adherent cells are pooled after trypsinization, applied to a polylysine-coated glass slide by cytocentrifugation and fixed with a solution of ethanol/chloroform/acetic acid (6:3:1). The preparations are then incubated for 15 min at room temperature with 1 g/ml DAPI solution (Boehringer Mannheim-Roche, Mannheim, Germany), washed in distillated water, mounted under a coverslip in Mowiol (Calbiochem) and analyzed under a fluorescence microscope (BX51, Olympus, Rungis, France). Condensed and fragmented nuclei indicate the induction of apoptosis.

Target Expression and Apoptosis Induction Analysis by Western Blot

Cells are rinsed with ice-cold PBS, suspended in a lysis buffer [RIPA: NaCl 150 mM, Tris (pH 8) 50 mM, Triton X100 1%, PMSF 4 mM, EDTA 5 mM, NaF 10 mM, NaPPi 10 mM, Na3OV4 1 mM, aprotinin 0.5 µl/ml and 4.6 ml ultra-pure water] and incubated on ice for 30 min. Lysates are collected after centrifugation (13200 g, 10 min, 4° C.) and protein concentrations are determined using the Bradford assay (Bio-Rad, Hercules, USA). Equal amounts of protein (20 µg) are separated by SDS-PAGE on a 4-15% gradient polyacrylamide Mini-PROTEAN® TGX™ precast gel (Bio-Rad) and transferred to PDVF membranes (Bio-Rad). Membranes are blocked 1 h at room temperature with 5% (v/v) non-fat dry milk in TBS with 0.05% (v/v) Tween20 (T-TBS). Membranes are then incubated overnight at 4° C. with the appropriate antibodies, listed above. Membranes are then washed with T-TBS and incubated for 1 hour with the appropriate secondary antibody. Signals are revealed using Enhance ChemiLuminescence substrate (ECL) Prime Western Blot detection reagent (GE Healthcare Life Sciences) and the ImageQuant® Las4000 Series (GE Healthcare Life Sciences), and then quantified by pixel densitometry using the ImageJ® software. Antibodies used: anti-Mcl-1 (#5453), anti-Bcl-$x_L$ (#2764), anti-Caspase 3 (#9662), anti-PARP (#9542), (Cell Signaling Technology), anti-Actin (#MAB1501) (Merck Millipore) and anti-VHL (#GTX101087) (Genetex)

Apoptotic Events Quantification Using Flow Cytometry

Adherent and floating cells are pooled, washed with phosphated-buffered saline (PBS) and fixed with ethanol 70%. Cells are then centrifuged at 2000 r.p.m for 5 min and incubated for 30 min at 37° C. in PBS, to allow the release of low molecular weight DNA. Cell pellets are stained with propidium iodide using the DNA Prep Coulter Reagent Kit (Beckman Coulter). Samples are analyzed using Gallios flow cytometer (Beckman Coulter) and cell cycle distribution is determined using Gallios software (Beckman-Coulter).

Real Time Cell Activity Analysis (Impedancemetry, xCELLigence Technology)

Real-time growth curves monitoring is performed with the Real-Time Cell Analyzer Multi-Plate instrument, using the xCELLigence System (ACEA, Ozyme, Saint Quentin en Yvelines, France). This system monitors cellular events in real-time by measuring electrical impedance across interdigitated micro-electrodes integrated into the bottom surfaces of 96-well E-plates VIEW. These electrodes measure CI (Cell Index) based on impedance. CI correlates with the area of cells attached to the bottom of the plate. The CI values are displayed in the plot. Briefly, cells are plated in 96-well E-Plate View and placed onto the RTCA MP located inside a tissue culture incubator. The cells are left to grow for 24 h before treatment and impedance is continuously measured until the end of the treatment. Standard deviations of wells triplicates are analyzed with the RTCA 2.1.0 Software Real Time Cell Imaging Cells are seeded in 96-well plates in media. Cells are maintained at 37° C. and 5% $CO_2$ and monitored using an IncuCyte® S3 (Essen BioScience). IncuCyte® Caspase-3/7 Green Apoptosis Assay Reagent (Essen Bioscience) is added the next day following treatment and baseline images are taken using 10× objective. Fluorescent and phase-contrast images are acquired in real time every 1 hour from 2 separate regions per well. The Caspase 3/7 reagent labels dead cells yielding green fluorescence. The live-cell phase contrast images are used to calculate confluence using the IncuCyte® software, and to provide morphology information. Each experiment is done in triplicate and accumulation of caspase 3/7 over time is normalized to confluence of cells.

E3 ligases expression characterization by immunohistochemistry Immunohistochemistry using a Ventana Discovery XT autostainer is performed on 4 µm-thick paraffin sections. Slides are deparaffinized with EZPrep buffer and epitopes are unmasked by 15 min of high-temperature treatment in CC1 EDTA buffer. Sections are incubated for 40 min at 37° C. with an antibody directed against various E3 ligases, among which anti VHL (GTX101087) (Genetex). Secondary antibody (Omnimap Rabbit; Ventana Medical System Inc., Tucson, AZ, USA) is incubated for 16 min at room temperature. Immunodetection performed without the primary antibody is used as the control. After washes, the staining is performed with DAB and sections are counter-stained with hematoxylin using Ventana reagents according to the manufacturer's protocol. Stained slides are then digitized using an Aperio ScanScope slide scanner (Aperio Technologies, Vista, CA, USA).

Protein Quantitation by ELISA

The colorimetric ELISA assays allows quantitative analysis on target protein expression. A primary antibody targets the protein of interest. A second antibody recognizes the primary and conjugated to HRP allows a colorimetric detection. The kits used for ELISA assay can be OKAG00550 for Bcl-$x_L$ and OKAG00858 for Mcl-1, and procedures are applied according to the manufacturer's recommendations.

Results

Compounds of the invention induce proteolysis of Bcl-2, Mcl-1, Bcl-$x_L$, Bcl-w, Bfl-1 or Bcl-B protein, in particular of Bcl-2 protein, or Bcl-$x_L$ and/or Mcl-1 proteins.

Without being bound to any particular theory, it is believed that they recruit an E3 ligase to said target protein, which results in ubiquitination and subsequent degradation of the target protein by the proteasome.

Example 3: Synthesis of Other Compounds of the Invention

As depicted below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Synthetic Methods

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

All reactions are carried out under nitrogen or argon unless otherwise stated.

Analytical Instruments

| | |
|---|---|
| NMR | Bruker Avance III 400 MHz or Avance III HD 500 MHz |
| Infrared spectra | Perkin Elmer FT-IR |
| Melting point | Griffin apparatus |
| LC-MS | Waters SQ Detector as Mass Specrometer and Waters Alliance 2695 as separating module (column XBridge C18 2.5 mM/4.6 50 mM) |

All solvents an chemicals were use as purchased unless state otherwise. All N spectra were recorded on Bruker Avance III 400 MHz or Avance III HD 500 MHz spectrometers. $^1H$- and $^{13}C$ NMR spectra are reported as chemical shifts (6) in parts per million (ppm). Coupling constants (J) are reported in hertz (Hz) to the nearest one decimal point. The following abbreviations are used to describe multiplets: s (singlet), d (doublet), t (triplet), q (quartet), m (multiplet), br (broad). Infrared spectra were recorded as neat compound using a Perkin Elmer FT-IR spectrometer. Absorptions are reported in wavenumbers ($cm^{-1}$) and only peaks of interest are reported. Melting points of solids were measured with a Griffin apparatus. LC-MS was performed using a Waters SQ Detector as Mass Spectrometer and Waters Alliance 2695 as separating module (column XBridge C18 2.5 mM/4.6 50 mM) using the following gradients: A ($H_2O$ with 0.1% of $HCO_2H$)/B ($CH_3CN$ with 0.1% of $HCO_2H$) 95/5 to A/B 5/95 in 4.00 min. This ratio was held for 1.50 min before returning to the initial conditions for 0.50 min. Initial conditions were then maintained for 2.00 min. The retention times ($t_R$) of the molecules analysed are indicated in min. Unless otherwise specified, all reagents were obtained from commercial suppliers. Chromatography was carried out using flash silica gel 60 Merck (0.063-0.200 mm) as the stationary phase. Flash chromatography were performed using a Biotage Isolera One flash chromatography. The eluting solvent, indicated for each purifications, was determined by thin layer chromatography (TLC) performed using Merck 0.2 mm precoated plates of silica gel with Kieselgel 60 F264. The products were visualized using UV fluorescence (254 nm).

Building Block Synthetic Methods

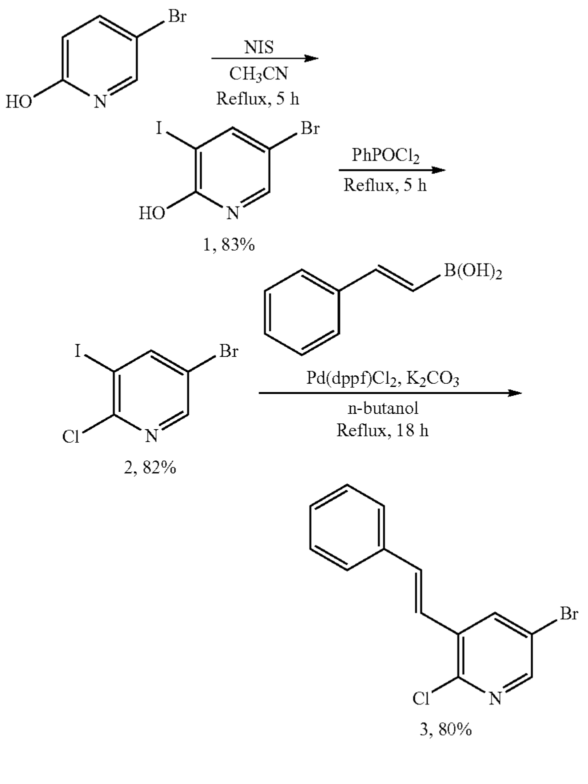

5-Bromo-3-iodopyridin-2-ol 1. To a round bottom flask containing 5-bromopyridin-2-ol (5.0 g, 28.7 mmol) in acetonitrile (120 mL), N-iodosuccinimide (7.1 g, 31.6 mmol, 1.1 equiv) was added. The solution was refluxed for 4 h, following the reaction by TLC. The suspension was cooled to room temperature and the solid was filtered and washed with MeOH to afford 7.1 g of 1 as a pink solid (83% yield).

Chemical Formula: $C_5H_3BrINO$; Molecular Weight: 299.89 g/mol; Melting Point: 63° C.

IR (KBr disc): 3490, 1630, 1607, 1522, 1457, 1309, 863, 683, 628 $cm^{-1}$.

$^1$H NMR ($CDCl_3$) δ 8.14 (d, J=2.5 Hz, 1H), 7.59 (d, J=2.5 Hz, 1H), 4.20 (br s, 1H, OH).

$^{13}$C NMR ($CDCl_3$) δ 171.5, 146.8, 145.9, 100.7, 92.9.

MS (ESI+): m/z 300.25 [$M+H^+$], 302.26 [$M^+$+2].

5-Bromo-2-chloro-3-iodopyridine 2. 5-Bromo-3-iodopyridin-2-ol 1 (9.0 g, 30.0 mmol) was dissolved in phenylphosphonic dichloride 90% (100 mL). The mixture was stirred and heated at 160° C. for 4 h, followed by TLC. The mixture was cooled down to room temperature and quenched by slow addition into a 1 L flask filled with ice and ammonia 28% (200 mL). The mixture was extracted with ethyl acetate, the organic layers were collected, washed with brine, dried over anhydrous magnesium sulfate, filtered, and concentrated under reduced pressure to give the crude residue which was purified by column chromatography (c-hexane/ethyl acetate 9/1) to afford 7.8 g of 2 as a white solid (82% yield).

Chemical Formula: $C_5H_2BrClIN$; Molecular Weight: 318.34 g/mol; Melting Point: 67° C.

IR (KBr disc): 3081, 3038, 1525, 1391, 1352, 1136, 1012, 890, 711, 515 $cm^1$.

$^1$H-NMR ($CDCl_3$) δ 8.40 (d, J=2.3 Hz, 1H), 8.29 (d, J=2.3 Hz, 1H).

$^{13}$C-NMR ($CDCl_3$) δ 153.2, 150.2, 149.6, 118.4, 95.3.

MS (ESI+): m/z 318.17 [$M+H^+$], 320.14 [$M^+$+2], 322.15 [M++4].

(E)-5-Bromo-2-chloro-3-styrylpyridine 3. To a reaction vessel containing 5-bromo-2-chloro-3-iodopyridine 2 (13.0 g, 40.8 mmol) in n-butanol (300 mL) under nitrogen atmosphere, (E)-styrylboronic acid (9.0 g, 61.2 mmol, 1.5 equiv), Pd(dppf)$Cl_2$-DCM (166 mg, 0.21 mmol, 0.5 mol %) and $K_2CO_3$ (11.3 g, 81.6 mmol, 2.0 equiv) were added. The mixture was stirred at reflux overnight. The mixture was cooled to room temperature, quenched with water and extracted with ethyl acetate. The organic layers were collected, washed with brine, dried over anhydrous magnesium sulfate, filtered and then, concentrated under reduced pressure to give the crude residue which was purified by column chromatography (c-hexane/ethyl acetate 99/1, then 98/2) to afford 9.6 g of 3 as a white solid (80% yield).

Chemical Formula: $C_{13}H_9BrClN$; Molecular Weight: 294.58 g/mol; Melting Point: 104° C.

IR (KBr disc): 3036, 1627, 1530, 1494, 1447, 1389, 1152, 1116, 1063, 956, 897, 755, 719, 687, 491 $cm^{-1}$.

$^1$H-NMR ($CDCl_3$) δ 8.35 (d, J=2.5 Hz, 1H, $H_{Pyr}$), 8.11 (d, J=2.5 Hz, 1H, $H_{Pyr}$), 7.57 (d, J=7.4 Hz, 2H, $H_{Ar}$), 7.42 (t, J=7.4 Hz, 2H, $H_{Ar}$), 7.38-7.34 (m, 1H, $H_{Ar}$), 7.27 (d, J=16.3 Hz, 1H, Ar—CH═CH—Pyr), 7.12 (d, J=16.3 Hz, 1H, Ar—CH═CH—Pyr).

$^{13}$C-NMR ($CDCl_3$) δ 148.6, 148.5, 136.7, 135.9, 134.6 (Ar—CH═CH—Pyr), 133.7, 129.1, 128.9 (2 $C_{Ar}$H), 127.1 (2 $C_{Ar}$H), 121.9 (Ar—CH═CH—Pyr), 119.3.

MS (ESI+): m/z 294.33 [$M+H^+$], 296.30 [$M^+$+2], 298.30 [M++4].

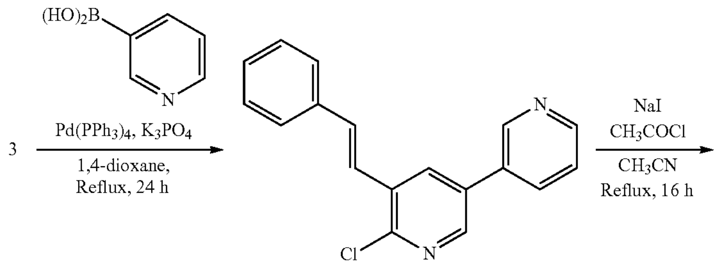

4, 80%

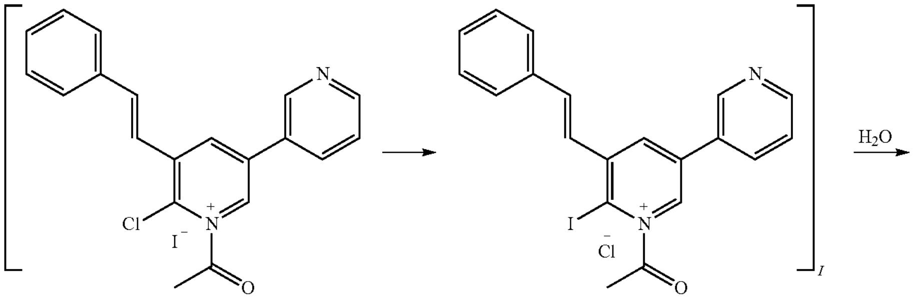

-continued

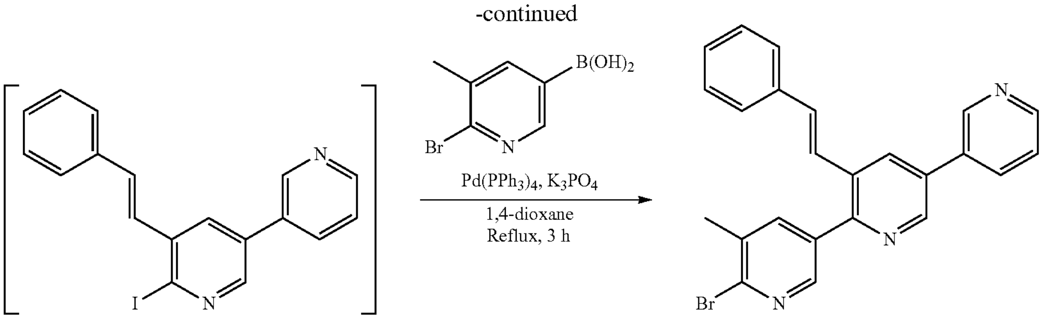

5

6, 45%

(E)-6-Cloro-5-styryl-3,3'-bipyridine 4. To a reaction vessel containing (E)-5-bromo-2-chloro-3-styrylpyridine 3 (3.8 g, 12.7 mmol) in 1,4-dioxane under nitrogen atmosphere, pyridin-3-ylboronic acid (1.7 g, 14.0 mmol, 1.1 equiv), tetrakis(triphenylphosphine)palladium(0) (734 mg, 0.64 mmol, 5 mol %) and $K_3PO_4$ (6.7 g, 31.8 mmol, 2.5 equiv) were added. The mixture was refluxed for 2 h, followed by TLC. The crude residue was purified by column chromatography (c-hexane/ethyl acetate 4/1 to 1/1) to afford 3.0 g of 4 as a white solid (80% yield).

Chemical Formula: $C_{18}H_{13}ClN_2$; Molecular Weight: 292.77 g/mol; Melting Point: 159° C.

IR (KBr disc): 3045, 3019, 2924, 2853, 1638, 1578, 1446, 1427, 1385, 1166, 1087, 1057, 1023, 951, 921, 804, 729, 714, 687 $cm^{-1}$.

$^1$H-NMR ($CDCl_3$) δ 8.90 (d, J=2.4 Hz, 1H, $H_{Pyr}$), 8.72 (dd, J=4.9, 1.6 Hz, 1H, $H_{Pyr}$), 8.51 (d, J=2.4 Hz, 1H, $H_{Pyr}$), 8.16 (d, J=2.4 Hz, 1H, $H_{Pyr}$), 7.95 (ddd, J=7.9, 2.4, 1.6 Hz, 1H, $H_{Pyr}$), 7.61-7.59 (m, 2H, $H_{Ar}$), 7.49-7.41 (m, 4H, $H_{Pyr}$, 3 HA, Ar—CH═CH—Pyr), 7.38-7.34 (m, 1H, $H_{Ar}$), 7.21 (d, J=16.3 Hz, 1H, Ar—CH═CH—Pyr).

$^{13}$C-NMR ($CDCl_3$) δ 150.0, 149.5, 147.9, 146.1, 136.2, 136.1, 134.7, 134.0 (Ar—CH═CH-Pyr), 132.9, 132.9, 132.5, 132.3, 128.9 (2 $C_{Ar}$H), 127.1 (2 $C_{Ar}$H), 123.9, 122.7 (Ar—CH═CH-Pyr).

MS (ESI+): m/z 293.35 [M+H$^+$], 295.34 [M++2].

(E)-6-Iodo-5-styryl-3,3'-bipyridine 5. To a solution of (E)-6-chloro-5-styryl-3,3'-bipyridine 4 (3.5 g, 12.1 mmol) in acetonitrile, NaI (4.5 g, 4.8 mmol, 2.5 equiv) and acetyl chloride (1.4 g, 18.1 mmol, 1.5 equiv) were added. The reaction mixture was refluxed for 16 h, affording 4.3 g of crude residue (80% of 5, by $^1$H-NMR) as a yellow solid which was used in the next reaction without further purification.

Chemical Formula: $C_{18}H_{13}1N_2$; Molecular Weight: 384.22 g/mol; Melting Point: 160° C.

IR (KBr disc): 3079, 3045, 3023, 2924, 1634, 1574, 1544, 1495, 1453, 1420, 1381, 1163, 1087, 1060, 1023, 959, 914, 805, 729, 712, 680 $cm^{-1216}$ $^1$H-NMR ($CDCl_3$) δ 8.89 (dd, J=2.4, 0.9 Hz, 1H, $H_{Pyr}$), 8.71 (dd, J=4.8, 1.7 Hz, 1H, $H_{Pyr}$), 8.46 (d, J=2.4 Hz, 1H, $H_{Pyr}$), 7.95 (d, J=2.4 Hz, 1H, $H_{Pyr}$), 7.93 (ddd, J=7.9, 2.4, 1.7 Hz, 1H, $H_{Pyr}$), 7.61-7.59 (m, 2H, $H_{Ar}$), 7.48-7.41 (m, 3H, 2$H_{Ar}$, Pyr-H), 7.38-7.34 (m, 2H, $H_{Ar}$), 7.29 (d, J=16.1 Hz, 1H, Ar—CH═CH—Pyr), 7.11 (d, J=16.1 Hz, 1H, Ar—CH═CH—Pyr). $^{13}$C-NMR ($CDCl_3$) δ 149.1, 148.0, 144.8, 140.7, 135.4, 135.2, 134.1, 133.4, 133.2, 132.9, 128.7 (2 $C_{Ar}$H), 128.0, 127.4, 126.4 (2 $C_{Ar}$H), 124.0, 115.9.

MS (ESI+): m/z 385.41 [M+H$^+$], 386.40 [M++1].

(E)-6-Bromo-5-methyl-3'-styryl-3,2':5',3"-terpyridine 6. To a reaction vessel containing (E)-6-iodo-5-styryl-3,3'-bipyridine 5 (1.5 g, 3.9 mmol) in 1,4-dioxane under nitrogen atmosphere, (6-bromo-5-methylpyridin-3-yl)boronic acid (930 mg, 4.3 mmol, 1.1 equiv), tetrakis(triphenylphosphine) palladium(0) (225 mg, 0.19 mmol, 5 mol %) and $K_3PO_4$ (2.0 g, 9.8 mmol, 2.5 equiv) were added. The mixture was refluxed for 4 h, followed by TLC. The crude residue was purified by column chromatography (c-hexane/ethyl acetate 95/5 to 4/1) to afford 751 mg of 6 as a yellow solid (45% yield).

Chemical Formula: $C_{24}H_{18}BrN_3$; Molecular Weight: 428.33 g/mol; Melting Point: 149° C.

IR (KBr disc): 3039, 1588, 1557, 1490, 1438, 1379, 1190, 1120, 1053, 1023, 970, 907, 804, 746, 708, 721, 686, 540 $cm^{-1}$.

$^1$H-NMR ($CDCl_3$) δ 8.96 (dd, J=2.4, 0.8 Hz, 1H, $H_{Pyr}$), 8.83 (d, J=2.2 Hz, 1H, $H_{Pyr}$), 8.72 (dd, J=4.8, 1.6 Hz, 1H, $H_{Pyr}$), 8.50 (d, J=2.4 Hz, 1H, $H_{Pyr}$), 8.21 (d, J=2.2 Hz, 1H, $H_{Pyr}$), 8.00 (dt, J=7.9, 2.0 Hz, 1H, $H_{Pyr}$), 7.92 (d, J=2.4 Hz, 1H, $H_{Pyr}$), 7.50-7.44 (m, 3H, 2$H_{Ar}$, $H_{Pyr}$), 7.40-7.29 (m, 3H, $H_{Ar}$), 7.22 (d, J=16.2 Hz, 1H, Ar—CH═CH—Pyr), 7.14 (d, J=16.2 Hz, 1H, Ar—CH═CH—Pyr), 2.49 (s, 3H, $CH_3$).

$^{13}$C-NMR ($CDCl_3$) δ 152.8, 149.8, 148.4, 148.1, 147.0, 145.0, 139.9, 136.4, 135.3, 134.7, 134.6, 133.5, 133.2, 133.1, 132.8, 132.2, 129.0 (2 $C_{Ar}$H), 128.8, 127.0 (2 $C_{Ar}$H), 124.5, 124.0, 22.2 ($CH_3$).

MS (ESI+): m/z 428.24 [M+H$^+$], 430.29 [M++2].

3

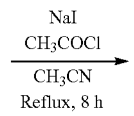

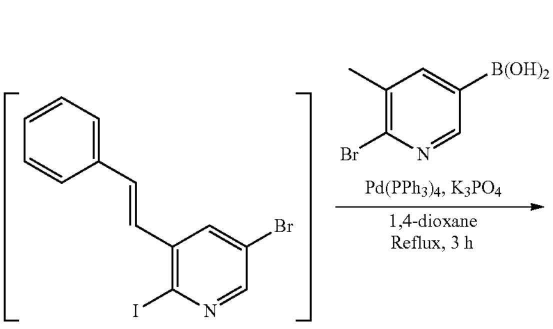

7

-continued

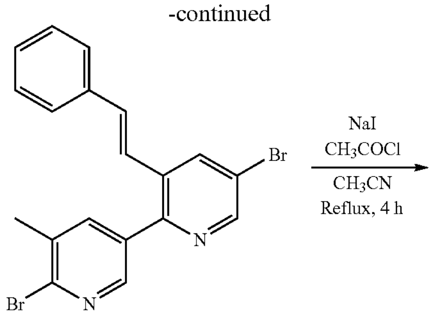

8, 55%

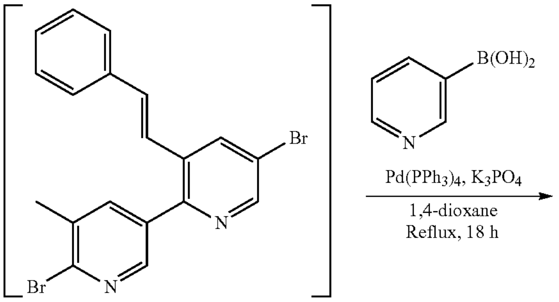

9

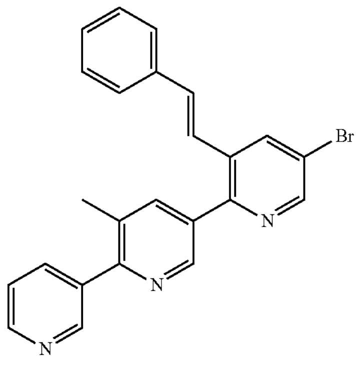

10, 60%

(E)-5-Bromo-2-iodo-3-styrylpyridine 7. To a reaction vessel containing (E)-5-bromo-2-chloro-3-styrylpyridine 3 (4.8 g, 16.3 mmol) in acetonitrile, NaI (6.1 g, 40.8 mmol, 2.5 equiv) and acetyl chloride (2.0 g, 24.5 mmol, 1.5 equiv) were added. The reaction mixture was refluxed for 12 h, affording 5.22 g of crude residue (80% of 7, by $^1$H-NMR) as yellow solid which was used in the next reaction without further purification.

Chemical Formula: $C_{13}H_9BrIN$; Molecular Weight: 386.03 g/mol; Melting Point: 78° C.

IR (KBr disc): 3054, 3023, 1629, 1492, 1446, 1377, 1269, 1109, 1026, 952, 889, 751 $cm^{-1}$.

$^1$H-NMR ($CDCl_3$) δ 8.29 (d, J=2.0 Hz, 1H, $H_{Pyr}$), 7.83 (d, J=2.0 Hz, 1H, $H_{Pyr}$), 7.52 (d, J=7.8 Hz, 2H, $H_{Ar}$), 7.38 (t, J=7.8 Hz, 2H, $H_{Ar}$), 7.32 (d, J=7.8 Hz, 1H, $H_{Ar}$), 7.09 (d, 1H, J=16.1 Hz, Ar—CH═CH—Pyr), 6.94 (d, J=16.1 Hz, 1H, Ar—CH═CH—Pyr).

$^{13}$C-NMR ($CDCl_3$) δ 149.6, 139.6, 135.9, 135.1, 134.7, 129.0, 128.9 (2 $C_{Ar}$H), 128.1, 127.1 (2 $C_{Ar}$H), 121.1, 120.8.

MS (ESI+): m/z 386.31 [M+H$^+$], 388.24 [M++2].

(E)-5,6'-Dibromo-5'-methyl-3-styryl-2,3'-bipyridine 8. To a reaction vessel containing (E)-5-bromo-2-iodo-3-styrylpyridine 7 (3.0 g, 7.7 mmol) in 1,4-dioxane under nitrogen atmosphere, (6-bromo-5-methylpyridin-3-yl)boronic acid (1.8 g, 8.4 mmol, 1.1 equiv), tetrakis(triphenylphosphine)palladium(0) (445 mg, 0.38 mmol, 5 mol %) and $K_3PO_4$ (4.1 g, 19.3 mmol, 2.5 equiv) were added. The mixture was refluxed for 4 h, followed by TLC. The crude residue was purified by column chromatography (c-hexane/ethyl acetate 99/1 to 95/5) to afford 1.8 g of 8 as a yellow solid (55% yield).

Chemical Formula: $C_{19}H_{14}Br_2N_2$; Molecular Weight: 430.14 g/mol; Melting Point: 143° C.

IR (KBr disc): 3031, 1393, 1111, 1050, 968, 898, 740, 685, 499 $cm^{-1}$.

$^1$H-NMR ($CDCl_3$) δ 8.65 (d, J=1.9 Hz, 1H, $H_{Pyr}$), 8.41 (d, J=1.9 Hz, 1H, $H_{Pyr}$), 8.17 (d, J=1.9 Hz, 1H, $H_{Pyr}$), 7.83 (d, J=1.9 Hz, 1H, $H_{Pyr}$), 7.42 (d, J=7.8 Hz, 2H, $H_{Ar}$), 7.36 (t, J=7.8 Hz, 2H, $H_{Ar}$), 7.31 (d, J=7.8 Hz, 1H, $H_{Ar}$), 7.12 (d, J=16.6 Hz, 1H, Ar—CH═CH—Pyr), 6.99 (d, J=16.6 Hz, 1H, Ar—CH═CH—Pyr), 2.46 (s, 3H, $CH_3$).

$^{13}$C-NMR ($CDCl_3$) δ 151.4, 149.4, 147.8, 144.9, 139.6, 136.5, 136.0, 135.2, 134.0, 133.9, 133.3, 128.9 (2 $C_{Ar}$H 128.8, 126.9 (2 $C_{Ar}$H), 123.4, 120.4, 22.0 ($CH_3$).

MS (ESI+): m/z 431.51 [M+H$^+$], 433.53 [M++2].

(E)-5-Bromo-6'-iodo-5'-methyl-3-styryl-2,3'-bipyridine 9. To a solution of (E)-5,6'-dibromo-5'-methyl-3-styryl-2,3'-bipyridine 8 (3.8 g, 8.9 mmol) in acetonitrile, NaI (3.3 g, 22.3 mmol, 2.5 equiv) and acetyl chloride (1.0 g, 13.4 mmol, 1.5 equiv) were added. The reaction mixture was refluxed for 8 h, affording 4.0 g of crude residue (90% of 9, by $^1$H-NMR) as yellow solid which was used in the next reaction without further purification.

Chemical Formula: $C_{19}H_{14}BrIN_2$; Molecular Weight: 477.14 g/mol; Melting Point: 147° C.

IR (KBr disc): 3029, 1576, 1449, 1428, 1389, 1112, 1089, 968, 900, 686, 498 $cm^{-1}$.

$^1$H-NMR ($CDCl_3$) δ 8.66 (d, J=2.3 Hz, 1H, $H_{Pyr}$), 8.38 (d, J=2.3 Hz, 1H, $H_{Pyr}$), 8.16 (d, J=2.3 Hz, 1H, $H_{Pyr}$), 7.73 (d, J=2.3 Hz, 1H, $H_{Pyr}$), 7.44 (d, J=7.4 Hz, 2H, $H_{Ar}$), 7.38 (t, J=7.4 Hz, 2H, $H_{Ar}$), 7.34-7.30 (m, 1H, $H_{Ar}$), 7.14 (d, J=16.2 Hz, 1H, Ar—CH═CH—Pyr), 6.98 (d, J=16.2 Hz, 1H, Ar—CH═CH—Pyr), 2.48 (s, 3H, $CH_3$).

13C-NMR ($CDCl_3$) δ 151.4, 149.5, 148.1, 139.2, 137.5, 136.5, 135.9, 134.0, 133.9, 133.3, 128.9 (2 $C_{Ar}$H), 128.8, 126.9 (2 $C_{Ar}$H), 125.6, 123.4, 120.4, 26.2 ($CH_3$).

MS (ESI+): m/z 477.48 [M+H$^+$], 479.54 [M++2].

(E)-5-Bromo-5'-methyl-3-styryl-2,3':6',3"-terpyridine 10. To a reaction vessel containing (E)-5-bromo-6'-iodo-5'-methyl-3-styryl-2,3'-bipyridine 9 (2.0 g, 4.2 mmol) in 1,4-dioxane under nitrogen atmosphere, pyridin-3-ylboronic acid (570 mg, 4.6 mmol, 1.1 equiv), tetrakis(triphenylphosphine)palladium(0) (243 mg, 0.2 mmol, 5 mol %) and $K_3PO_4$ (2.3 g, 10.5 mmol, 2.5 equiv) were added. The mixture was refluxed for 3 h, followed by TLC. The crude residue was purified by column chromatography (c-hexane/ethyl acetate 8/2 to 1/1) to afford 1.1 g of 10 as an off-white solid (60% yield).

Chemical Formula: $C_{24}H_{18}BrN_3$; Molecular Weight: 428.33 g/mol; Melting Point: 136-138° C.

IR (KBr disc): 3032, 2917, 1635, 1414, 1384, 1118, 950, 740, 541 $cm^{-1}$.

$^1$H-NMR ($CDCl_3$) δ 8.88 (dd, J=2.3, 0.9 Hz, 1H, $H_{Pyr}$), 8.78 (dd, J=2.1, 0.7 Hz, 1H, $H_{Pyr}$), 8.69 (d, J=2.2 Hz, 1H, $H_{Pyr}$), 8.68 (dd, J=4.9, 1.7 Hz, 1H, $H_{Pyr}$), 8.21 (d, J=2.1 Hz, 1H, $H_{Pyr}$), 7.97 (ddd, J=7.8, 2.3, 1.7 Hz, 1H, $H_{Pyr}$), 7.95 (dd, J=2.2, 0.8 Hz, 1H, $H_{Pyr}$), 7.45 (m, 3H, 2$H_{Ar}$, $H_{Pyr}$), 7.38-7.28 (m, 3H, $H_{Ar}$), 7.16 (d, J=16.2 Hz, 1H, Ar—CH═CH—Pyr), 7.11 (d, J=16.2 Hz, 1H, Ar—CH═CH—Pyr), 2.48 (s, 3H, $CH_3$).

$^{13}$C-NMR ($CDCl_3$) δ 155.5, 152.4, 149.9, 149.6, 149.3, 148.1, 139.9, 136.9, 136.6, 136.3, 133.9, 133.8 (Ar—CH═CH—Pyr), 133.6, 132.3, 131.4, 129.0 (2 $C_{Ar}$H), 128.9, 127.1 (2 $C_{Ar}$H), 123.8 (Ar—CH═CH—Pyr), 123.5, 120.4, 20.2 ($CH_3$).

MS (ESI+): m/z 428.74 [M+H$^+$], 430.62 [M$^+$+2].

HRMS (ESI): m/z Calcd. for $[M+H]^+$: 428.0762; Found: 428.0772.

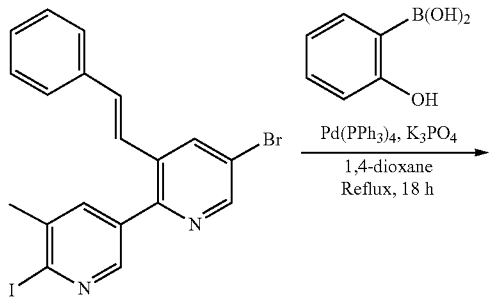

9

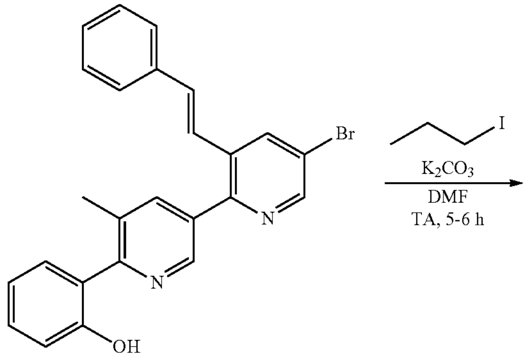

11 55%

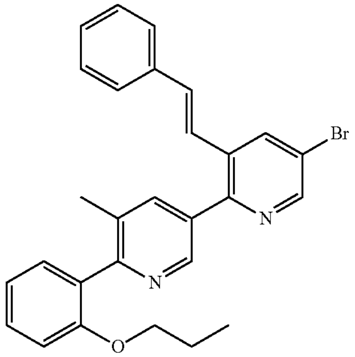

12 82%

(E)-5-bromo-6'-(2-hydroxyphenyl)-5'-methyl-3-styryl-2,3'-bipyridine 11. To a reaction vessel containing (E)-5-bromo-6'-iodo-5'-methyl-3-styryl-2,3'-bipyridine 9 (356 mg, 0.75 mmol, 1.0 equiv.) in 1,4-dioxane (20 mL) under nitrogen atmosphere, 2-hydroxyphenylboronic acid (120 mg, 0.83 mmol, 1.1 equiv.), tetrakis(triphenylphosphine)palladium(0) (43 mg, 0.04 mmol, 5 mol %) and $K_3PO_4$ (398 mg, 1.88 mmol, 2.5 equiv.) were added. The mixture was refluxed for 24 h, followed by TLC. The crude residue was purified by column chromatography (cyclohexane/ethyl acetate 100/0 to 90/10) to afford 183 mg of 11 as an off-white solid (55% yield).

Chemical formula: $C_{25}H_{19}BrN_2O$; Molecular weight: 443.34 g/mol

NMR $^1$H (400 MHz, $CDCl_3$): δ (ppm)=12.15 (s, 1H), 8.61 (dd, J=9.6, 2.2 Hz, 2H), 8.13 (d, J=2.2 Hz, 1H), 7.96 (d, J=2.2 Hz, 1H), 7.56 (dd, J=7.9, 1.7 Hz, 1H), 7.38 (d, J=6.9 Hz, 1H), 7.29 (t, J=7.4 Hz, 1H), 7.25 (d, J=7.0 Hz, 1H), 7.09 (d, J=16.2 Hz, 1H), 7.05-6.97 (m, 4H), 6.88 (td, J=7.6, 1.3 Hz, 1H), 2.59 (s, 3H).

NMR $^{13}$C (75 MHz, $CDCl_3$): δ (ppm)=157.98, 156.42, 151.84, 149.55, 144.98, 141.95, 136.62, 136.10, 133.78, 133.43, 132.61, 131.61, 130.89, 129.80, 128.99, 128.84, 126.93, 123.59, 121.24, 120.36, 118.56, 118.17, 21.94.

(E)-5-bromo-6'-(2-propoxyphenyl)-5'-methyl-3-styryl-2,3'-bipyridine 12. To a reaction vessel containing (E)-5-bromo-6'-(2-hydroxyphenyl)-5'-methyl-3-styryl-2,3'-bipyridine 11 (163 mg, 0.37 mmol, 1.0 equiv.) in DMF (10 mL), 1-iodopropane (54 µL, 0.55 mmol, 1.5 equiv.) and $K_2CO_3$ (102 mg, 0.74 mmol, 2 equiv.) were added. The reaction mixture was stirred at 50° C. for 17 h. The mixture was extracted with ethyl acetate. The combined organic layers were washed with brine, dried over anhydrous magnesium sulfate, filtered and concentrated under reduced pressure to give the crude residue which was purified by column chromatography (cyclohexane/ethyl acetate 100/0 to 90/10) to afford 147 mg of 12 as a yellow solid (82% yield).

Chemical formula: $C_{28}H_{25}BrN_2O$; Molecular weight: 485.43 g/mol NMR $^1$H (400 MHz, $CDCl_3$): δ (ppm)=8.65 (d, J=2.1 Hz, 1H), 8.62 (d, J=2.2 Hz, 1H), 8.14 (d, J=2.2 Hz, 1H), 7.77 (dd, J=2.2, 0.9 Hz, 1H), 7.39-7.35 (m, 2H), 7.34-7.21 (m, 5H), 7.07 (s, 2H), 7.00 (td, J=7.5, 1.0 Hz, 1H), 6.91 (dd, J=8.2, 1.0 Hz, 1H), 3.86 (t, J=6.5 Hz, 2H), 2.19 (s, 1H), 1.61 (h, J=7.3 Hz, 2H), 0.81 (t, J=7.4 Hz, 3H).

NMR $^{13}$C (75 MHz, $CDCl_3$): δ (ppm)=157.47, 156.16, 149.35, 147.06, 138.04, 136.33, 136.29, 133.37, 133.19, 132.86, 132.74, 130.59, 129.86, 129.66, 128.84, 128.60, 126.91, 124.10, 120.76, 112.06, 69.86, 22.59, 19.10, 10.59.

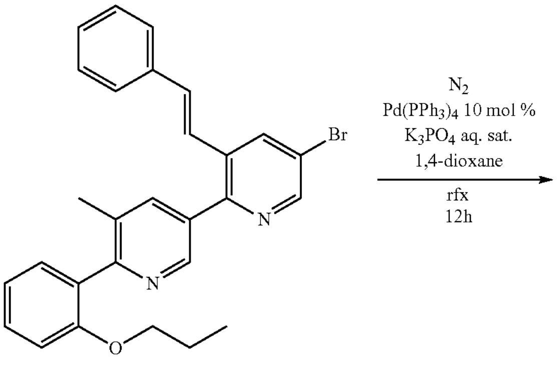

12

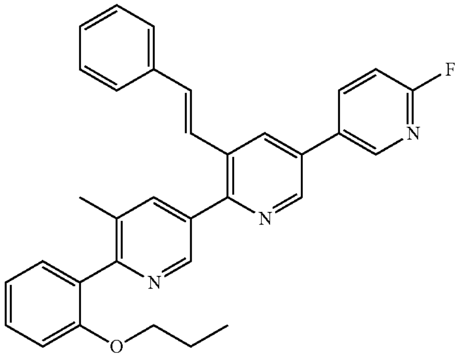

13 13%

(E)-6'-(2-propoxyphenyl)-5'-Methyl-5-(6-fluoropyridin-3-yl)-3-styryl-2,3':6',3"-terpyridine 13. To a reaction vessel containing (E)-5-bromo-6'-(2-propoxyphenyl)-5'-methyl-3-styryl-2,3'-bipyridine 12 (147 mg, 0.303 mmol) in 1,4-dioxane under nitrogen atmosphere, commercial 6-fluoro-pyridin-3-ylboronic acid (47 mg, 0.333 mmol, 1.1 equiv), tetrakis(triphenylphosphine)palladium(0) (35 mg, 0.03 mmol, 10 mol %) and $K_3PO_4$ (225 mg, 1.06 mmol, 3.5 equiv) were added. The mixture was refluxed for 26 h, followed by TLC. The crude residue was purified by column chromatography (dichloromethane/ethyl acetate 100/0 to 50/50) to afford 17 mg of 13 as an yellow oil (13% yield).

Chemical Formula: $C_{33}H_{28}FN_3O$ Molecular Weight: 501.61 g/mol $^1$H-NMR ($CDCl_3$): 8.76 (d, J=2.2 Hz, 1H), 8.73 (dd, J=2.1, 0.7 Hz, 1H), 8.50 (dt, J=2.7, 0.9 Hz, 1H), 8.13 (d, J=2.3 Hz, 1H), 8.04 (ddd, J=8.5, 7.5, 2.7 Hz, 1H), 7.85 (dd, J=2.2, 0.8 Hz, 1H), 7.44-7.35 (m, 2H), 7.22 (s, 6H), 7.14 (d, J=16.2 Hz, 1H), 7.06 (ddd, J=8.4, 3.0, 0.7 Hz, 1H), 7.01 (td, J=7.4, 1.0 Hz, 1H), 6.92 (d, J=8.1 Hz, 1H), 3.88 (t, J=6.5 Hz, 2H), 2.21 (s, 3H), 1.63 (dtd, J=13.9, 7.4, 6.5 Hz, 2H), 0.83 (t, J=7.4 Hz, 3H).

$^{13}$C-NMR ($CDCl_3$) 163.7 (d, J=240.9 Hz), 157.5, 156.2, 154.4, 147.2, 146.6, 146.1 (d, J=15.1 Hz), 139.9 (d, J=8.1 Hz), 138.2, 136.5, 133.2, 132.8, 132.4, 131.9, 131.6, 131.4 (d, J=4.7 Hz), 130.6, 129.9, 129.7, 128.9, 128.5, 126.9, 124.9, 120.8, 112.1, 110.1 (d, J=37.5 Hz), 69.9, 22.6, 19.1, 10.6.

$^{19}$F NMR (376 MHz, $CDCl_3$) δ (ppm) −68.49.

The final compound has been obtained from compound 12 as follows:

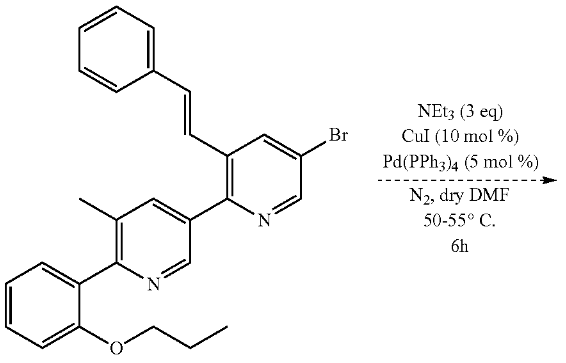

12

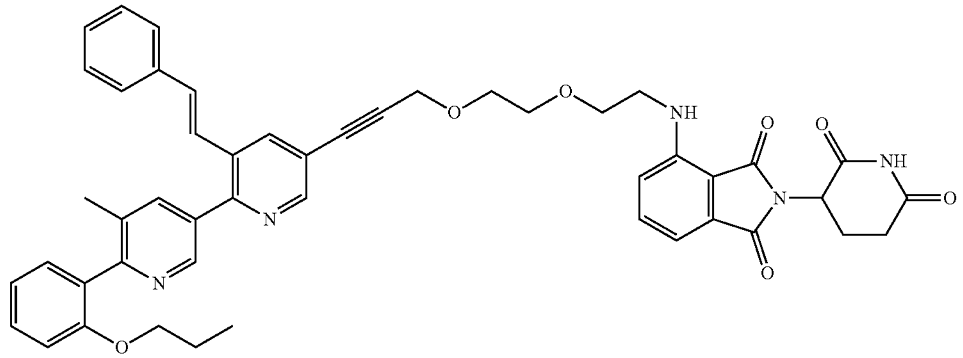

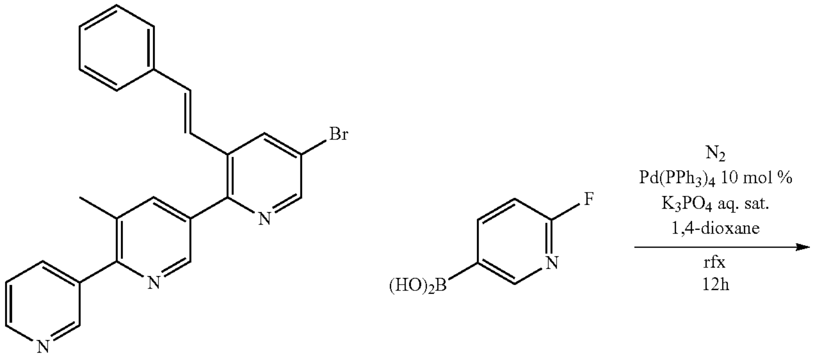

10

-continued

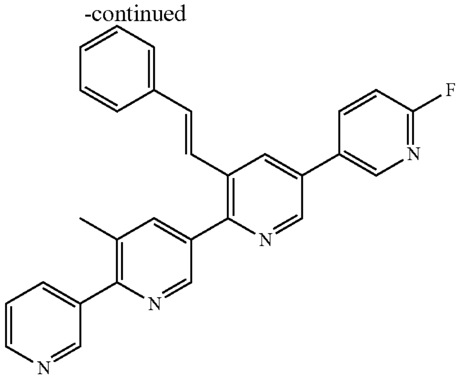

14 51%

(E)-5'-Methyl-5-(6-fluoropyridin-3-yl)-3-styryl-2,3':6',3"-terpyridine 14. To a reaction vessel containing (E)-5-bromo-5'-methyl-3-styryl-2,3':6',3"-terpyridine 10 (214 mg, 0.5 mmol) in 1,4-dioxane under nitrogen atmosphere, commercial 6-fluoropyridin-3-ylboronic acid (82 mg, 0.55 mmol, 1.1 equiv), tetrakis(triphenylphosphine)palladium(0) (58 mg, 0.05 mmol, 10 mol %) and $K_3PO_4$ (371 mg, 1.75 mmol, 3.5 equiv) were added. The mixture was refluxed for 12 h, followed by TLC. The crude residue was purified by column chromatography (dichloromethane/ethyl acetate 100/0 to 20/80) to afford 113 mg of 14 as an off-white solid (51% yield).

Chemical Formula: $C_{29}H_{21}FN_4$; Molecular Weight: 444.51 g/mol; Melting Point: 212° C.

NMR $^1$H (400 MHz, $CDCl_3$): δ (ppm)=8.85-8.83 (m, 1H), 8.79 (d, J=2.1 Hz, 1H), 8.77 (d, J=2.2 Hz, 1H), 8.62 (dd, J=4.9, 1.7 Hz, 1H), 8.53-8.48 (m, 1H), 8.13 (d, J=2.2 Hz, 1H), 8.05 (ddd, J=8.5, 7.5, 2.6 Hz, 1H), 7.96 (dd, J=2.2, 0.8 Hz, 1H), 7.92 (dt, J=7.9, 1.9 Hz, 1H), 7.44-7.35 (m, 3H), 7.33-7.27 (m, 2H), 7.27-7.21 (m, 1H), 7.18 (d, J=2.2 Hz, 1H), 7.06 (ddd, J=8.5, 3.1, 0.7 Hz, 1H), 2.44 (s, 3H).

NMR $^{13}$C (75 MHz, $CDCl_3$): δ (ppm)=163.75 (d, J=241.2 Hz), 155.41, 153.59, 149.92, 149.26, 148.10, 146.76, 146.14 (d, J=15.1 Hz), 139.99-139.75 (m), 136.53 (d, J=35.2 Hz), 134.09, 133.32, 132.59, 132.15, 131.90, 131.29, 131.23, 128.92, 128.67, 126.91, 124.60, 110.13 (d, J=37.5 Hz), 20.07.

NMR $^{19}$F (376 MHz, $CDCl_3$): δ (ppm)=−68.28

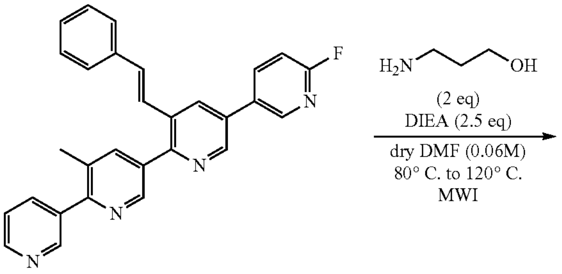

13

-continued

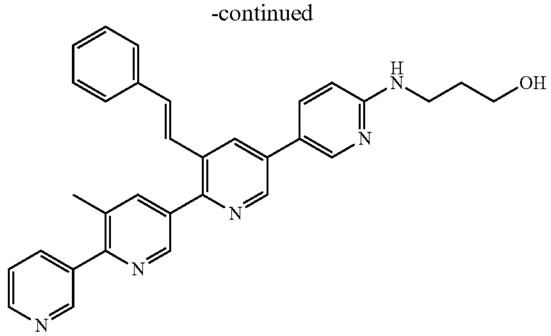

15 61%

(E)-5'-methyl-5-(6-(amino-propan-1-ol)pyridin-3-yl)-3-styryl-2,3':6',3"-terpyridine 15. The 3-aminopropan-1-ol (19 µL, 0.24 mmol, 2 equiv.) was dissolved in dry DMF and DIPEA (N,N-diisopropylethylamine) (52 µL, 0.3 mmol, 2.5 equiv). (E)-5'-methyl-5-(6-fluoropyridin-3-yl)-3-styryl-2,3':6',3"-terpyridine 14 (53 mg, 0.12 mmol, 1.0 equiv) was added, and the mixture was stirred at 120° C. under microwave irradiation for 5 h. After cooling to rt, the mixture was diluted with EtOAc and washed with water and brine. The organic layers were dried over $MgSO_4$, filtered and concentrated in vacuo. The crude residue was purified by column chromatography (EtOAc/MeOH 100/0 to 90/10) to afford 36 mg of 15 as an pale yellow solid (61% yield).

Aspect: yellow powder

Chemical Formula: $C_{32}H_{29}N_5O$; Molecular Weight: 499.62 g/mol

NMR $^1$H (400 MHz, $CDCl_3$): δ (ppm)=8.83 (d, J=2.3 Hz, 1H), 8.77 (d, J=2.1 Hz, 1H), 8.72 (d, J=2.2 Hz, 1H), 8.60 (dd, J=4.9, 1.7 Hz, 1H), 8.36 (d, J=2.5 Hz, 1H), 8.07 (d, J=2.3 Hz, 1H), 7.94 (d, J=2.1 Hz, 1H), 7.91 (dt, J=7.9, 2.1 Hz, 1H), 7.67 (dd, J=8.6, 2.5 Hz, 1H), 7.44-7.33 (m, 3H), 7.32-7.26 (m, 2H), 7.25-7.21 (m, 1H), 7.18 (d, J=15.9 Hz, 1H), 7.15 (d, J=16.5 Hz, 1H), 6.49 (d, J=8.6 Hz, 1H), 4.87 (t, J=6.4 Hz, 1H), 3.64 (t, J=5.5 Hz, 2H), 3.61-3.50 (m, 2H), 2.42 (s, 3H), 1.75 (p, J=5.8 Hz, 2H).

NMR $^{13}$C (75 MHz, $CDCl_3$): δ (ppm)=158.94, 150.00, 149.24, 148.14, 146.20, 146.07, 139.85, 136.69, 136.60, 136.06, 133.42, 132.71, 131.22, 131.17, 128.86, 128.43, 126.86, 125.05, 123.28, 108.72, 58.84, 38.09, 33.34, 20.05.

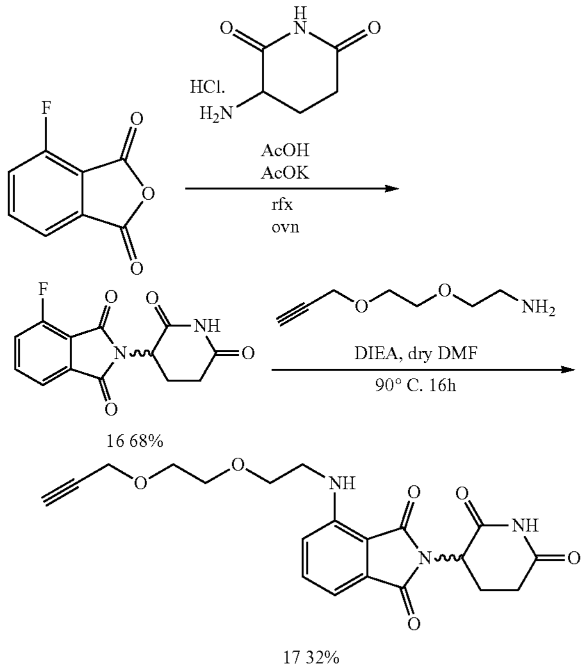

2-(2,6-dioxopiperidin-3-yl)-4-fluoro-2,3-dihydro-1H-isoindole-1,3-dione 16. In a round-bottom flask, commercial 3-fluorophthalic anhydride (171 mg, 1 mmol), commercial 3-aminopiperidine-2,6-dione hydrochloride (169 mg, 1 mmol), and sodium acetate (121 mg, 1.2 mmol) were mixed in AcOH (30 mL). The resulting reaction mixture was heated to reflux at 90° C. for 16 h. After cooling to room temperature, most of the AcOH was evaporated and the purple residue was dissolved in water (20 mL) then extracted with ethyl acetate (3x50 mL). The combined organic layer was dried (brine then $MgSO_4$) then concentrated under vacuo. The residue is purified by flash column chromatography with cyclohexane/ethyl acetate (50/50) to obtain the product as a pale blue solid (Yield: 68%).

Chemical formula: $C_{13}H_9FN_2O_4$; Molecular weight: 276.22 g/mol NMR $^1H$ (400 MHz, DMSO-d6): δ (ppm) =11.15 (s, 1H, NH), 7.99-7.92 (m, 1H, $H_6$), 7.80 (d, $^3J$=7.2 Hz, 1H, $H_7$), 7.77-7.72 (m, 1H, $H_5$), 5.16 (dd, $^3J_{ax-ax}$=12.8, $^3J_{ax-eq}$=5.4 Hz, 1H, $H_{3'}$), 2.96-2.84 (m, 1H, $H_{4'}$), 2.65-2.52 (m, 2H, $H_{4'}$, $H_{5'}$), 2.11-2.02 (m, 1H, $H_{5'}$) NMR $^{13}C$ (75 MHz, DMSO-d6): δ (ppm)=173.2 (C'), 170.2 ($C_2$'), 166.6 (d, $^3J_{CF}$=2.9 Hz, $C_3$), 164.4 ($C_1$), 157.3 (d, $^1J_{CF}$=262.4 Hz, $C_4$), 138.5 (d, $^3J_{CF}$=7.9 Hz, $C_6$), 133.9 (d, $^3J_{CF}$=1.2 Hz, $C_{7a}$), 123.5 (d, $^2J_{CF}$=19.6 Hz, $C_5$), 120.5 (d, $^4J_{CF}$=3.2 Hz, $C_7$), 117.5 (d, $^2J_{CF}$=12.7 Hz, $C_{3a}$), 49.5 ($C_{3'}$), 31.4 ($C_{4'}$), 22.3 ($C_5$')

NMR $^{19}F$ (MHz, DMSO-d6): δ (ppm)=−114.7

MS (ESI+): m/z: 308.90 $[M+MeOH+H]^+$, 638.52 $[M+2MeCN+2H]^2$+, 552.59 $[2M+H]^+$ 2-(2,6-dioxopiperidin-3-yl)-4-((2-(2-(prop-2-yn-1-yloxy)ethoxy)ethyl)amino) isoindoline-1,3-dione 17. In a round-bottom flask, 4-fluoro-thalidomide 16 (120 mg, 0.44 mmol), amine linker (75 μL, 0.53 mmol, 1.2 eq.), and DIEA (150 μL, 0.87 mmol, 3 eq.) in dry DMF (5 mL) were stirred at 90° C. for 16 h. The reaction mixture was diluted with 20 mL of ethyl acetate and the organic phase was washed with water (5x10 mL) then dried (brine, then $MgSO_4$) and evaporated under reduce pressure. The residue was purified by column chromatography using a gradient of ethyl acetate in cyclohexane (0% to 70%) to afford the product as a green solid (Yield: 32%).

Chemical formula: $C_{20}H_{21}N_3O_6$; Molecular weight: 399.40 g/mol

NMR $^1H$ (400 MHz, DMSO-d6): δ (ppm)=11.16 (s, 1H, $NH_a$), 7.64 (dd, $^3J$=8.5, $^3J$=7.2 Hz, 1H, $H_6$), 7.20 (d, J=8.6 Hz, 1H, $H_5$), 7.09 (d, J=7.2 Hz, 1H, $H_7$), 6.66 (t, $^3J$=5.6 Hz, 1H, $NH_b$), 5.11 (dd, $^3J_{ax-ax}$=12.9, $^3J_{ax-eq}$=5.5 Hz, 1H, $H_{3'}$), 4.19 (d, $^4J$=2.4 Hz, 2H, $H_{5''}$), 3.69-3.65 (m, 2H, $H_{2''}$), 3.65-3.60 (m, 4H, $H_{3''}$, $H_{4''}$), 3.53 (q, $^3J$=5.6 Hz, 2H, $H_{1''}$), 3.46 (t, $^4J$=2.4 Hz, 1H, $H_{7''}$), 2.99-2.88 (m, 1H, $H_{4'}$), 2.69-2.58 (m, 2H, $H_{4'}$, $H_{5'}$), 2.13-2.04 (m, 1H, $H_{5'}$).

NMR $^{13}C$ (75 MHz, DMSO-d6): δ (ppm)=172.9 ($C_{6'}$), 170.2 ($C_2$'), 169.0 ($C_3$), 167.3 ($C_1$), 146.4 ($C_4$), 136.3 ($C_6$), 132.1 ($C_{7a}$), 117.5 ($C_5$), 110.7 ($C_7$), 109.3 ($C_{3a}$), 80.4 ($C_{6''}$), 77.2 ($C_{7''}$), 69.5 ($C_{3''}$), 68.9 ($C_{2''}$), 68.6 ($C_{4'}$), 57.6 ($C_{5''}$), 48.6 ($C_{3'}$), 41.7 ($C_{1''}$), 31.0 ($C_{4'}$), 22.2 ($C_{5'}$)

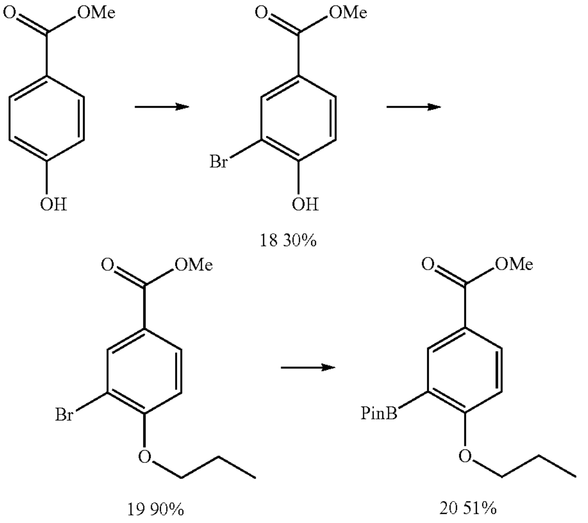

Methyl 3-bromo-4-hydroxybenzoate 18. To a solution of methyl 4-hydroxybenzoate (1 g, 6.57 mmol, 1.0 equiv.) in dry $CH_2Cl_2$ (75 mL) at room temperature was added carefully dibromide (0.33 mL, 65.7 mmol, 10.0 equiv.). The mixture was stirred at room temperature for 18 h. Then acetic acid (1 mL) was added and the reaction was stirred for 3 h more. The mixture was washed with saturated aqueous $Na_2S203$, brine, dried ($MgSO_4$) and concentrated under vaccuo. The resulting crude residue was purified by column chromatography ($CH_2Cl_2$/MeOH 100/0 to 99/1) to afford 592 mg of 18 as a white solid (39%).

Chemical Formula: $C_8H_7BrO_3$; Molecular Weight: 231.05 g/mol; Melting Point: 109° C.

NMR $^1H$ (400 MHz, $CDCl_3$): δ (ppm)=8.12 (d, J=2.1 Hz, 1H), 7.85 (dd, J=8.5, 2.0 Hz, 1H), 6.98 (d, J=8.5 Hz, 1H), 5.90 (s, 1H), 3.83 (s, 3H).

NMR $^{13}C$ (75 MHz, $CDCl_3$): δ (ppm)=165.6, 156.2, 134.0, 131.1, 124.1, 115.8, 110.1, 52.2.

Methyl 3-bromo-4-propoxybenzoate 19. To a solution of methyl 3-bromo-4-hydroxybenzoate 18 (462 mg, 2 mmol, 1.0 equiv.) in dry acetone (20 mL) at room temperature were added 1-iodopropane (0.29 mL, 3 mmol, 1.5 equiv.) and $K_2CO_3$ (553 mg, 4 mmol, 2 equiv.). After cooling to room temperature, the mixture was diluted with EtOAc and washed with water, brine, dried ($MgSO_4$) and concentrated under vaccuo to afford 492 mg of 19 as a pale yellow oil (90%).

Chemical Formula: $C_{11}H_{13}BrO_3$; Molecular Weight: 273.13 g/mol

NMR $^1H$ (400 MHz, $CDCl_3$): δ (ppm)=8.14 (d, J=2.1 Hz, 1H), 7.86 (dd, J=8.6, 2.1 Hz, 1H), 6.79 (d, J=8.7 Hz, 1H), 3.96 (t, J=6.4 Hz, 2H), 3.81 (s, 3H), 1.80 (h, J=7.3 Hz, 3H), 1.01 (t, J=7.4 Hz, 3H).

NMR $^{13}C$ (75 MHz, $CDCl_3$): δ (ppm)=165.80, 159.09, 134.76, 130.51, 123.38, 111.83, 111.81, 70.76, 52.11, 22.38, 10.51

Methyl 3-(4,4,5,5-tetramethyl-1,3,2-dioxaborolan-2-yl)-4-(propoxy) benzoate 20. To a reaction vessel containing Methyl 3-bromo-4-propoxybenzoate 19 (492 mg, 1.74 mmol, 1.0 equiv.) in 1,4-dioxane (3.5 mL) under nitrogen atmosphere, commercial bis(pinacolato)diboron (664 mg, 2.62 mmol, 1.5 equiv.), bis(triphenylphosphine)palladium (II) dichloride (250 mg, 0.35 mmol, 2 mol %) and KOAc (514 mg, 5.23 mmol, 3.0 equiv.) were added. The mixture was refluxed for 24 h, followed by TLC. The crude residue was purified by column chromatography (cyclohexane/ethyl acetate 100/0 to 80/20) to afford 285 mg of 20 as a white solid (51% yield).

Chemical Formula: $C_{17}H_{25}BO_5$; Molecular Weight: 320.19 g/mol; Melting Point: 87° C.

NMR $^1H$ (400 MHz, $CDCl_3$): δ (ppm)=8.22 (d, J=2.4 Hz, 1H), 7.99 (dd, J=8.7, 2.4 Hz, 1H), 6.77 (d, J=8.8 Hz, 1H), 3.91 (t, J=6.2 Hz, 2H), 3.80 (s, 3H), 1.83-1.71 (m, 2H), 1.19 (s, 12H), 1.01 (t, J=7.4 Hz, 3H).

NMR $^{13}C$ (75 MHz, $CDCl_3$): δ (ppm)=167.2, 166.9, 138.1, 134.4, 121.8, 110.6, 83.5, 69.8, 51.8, 25.0, 22.6, 10.5.

$^{11}B$ NMR (128 MHz, $CDCl_3$) δ (ppm): 30.73.

10

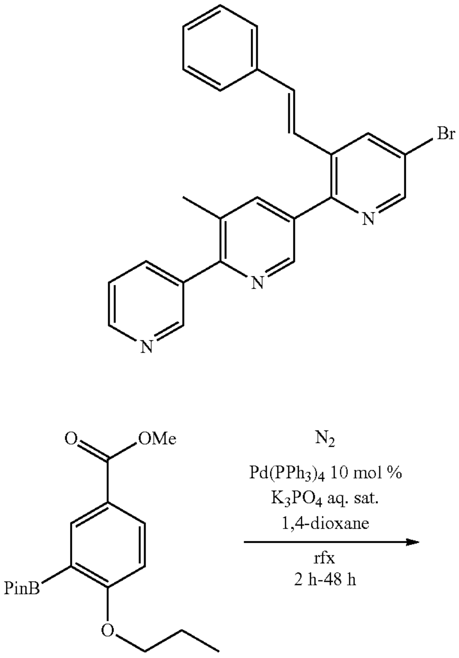

20

-continued

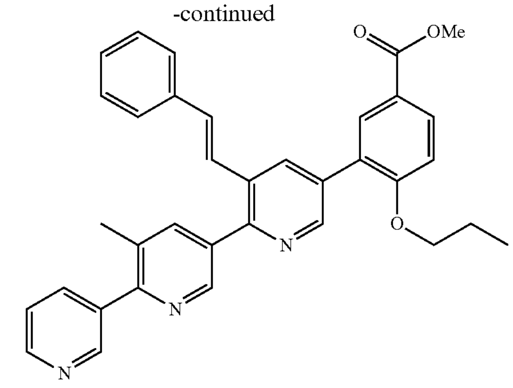

21 17%

(E)-5'-Methyl-5-(methyl 4-(propoxy)benzoate)-3-styryl-2,3':6',3"-terpyridine 21. To a reaction vessel containing (E)-5-Bromo-5'-methyl-3-styryl-2,3':6',3"-terpyridine 10 (209 mg, 0.49 mmol, 1.0 equiv.) in 1,4-dioxane (20 mL) under nitrogen atmosphere, methyl 3-(4,4,5,5-tetramethyl-1,3,2-dioxaborolan-2-yl)-4-(propoxy) benzoate 20 (235 mg, 0.73 mmol, 1.5 equiv.), tetrakis(triphenylphosphine)palladium(0) (5.48 mg, 0.025 mmol, 5 mol %) and $K_3PO_4$ (363 mg, 1.71 mmol, 3.5 equiv.) were added. The mixture was refluxed for 19 h, followed by TLC. The crude residue was purified by column chromatography (c-hexane/ethyl acetate 8/2 to 1/1) to afford 45 mg of 21 as a white solid (17% yield).

Chemical Formula: $C_{35}H_{31}N_3O_3$; Molecular Weight: 541.24 g/mol

NMR $^1H$ (400 MHz, $CDCl_3$): δ (ppm)=8.85-8.83 (m, 1H), 8.81-8.77 (m, 2H), 8.64-8.59 (m, 1H), 8.20 (d, J=2.1 Hz, 1H), 8.09 (d, J=2.2 Hz, 1H), 8.04 (dd, J=8.7, 2.2 Hz, 1H), 7.97 (dd, J=2.2, 0.8 Hz, 1H), 7.92 (dt, J=7.8, 1.9 Hz, 1H), 7.42-7.35 (m, 3H), 7.32-7.26 (m, 2H), 7.25-7.22 (m, 1H), 7.20 (d, J=15.8 Hz, 1H), 7.12 (d, J=16.2 Hz, 1H), 7.00 (d, J=8.6 Hz, 1H), 4.03 (t, J=6.4 Hz, 2H), 3.87 (s, 3H), 2.43 (s, 3H), 1.87-1.71 (m, 2H), 0.99 (t, J=7.4 Hz, 3H).

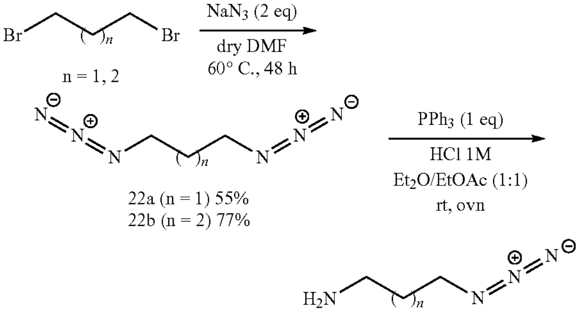

Nucleophilic Substitution:

1,3-diazidopropane 21a and 1,4-diazidobutane 22b. Alkyl diazides were obtained by a trivial nucleophilic displacement reaction between the proper alkyl dihalide and sozium azide, according to the following procedure. The proper dibromoalkyle (10.0 mmol, namely 2.02 g of 1,3-dibromopropane) was dissolved in dry DMF (10 mL) under nitrogen and $NaN_3$ (1.30 g, 20.0 mmol) was added. The mixture was kept under magnetic stirring at 60° C. for 24 h.

The reaction mixture was then poured into water (50 mL) and extracted five times with diethyl ether (50 mL each). The organic extracts were washed with water (5 mL) then dried (brine, then $MgSO_4$). The reaction mixture was evaporated under reduced pressure to yield crude oily products.

22a. Chemical formula: $C_3H_6N_6$; Molecular weight: 126.12 g/mol; Aspect: colorless oil Yield: 55%

NMR $^1H$ (400 MHz, DMSO-d6): δ (ppm)=3.42 (t, $^3J$=6.7 Hz, 4H, $H_1$, $H_3$), 1.77 (p, $^3J$=6.7 Hz, 2H, $H_2$)

NMR $^{13}C$ (75 MHz, DMSO-d6): δ (ppm)=48.5 ($C_1$, $C_3$), 28.1 ($C_2$)

22b. Chemical formula: $C_4H_8N_6$; Molecular weight: 140.15 g/mol; Aspect: colourless oil Yield: 77%

NMR $^1H$ (400 MHz, DMSO-d6): δ (ppm)=3.40-3.28 (m, 4H, $H_1$, $H_4$), 1.76-1.66 (m, 4H, $H_2$, $H_3$)

NMR $^{13}C$ (75 MHz, DMSO-d6): δ (ppm)=50.9 ($C_1$, $C_4$), 26.2 ($C_2$, $C_3$)

3-azidopropylamine 23a and 4-azidobutylamine 23b. Azidoalkylamines were obtained by a regioselective Staudinger reduction of diazide compounds 22. To a mixture of diazidoalkyl compound 22 (10 mmol) cooled to 0° C., aqueous 1M HCl (20 mL), diethyl ether (7 mL), and ethyl acetate (7 mL) was added. Triphenylphosphine was added portionwise during 30 min. The mixture was warmed to rt and stirred for an additional 20 h, and then the organic layer was separated from the aqueous layer. The aqueous phase was washed with ethyl ether (2×50 mL) to remove triphenylphosphine oxide residual. The aqueous phase was basified to a pH 13 by aqueous NaOH and then was extracted with dichloromethane (3*100 mL). The combined dichloromethane layer was dried over $MgSO_4$ and concentrated to yield 4-azidoalkylamine derivative as an oil.

23a. Chemical formula: $C_3H_8N_4$; Molecular weight: 100.12 g/mol; Aspect: yellow oil Yield: 52%

NMR $^1H$ (400 MHz, DMSO-d6): δ (ppm)=3.38 (t, $^3J$=6.7 Hz, 2H, $H_1$), 2.59 (t, $^3J$=6.7 Hz, 2H, $H_3$), 1.59 (p, $^3J$=6.7 Hz, 2H, $H_2$)

NMR $^{13}C$ (75 MHz, DMSO-d6): δ (ppm)=48.9 ($C_3$), 39.2 ($C_1$), 32.6 ($C_2$)

23b. Chemical formula: $C_4H_{10}N_4$ Molecular weight: 114.15 g/mol; Aspect: yellow oil Yield: 54%

NMR $^1H$ (400 MHz, DMSO-d6): δ (ppm)=3.23 (t, $^3J$=6.8 Hz, 2H, $H_1$), 2.67 (t, $^3J$=6.9 Hz, 2H, $H_3$), 1.65-1.53 (m, 2H, $H_2$), 1.51-1.44 (m, 2H, $H_4$).

NMR $^{13}C$ (75 MHz, DMSO-d6): δ (ppm)=51.4 ($C_4$), 41.7 (CI), 30.8 ($C_2$), 26.3 ($C_3$).

Synthesis of One of the Preferred Compounds: CRBN-PBM1-001

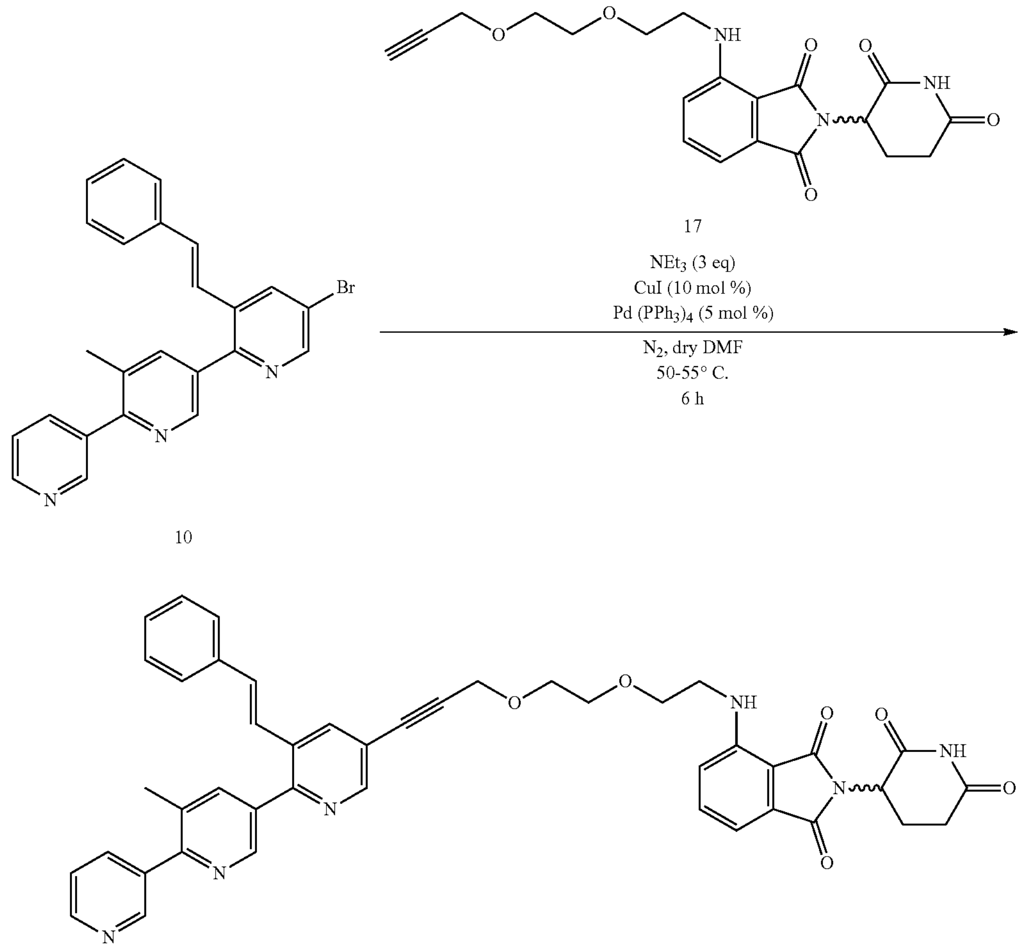

CRBN-PBM1-001 55%

CRBN-PBM1-001 was obtained by a Sonogashira cross-coupling reaction. Under inert atmosphere, triethylamine (42 μL, 0.3 mmol, 3.0 equiv.), copper (I) iodide (2 mg, 0.01 mmol, 10% mol), 2-(2,6-dioxopiperidin-3-yl)-4-((2-(2-(prop-2-yn-1-yloxy) ethoxy)ethyl)amino)isoindoline-1,3-dione 17 (44 mg, 0.11 mmol, 1.1 equiv) and tetrakis(triphenylphosphine)palladium(0) (8 mg, 0.005 mmol, 5% mol) were added to a solution of 10 (42.8 mg, 0.10 mmol, 1.0 equiv) in dry DMF (2 mL). The reaction mixture was stirred at 50° C. for 6 h. The mixture was diluted with ethyl acetate. The aqueous layers were washed with 4 mL of a saturated solution of $NaHCO_3$ and with brine. The combined organic layers were dried over anhydrous magnesium sulfate, filtered and concentrated under reduced pressure. The crude residue was purified by flash chromatography on silica gel column (water/acetonitrile 100/0 to 0/100) to afford 41 mg of CRBN-PBM1-001 as a solid yellow (55% yield).

Chemical formula: $C_{44}H_38N_6O_6$; Molecular weight: 746.82 g/mol

NMR $^1H$ (400 MHz, $CDCl_3$): δ (ppm)=8.82 (s, 1H), 8.75-8.66 (m, 2H), 8.64-8.58 (m, 3H), 8.14 (d, J=2.2 Hz, 1H), 8.03 (d, J=1.9 Hz, 1H), 7.94-7.84 (m, 3H), 7.69-7.60 (m, 1H), 7.43-7.33 (m, 4H), 7.31-7.20 (m, 3H), 7.09-6.99 (m, 3H), 6.85 (d, J=8.5 Hz, 1H), 6.45 (t, J=5.5 Hz, 1H), 4.83 (dd, J=12.1, 5.4 Hz, 1H), 4.44 (s, 1H), 3.81-3.64 (m, 4H), 3.43 (q, J=5.5 Hz, 1H), 2.82-2.57 (m, 2H), 2.40 (s, 3H), 2.06-1.97 (m, 1H).

NMR $^{13}C$ (75 MHz, $CDCl_3$): δ (ppm)=171.2, 169.3, 168.5, 167.6, 155.4, 150.8, 149.9, 149.9, 149.5, 149.3, 149.3, 148.0, 147.9, 146.8, 139.9, 139.8, 136.9, 136.69, 136.65, 136.5, 136.4, 136.2, 136.1, 135.8, 133.9, 133.7, 133.3, 132.5, 131.4, 131.3, 128.9, 128.9, 128.8, 128.6, 126.9, 126.9, 124.2, 123.7, 123.3, 119.2, 116.8, 111.7, 89.3, 82.9, 70.6, 69.6, 69.5, 59.3, 48.9, 42.4, 31.5, 22.8, 20.0, 20.0.

MS (ESI+): m/z: 373.93 $[M+2H]^{2+}$, 748.36 $[M+H]^+$

Example 4: Further Biological Activity of Compounds of the Invention

Material and Methods

Cell Culture and Drug Testing

Human platinum resistant ovarian carcinoma cells IGROV1-R10 were used. This cell line was grown in RPMI 1640 medium supplemented with 2 mM Glutamax™, 25 mM HEPES, 10% fetal calf serum, and 33 mM sodium bicarbonate (Fisher Scientific, Illkirch, France). Cells were maintained at 37° C. in a humid atmosphere with 5% $C_{O2}$. Cells were seeded in 25 $cm^2$ flasks. After 24 h, exponentially growing cells were exposed to 1 μM of compounds for 24 h. CRBN-PBM1-001 targeting both Mcl-1 and CRBN and Pyridoclax were designed and synthetized by the CERMN (Centre d'Etudes et de Recherche sur le Médicament de Normandie) and dissolved in DiMethyl SulfOxide (DMSO, Sigma-Aldrich).

Target Expression Analysis by Western Blot

Cells were rinsed with ice-cold PBS, suspended in a lysis buffer [RIPA: NaCl 150 mM, Tris (pH 8) 50 mM, Triton X100 1%, PMSF 4 mM, EDTA 5 mM, NaF 10 mM, NaPPi 10 mM, Na3VO4 1 mM, aprotinin 0.5 μL/mL and 4.6 mL ultra-pure water] and incubated on ice for 30 min. Lysates were collected after centrifugation (13200 g, 10 min, 4° C.) and protein concentrations were determined using the Bradford assay (Bio-Rad, Hercules, USA). Equal amounts of protein (25 μg) were separated by SDS-PAGE on a 4-15% gradient polyacrylamide Mini-PROTEAN®TGX™ precast gel (Bio-Rad). PVDF membranes were activated through a 1 minute 100% ethanol bath and then equilibrated with transfer buffer (3:1:1 ultra-pure water, ethanol 100%, 5× transfer buffer [Bio-Rad]). Proteins were then transferred to activated PDVF membranes (Bio-Rad). Membranes were blocked 1 hour at room temperature with 5% (v/v) non-fat dry milk in TBS with 0.05% (v/v) Tween20 (T-TBS). Membranes were then incubated overnight at 4° C. with the appropriate antibodies, listed below. Membranes were then washed with T-TBS and incubated for 1 hour with the appropriate secondary antibody. Signals were revealed using Enhance ChemiLuminescence substrate (ECL Prime) Western Blot detection reagent (GE Healthcare Life Sciences) and the ImageQuant®Las4000Series (GE Healthcare Life Sciences). The relative intensities of the protein bands were quantified using the ImageJ software, and the values were normalized to the intensities of the respective Actin signals.

The following antibodies were used: anti-Actin (1/2000, #MAB1501, Merck Millipore), anti-CRBN (1/1000, ab230411, Abcam), anti-Mcl-1 (1/1000, #5453), anti-Bcl-$x_L$ (1/1000, #2764), anti-rabbit polyclonal secondary antibody (1/2000, #7074S) (Cell Signaling Technology) and anti-mouse polyclonal secondary antibody (1/2000, #NA931V-ML, Amersham).

RESULTS

The presence of CRBN was confirmed by western blot in IGROV1-R10 cells as shown in FIG. 1.

The effect of the CRBN-PBM1-001 molecule targeting both Mcl-1 and CRBN was characterized in order to demonstrate its ability to target and degrade Mcl-1. Western blot experiments showed that a 24 h exposure to Pyridoclax (1 μM) as single agent did not modulate Mcl-1 expression in IGROV1-R10 cells. In contrast, CRBN-PBM1-001 was able to induce a 52% decrease of Mcl-1 expression after a 24 h exposure at a concentration of 1 μM as evidenced by densitometry analysis (FIG. 2). Moreover, in these experimental conditions, the observed effect was only exerted on Mcl-1, since Bcl-$x_L$ expression was not affected by the exposure to the CRBN-PBM1-001 and Bcl-2 is not expressed in these cells. These results thus show that CRBN-PBM1-001 is able to bind to Mcl-1 and to initiate its degradation.

What is claimed is:

1. A compound of following formula (I):

(I)

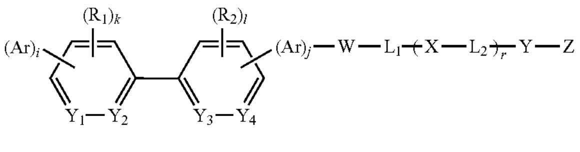

Wherein:

$Y_1$, $Y_2$, $Y_3$ and $Y_4$ are each independently C or N, $Y_1$ and $Y_2$ being such as one is N and the other is C, $Y_3$ and $Y_4$ being such as one is N and the other is C;

$Ar_1$, $Ar_2$ are each independently selected from $(C_6-C_{10})$ aryl, (5 to 7 membered) heteroaryl, —O—$(C_6-C_{10})$aryl, —O-(5 to 7 membered) heteroaryl, —S—$(C_6-C_{10})$aryl, —S-(5 to 7 membered) heteroaryl, —$(C_1-C_6)$alkyl-$(C_6-C_{10})$aryl, —$(C_1-C_6)$alkyl-(5 to 7 membered) heteroaryl and halogens, the aryl and heteroaryl groups being optionally substituted by one to three $R_3$ groups, i and j are independently 0 or 1, and $R_1$, $R_2$, are at each occurrence, independently selected from $(C_1\text{-}C_6)$alkyl, $(C_6\text{-}C_{10})$aryl, —$(C_1\text{-}C_6)$alkyl-$(C_6\text{-}C_{10})$aryl, —$(C_2\text{-}C_6)$alkenyl-$(C_6\text{-}C_{10})$aryl, -carbonyl-$(C_6\text{-}C_{10})$aryl-, -carbonyl-$(C_1\text{-}C_6)$alkyl-$(C_6\text{-}C_{10})$aryl, C(═O)H, COOH, OH, said alkyl groups being optionally substituted by OH, said aryl groups being optionally substituted by one to three $R_4$ groups;

k and l are independently 0 or 1;

at least one of $(R_1)_k$ and $(R_2)_l$ being such as:

$R_1$ is selected from $(C_0\text{-}C_{10})$aryl, —$(C_1\text{-}C_6)$alkyl-$(C_6\text{-}C_{10})$aryl, —$(C_2\text{-}C_6)$alkenyl-$(C_6\text{-}C_{10})$aryl, -carbonyl-$(C_6\text{-}C_{10})$aryl-, -carbonyl-$(C_1\text{-}C_6)$alkyl-$(C_6\text{-}C_{10})$aryl, and k is 1; or $R_2$ is selected from $(C_6\text{-}C_{10})$aryl, —$(C_1\text{-}C_6)$alkyl-$(C_6\text{-}C_{10})$aryl, —$(C_2\text{-}C_6)$alkenyl-$(C_6\text{-}C_{10})$aryl, -carbonyl-$(C_6\text{-}C_{10})$aryl-, -carbonyl-$(C_1\text{-}C_6)$alkyl-$(C_6\text{-}C_{10})$aryl, and l is 1;

$R_3$ is, at each occurrence, independently selected from $(C_1\text{-}C_6)$alkyl, $(C_1\text{-}C_6)$alkoxy, OH, C(═O)H, $(CH_2)_m$ $CONR_aR_b$, $C({=}O)R_c$, $(CH_2)_nCO_2H$, $(CH_2)_nCO_2R_c$, $(CH_2)_pCN$, $(CH_2)_qC({=}N(OH))NH_2$, —$SO_2NR_aR_b$, I, Cl, Br, F, $(C_6\text{-}C_{10})$aryl, a (5 to 7 membered) heteroaryl, —$(C_1\text{-}C_6)$alkyl-$(C_6\text{-}C_{10})$aryl, —$(C_2\text{-}C_6)$alkenyl-$(C_6\text{-}C_{10})$aryl, said alkyl groups being optionally substituted by a OH, $(C_1\text{-}C_6)$alkoxy and/or —O—$(C_6\text{-}C_{10})$aryl group;

$R_4$ is, at each occurrence, independently selected from $(C_1\text{-}C_6)$alkyl, $(CH_2)_nCO_2H$, $(CH_2)_nCO_2R_c$, I, Cl, Br, F, or there are two $R_4$ groups that form with the aryl to which they are bound a naphthyl;

$R_a$ and $R_b$ are independently chosen from H and $(C_1\text{-}C_6)$ alkyl;

$R_c$ is chosen from H and $(C_1\text{-}C_6)$alkyl;

m is 0, 1, 2, 3;

n is 0, 1, 2, 3;

p is 0, 1, 2, 3;

q is 0, 1, 2, 3;

r is 0 or 1;

W and Y are each independently selected from a single bond, —CH═CH—, —C≡C—, —NH—, —$NR_5$—, —O—, —S—, —C(═O)NH—, —NHC(═O)—, —C(═O)O—, —OC(═O)—;

$R_5$ is, at each occurrence, independently selected from $(C_1\text{-}C_6)$alkyl, $L_1$ and $L_2$ are each independently selected from $(C_1\text{-}C_{18})$ alkyl, $(C_2\text{-}C_{18})$alkenyl, and $(C_2\text{-}C_{18})$alkynyl groups, said groups being optionally interrupted by one or more groups selected from —O—, —S—, —$NR_6$—;

$R_6$ is, at each occurrence, independently selected from H and $(C_1\text{-}C_6)$alkyl, X is selected from (5 to 7 membered) heteroaryl, —NH—, —$NR_7$—, —O—, —S—, —C(═O)NH—, —NHC(═O)—, —C(═O)O—, —OC(═O)—;

$R_7$ is selected from $(C_1\text{-}C_6)$alkyl,

Z is a E3 ubiquitin ligase ligand;

or a stereoisomeric form, a mixture of stereoisomeric forms and a pharmaceutically acceptable salt form thereof.

2. The compound according to claim 1, of following formula (II):

(II)

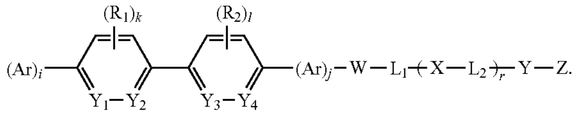

3. The compound according to claim 1, of following formula (IIIa) or (IIIb):

(IIIa)

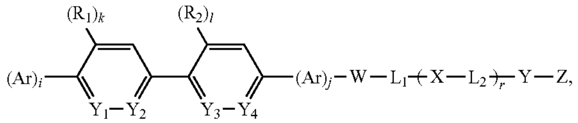

(IIIb)

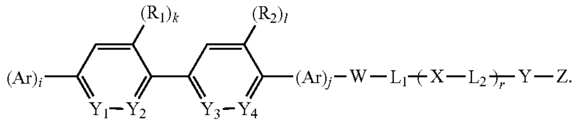

4. The compound according to claim 1, wherein $Ar_1$ and/or $Ar_2$ are selected from phenyl, pyridyl, pyrimidyl, imidazolyl, pyrazolyl, thiophenyl, triazolyl.

5. The compound according to claim 1, wherein at least one of $Ar_1$, $Ar_2$ is a 5 to 7 membered heteroaryl containing a nitrogen atom.

6. The compound according to claim 1, wherein $R_1$ and $R_2$ are independently selected from $C_1\text{-}C_6$ alkyl and $(C_6\text{-}C_{10})$ aryl $(C_2\text{-}C_6)$alkenyl.

7. The compound according to claim 1, wherein $R_1$ is 5-methyl, and/or $R_2$ is 5-styryl or 2-(naphthalen-2-yl) vinyl; or $R_2$ is 5-methyl, and/or $R_1$ is 5-styryl or 2-(naphthalen-2-yl) vinyl.

8. The compound according to claim 1, of following formula (IVa) or (IVb):

(IVa)

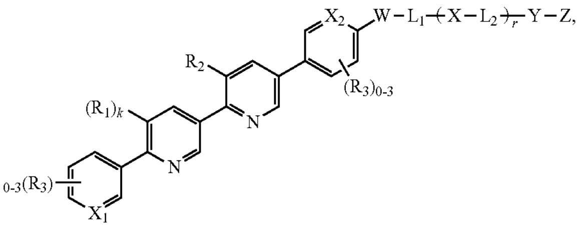

(IVb)

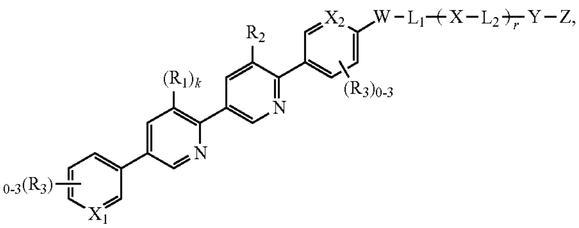

wherein:
$X_1$, $X_2$, are at each occurrence, independently selected from C or N;
$R_1$, $R_2$, $R_3$ are independently, at each occurrence as defined in claim 1.
9. The compound according to claim 1, of one of the following formulae:
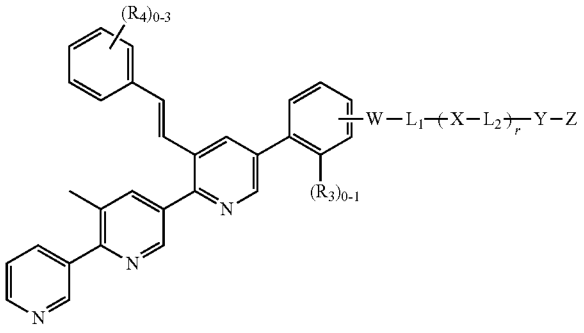
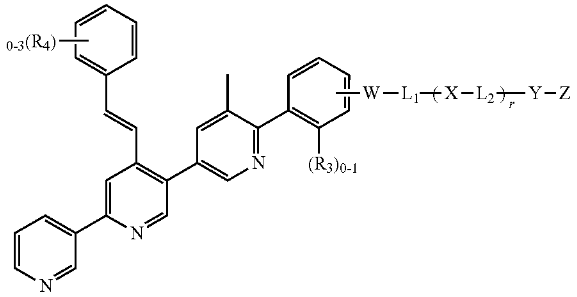
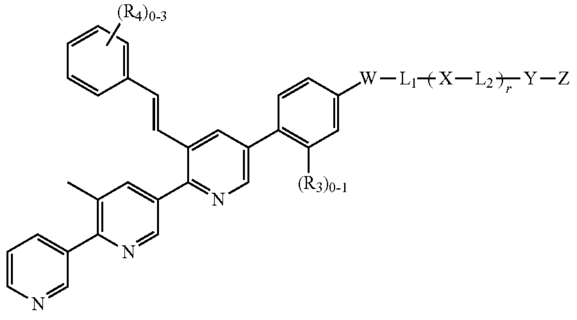
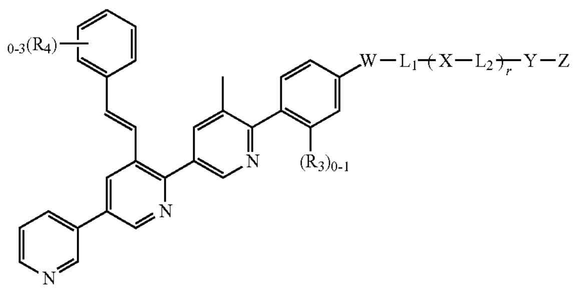
-continued
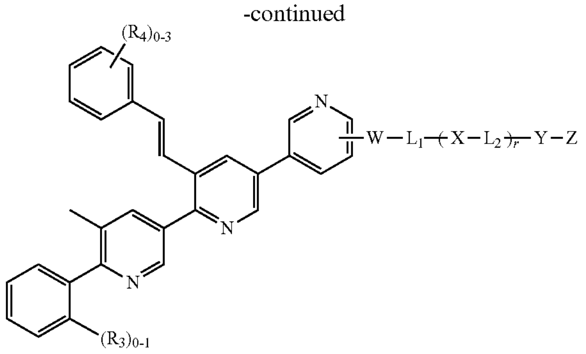
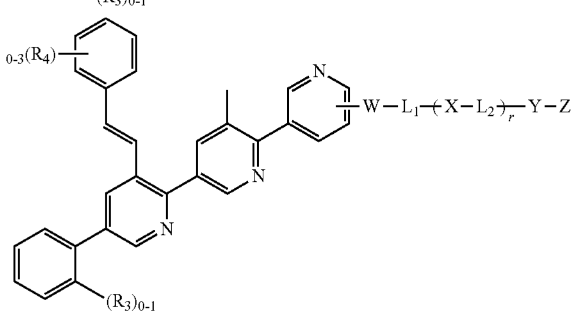
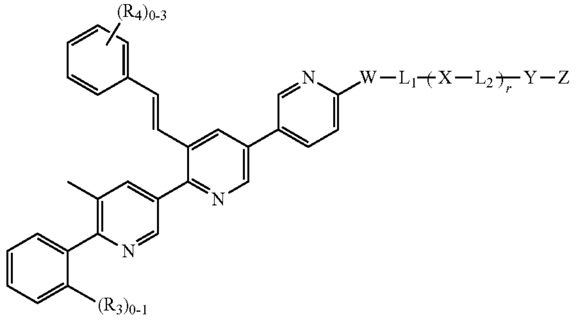
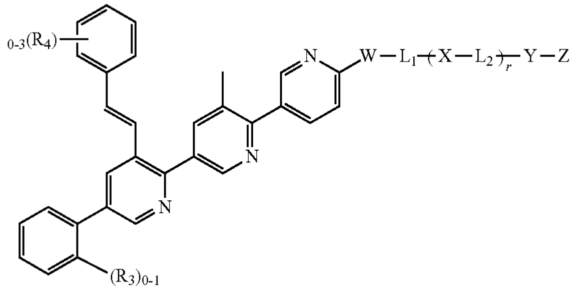
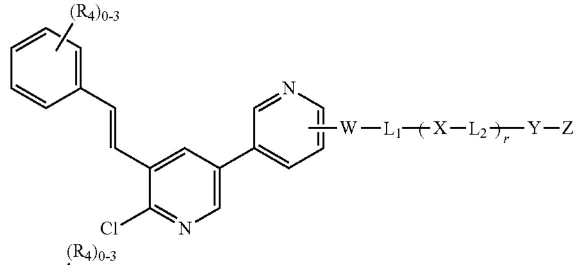
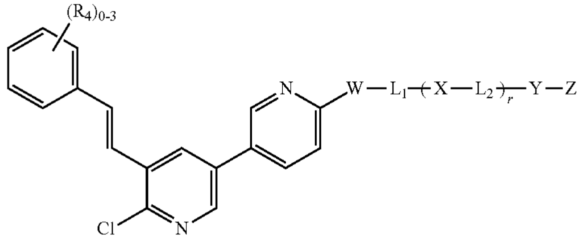

-continued

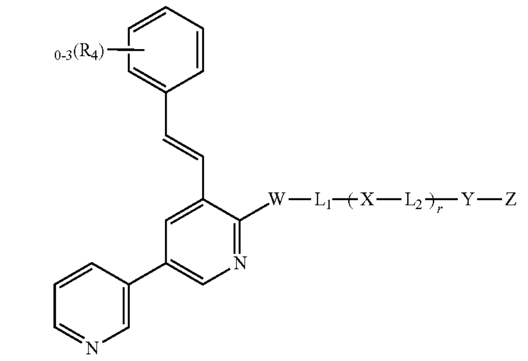

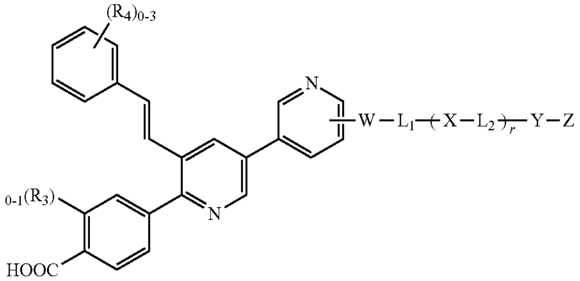

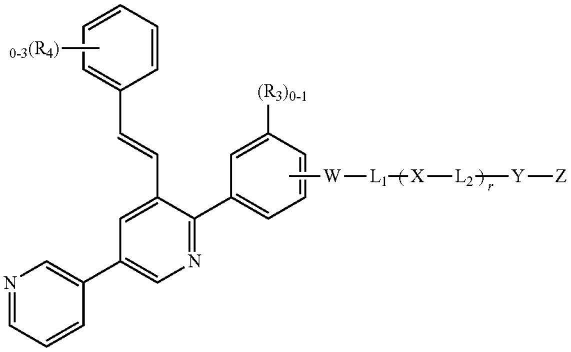

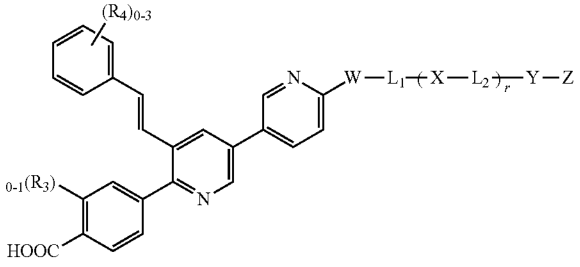

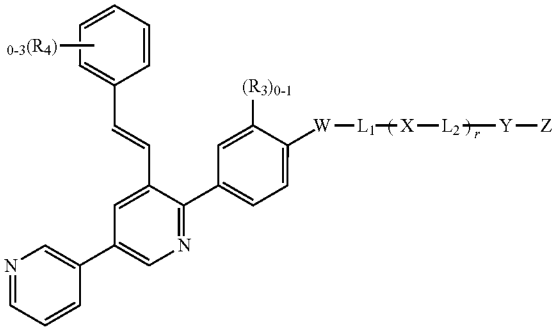

wherein:

$R_3$ and $R_4$ are independently, at each occurrence as defined in claim 1.

10. The compound according to claim 1, wherein:

W is —NH—, $L_1$ is $(C_1\text{-}C_{18})$alkyl, r is 1, X is a (5 to 7 membered) heteroaryl, $L_2$ is a $(C_1\text{-}C_{18})$alkyl interrupted by one or more-O-atoms, and Y is a single bond, —NH— or —C(═O)NH—; or W is —NH—, $L_1$ is a $(C_1\text{-}C_{18})$alkyl interrupted by one or more-O-atoms, r is 0 and Y is a single bond or —C(═O)NH—.

11. The compound according to claim 1, wherein Z is selected from:

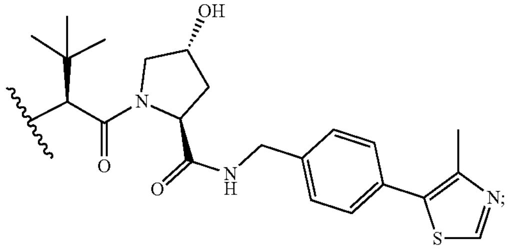

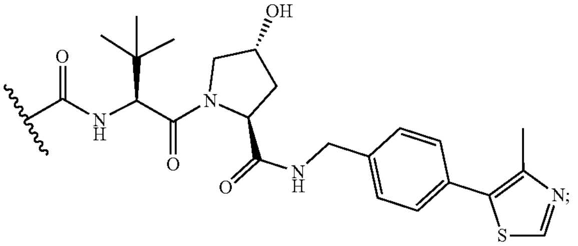

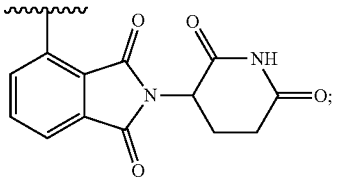

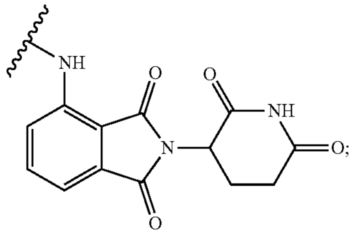

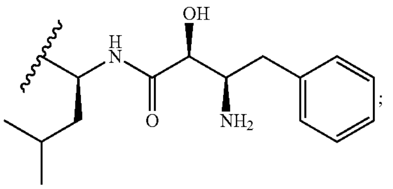

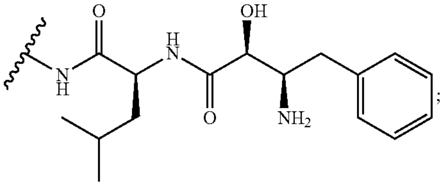

-continued

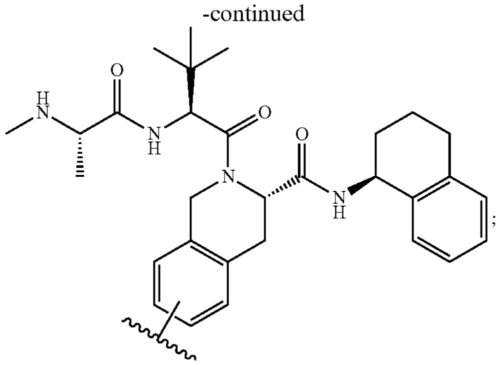

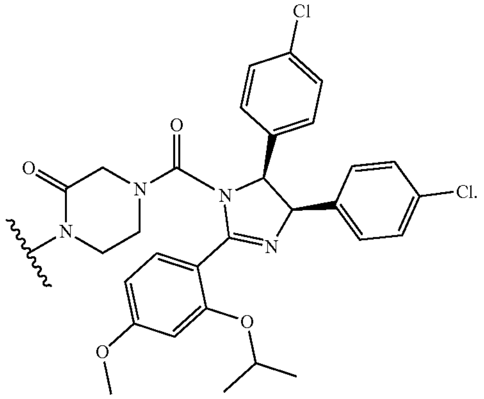

12. The compound according to claim 1, wherein said compound is:

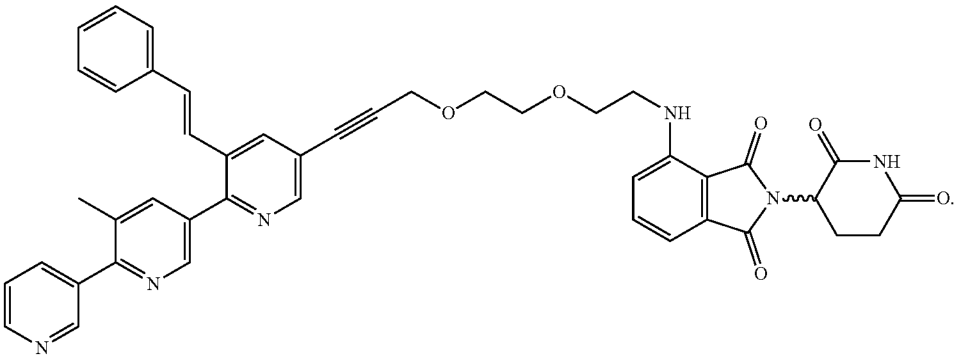 [SMILES: Cc1cc(-c2ncc(C#CCOCCOCCNc3cccc4c3C(=O)N(C3CCC(=O)NC3=O)C4=O)cc2/C=C/c2ccccc2)cnc1-c1cccnc1]

(IIIa1)

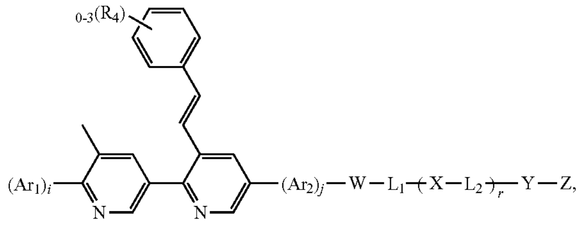

(IIIa2)

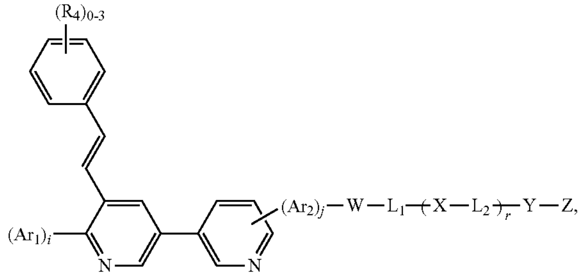

13. A pharmaceutical composition comprising a compound of formula (I) as defined in claim 1, in admixture with at least one pharmaceutically acceptable excipient or carrier, and optionally further comprising an additional anti-cancer agent.

14. A method of treating cancer, comprising administering to a patient in need thereof an effective amount of pharmaceutical composition comprising a compound of formula (I) according to claim 1.

15. The compound according to claim 1, of following formula (IIIa1) or (IIIa2), (IIIb1) or (IIIb2):

-continued (IIIb1)

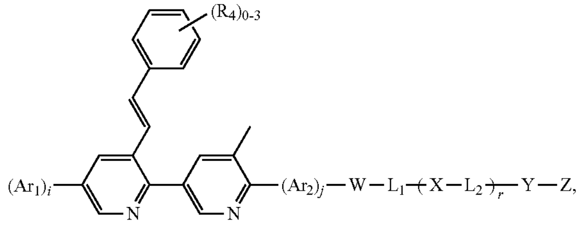

-continued (IIIb2)

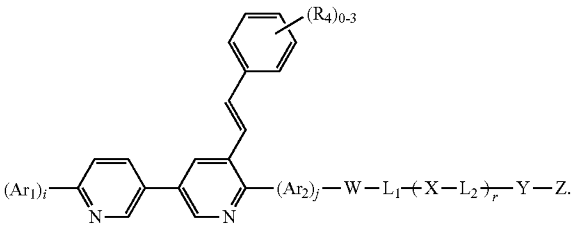

16. The compound according to claim 1, of following formula (IVa1), (IVa2), (IVb1) or (IVb2):

(IVa1)

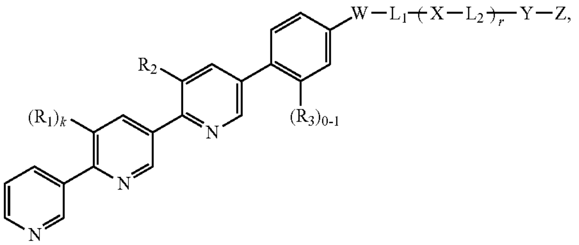

(IVb2)

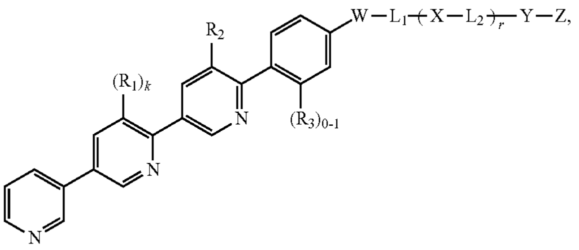

-continued (IVa3)

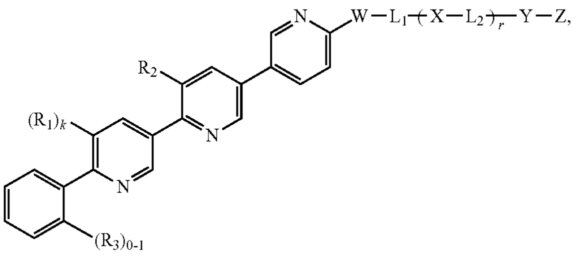

(IVb2)

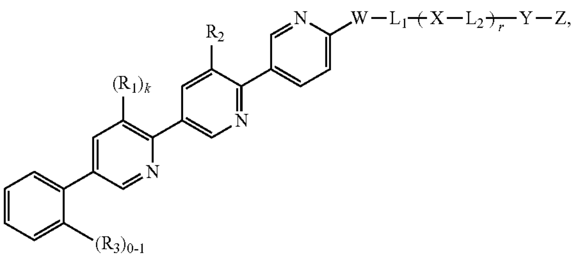

wherein:

$R_1$, $R_2$, $R_3$ are independently, at each occurrence as defined in claim 1.

17. The pharmaceutical composition according to claim 13, wherein the additional anti-cancer agent is chosen from anti-EGFR, anti-Map kinases and anti-Akt compounds.

18. The method according to claim 14, wherein cancer is selected from hematologic malignancies, leukemia, multiple myeloma, solid tumors, mesothelioma, melanoma, pancreas, lung, breast, kidney and liver cancers.

* * * * *